(12) United States Patent
Sah et al.

(10) Patent No.: US 8,314,075 B2
(45) Date of Patent: *Nov. 20, 2012

(54) COMPOSITIONS AND METHODS FOR INHIBITING EXPRESSION OF HUNTINGTIN GENE

(75) Inventors: Dinah Wen-Yee Sah, Boston, MA (US); Philipp Hadwiger, Altenkunstadt (DE); Ingo Roehl, Memmelsdorf (DE); Birgit Bramlage, Kulmbach (DE); Pamela Tan, Kulmbach (DE); Hans-Peter Vornlocher, Bayreuth (DE); David Bumcrot, Belmont, MA (US)

(73) Assignee: Alnylam Pharmaceuticals, Inc., Cambridge, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/252,917

(22) Filed: Oct. 4, 2011

(65) Prior Publication Data
US 2012/0095076 A1 Apr. 19, 2012

Related U.S. Application Data

(63) Continuation of application No. 12/417,502, filed on Apr. 2, 2009, now Pat. No. 8,080,532, which is a continuation of application No. 11/944,961, filed on Nov. 26, 2007, now Pat. No. 7,749,978, which is a continuation of application No. 11/588,674, filed on Oct. 27, 2006, now Pat. No. 7,320,965.

(60) Provisional application No. 60/731,555, filed on Oct. 28, 2005, provisional application No. 60/819,038, filed on Jul. 7, 2006, provisional application No. 60/836,040, filed on Aug. 7, 2006.

(51) Int. Cl.
*A61K 31/70* (2006.01)
*C07H 21/02* (2006.01)
*C07H 21/04* (2006.01)

(52) U.S. Cl. .......... 514/44 A; 536/24.1; 536/24.5
(58) Field of Classification Search .......... 536/23.1, 536/24.3, 24.1, 24.5; 514/44
See application file for complete search history.

(56) References Cited

U.S. PATENT DOCUMENTS
3,687,808 A  8/1972 Merigan, Jr. et al.
(Continued)

FOREIGN PATENT DOCUMENTS
DE  101 00 586  4/2002
(Continued)

OTHER PUBLICATIONS

Agrawal et al., "Antisense therapeutics: is it as simple as complementary base recognition?" *Mol. Med. Today* 6:72-81 (2000).

(Continued)

*Primary Examiner* — Terra Cotta Gibbs
(74) *Attorney, Agent, or Firm* — William D. Schmidt, Esq.; Sorell, Leanna & Schmidt, LLP.

(57) ABSTRACT

The invention relates to a double-stranded ribonucleic acid (dsRNA) for inhibiting the expression of the Huntingtin gene (HD gene), comprising an antisense strand having a nucleotide sequence which is less than 25 nucleotides in length and which is substantially complementary to at least a part of the HD gene. The invention also relates to a pharmaceutical composition comprising the dsRNA together with a pharmaceutically acceptable carrier; methods for treating diseases caused by the expression of the HD gene, or a mutant form thereof, using the pharmaceutical composition; and methods for inhibiting the expression of the huntingtin gene in a cell.

29 Claims, 4 Drawing Sheets

U.S. PATENT DOCUMENTS

| | | | |
|---|---|---|---|
| 4,981,957 A | 1/1991 | Lebleu et al. | |
| 5,034,506 A | 7/1991 | Summerton et al. | |
| 5,118,800 A | 6/1992 | Smith et al. | |
| 5,138,045 A | 8/1992 | Cook et al. | |
| 5,212,295 A | 5/1993 | Cook | |
| 5,218,105 A | 6/1993 | Cook et al. | |
| 5,223,168 A | 6/1993 | Holt | |
| 5,319,080 A | 6/1994 | Leumann | |
| 5,359,044 A | 10/1994 | Cook et al. | |
| 5,378,825 A | 1/1995 | Cook et al. | |
| 5,386,023 A | 1/1995 | Sanghvi et al. | |
| 5,393,878 A | 2/1995 | Leumann | |
| 5,446,137 A | 8/1995 | Maag et al. | |
| 5,457,191 A | 10/1995 | Cook et al. | |
| 5,459,255 A | 10/1995 | Cook et al. | |
| 5,466,786 A | 11/1995 | Buhr et al. | |
| 5,489,677 A | 2/1996 | Sanghvi et al. | |
| 5,506,351 A | 4/1996 | McGee | |
| 5,514,785 A | 5/1996 | Van Ness et al. | |
| 5,519,134 A | 5/1996 | Acevedo et al. | |
| 5,521,302 A | 5/1996 | Cook | |
| 5,539,082 A | 7/1996 | Nielsen et al. | |
| 5,541,307 A | 7/1996 | Cook et al. | |
| 5,554,746 A | 9/1996 | Ravikumar et al. | |
| 5,567,811 A | 10/1996 | Misiura et al. | |
| 5,571,902 A | 11/1996 | Ravikumar et al. | |
| 5,576,427 A | 11/1996 | Cook et al. | |
| 5,578,718 A | 11/1996 | Cook et al. | |
| 5,587,361 A | 12/1996 | Cook et al. | |
| 5,587,469 A | 12/1996 | Cook et al. | |
| 5,587,470 A | 12/1996 | Cook et al. | |
| 5,591,722 A | 1/1997 | Montgomery et al. | |
| 5,597,909 A | 1/1997 | Urdea et al. | |
| 5,599,797 A | 2/1997 | Cook et al. | |
| 5,602,240 A | 2/1997 | De Mesmaeker et al. | |
| 5,608,046 A | 3/1997 | Cook et al. | |
| 5,610,289 A | 3/1997 | Cook et al. | |
| 5,610,300 A | 3/1997 | Altmann et al. | |
| 5,627,053 A | 5/1997 | Usman et al. | |
| 5,639,873 A | 6/1997 | Barascut et al. | |
| 5,646,265 A | 7/1997 | McGee | |
| 5,658,873 A | 8/1997 | Bertsch-Frank et al. | |
| 5,670,633 A | 9/1997 | Cook et al. | |
| 5,686,288 A | 11/1997 | MacDonald et al. | |
| 5,700,920 A | 12/1997 | Altmann et al. | |
| 5,735,814 A | 4/1998 | Elsberry et al. | |
| 5,814,014 A | 9/1998 | Elsberry et al. | |
| 5,859,221 A | 1/1999 | Cook et al. | |
| 6,042,579 A | 3/2000 | Elsberry et al. | |
| 6,093,180 A | 7/2000 | Elsberry | |
| 6,127,533 A | 10/2000 | Cook et al. | |
| 6,166,197 A | 12/2000 | Cook et al. | |
| 6,172,209 B1 | 1/2001 | Manoharan et al. | |
| 6,262,241 B1 | 7/2001 | Cook et al. | |
| 6,271,358 B1 | 8/2001 | Manoharan et al. | |
| 6,551,290 B1 | 4/2003 | Elsberry et al. | |
| 6,594,880 B2 | 7/2003 | Elsberry | |
| 6,945,969 B1 | 9/2005 | Morris et al. | |
| 7,189,222 B2 | 3/2007 | Elsberry | |
| 7,320,965 B2 | 1/2008 | Sah et al. | |
| 7,427,605 B2 | 9/2008 | Davis et al. | |
| 7,589,189 B2 | 9/2009 | Ichiro et al. | |
| 7,718,629 B2 | 5/2010 | Bumcrot et al. | |
| 7,749,978 B2 * | 7/2010 | Sah et al. | 514/44 R |
| 2001/0027309 A1 | 10/2001 | Elsberry | |
| 2001/0027599 A1 | 10/2001 | Elsberry | |
| 2003/0143732 A1 | 7/2003 | Fosnaugh et al. | |
| 2003/0170891 A1 | 9/2003 | McSwiggen | |
| 2004/0259247 A1 | 12/2004 | Tuschl et al. | |
| 2005/0096284 A1 | 5/2005 | McSwiggen | |
| 2006/0263435 A1 | 11/2006 | Davis et al. | |
| 2007/0004664 A1 | 1/2007 | McSwiggen et al. | |
| 2007/0031844 A1 | 2/2007 | Khvorova et al. | |
| 2007/0105803 A1 | 5/2007 | Manoharan et al. | |
| 2007/0281899 A1 | 12/2007 | Bumcrot et al. | |
| 2008/0039415 A1 | 2/2008 | Stewart et al. | |
| 2009/0149403 A1 | 6/2009 | MacLachlan | |
| 2011/0015250 A1 | 1/2011 | Bumcrot et al. | |

FOREIGN PATENT DOCUMENTS

| | | |
|---|---|---|
| WO | WO 93/07883 | 4/1993 |
| WO | WO 99/32619 | 7/1999 |
| WO | WO 99/53050 | 10/1999 |
| WO | WO 99/61631 | 12/1999 |
| WO | WO 00/44895 | 8/2000 |
| WO | WO 2004/058940 A2 | 7/2004 |
| WO | WO 2004/065601 | 8/2004 |
| WO | WO 2004/080406 | 9/2004 |
| WO | WO 2004/090108 | 10/2004 |
| WO | WO 2004/101787 | 11/2004 |
| WO | WO 2005/004794 | 1/2005 |
| WO | WO 2005/089224 | 9/2005 |
| WO | WO 2011/008982 A1 | 1/2011 |

OTHER PUBLICATIONS

Bass, B., "The short answer," Nature, May 24, 2001, pp. 428-429, vol. 411.

Beaucage et al., "Advances in the Synthesis of Oligonucleotides by the Phosphoramidite Approach" *Tetrahedron* 48:2223-2311 (1992).

Boado et al., "Antisense-Mediated Down-Regulation of the Human Huntingtin Gene" *J. Pharmacol. Exp. Ther.* 295:239-243 (2000).

Braasch et al., "Locked nucleic acid (LNA): fine-tuning the recognition of DNA and RNA" *Chem. Biol.* 8:1-7 (2001).

Braasch et al., "Novel Antisense and Peptide Nucleic Acid Strategies for Controlling Gene Expression" *Biochemistry* 41:4503-4510 (2002).

Branch, "A good antisense molecule is hard to find" *Trends Biochem. Sci.* 23:45-50 (1998).

Cook, "Medicinal chemistry of antisense oligonucleotides—future opportunities" *Anticancer Drug Des.* 6:585-607 (1991).

Crooke et al., "Pharmacokinetic Properties of Several Novel Oligonucleotide Analogs in mice" *J. Pharmacol. Exp. Ther.* 277:923-937 (1996).

Delgado et al., "The Uses and Properties of PEG-Linked Proteins" *Crit. Rev. Ther. Drug Carrier Syst.* 9:249-304 (1992).

Elbashir et al., "Functional anatomy of siRNAs for mediating efficient RNAi in *Drosophila melanogaster* embryo lysate" *EMBO J.* 20:6877-6888 (2001).

Elbashir, S., et al., "Analysis of gene function in somatic mammalian cells using small interfering RNAs," Methods, 2002, pp. 199-213, vol. 26.

Elbashir, S., et al., "Duplexes of 21-nucleotide RNAs mediate RNA interference in mammalian cell culture," Nature, May 24, 2001, p. 494-498, vol. 411.

Elbashir, S., et al., "RNA Interference is Mediated by 21- and 22 Nucleotide RNAs," Genes & Development, 2001, pp. 188-200, vol. 15.

Fire, A., "RNA-triggered Gene Silencing," Trends in Genetics, Sep. 1999, pp. 358-363, vol. 15, No. 9.

Fire, A., et al., "Potent and Specific Genetic Interference by Double Stranded RNA in *Caenorhabditis elegans*," Nature, Feb. 19, 1998, pp. 806-811, vol. 391.

GenBank Accession No. NM_002111, "*Homo sapiens* huntingtin (Huntington disease) (HD), mRNA" (Oct. 1, 2006).

GenBank Accession No. NM_010414, "*Mus musculus* Huntington disease gene homolog (Hdh), mRNA" (Oct. 23, 2006).

GenBank Accession No. U18650, "*Rattus norvegicus* Huntington gene product mRNA, complete cds" (Mar. 1, 1996).

Gewirtz et al., "Facilitating oligonucleotide delivery: Helping antisense deliver on its promise" *Proc. Natl. Acad. Sci. USA* 93:3161-3163 (1996).

Guzaev et al., "A Conformationally Preorganized Universal Solid Support for Efficient Oligonucleotide Synthesis" *J. Am. Chem. Soc.* 125:2380-2381 (2003).

Hamm et al., "Incorporation of 2'-Deoxy-2'-mercaptocytidine into Oligonucleotides via Phosphoramidite Chemistry" *J. Org. Chem.* 62:3415-3420 (1997).

Hammond, S., et al., "Post-Transcriptional Gene Silencing by Double-Stranded RNA," Nature Reviews, 2001, vol. 2, pp. 110-119.

Haque, N., et al., "Antisense Gene Therapy for Neurodegenerative Disease?" Experimental Neurology, 1997, pp. 139-146, vol. 144.

Harper, S.Q. et al., "RNA Interference Improves Motor and Neuropathological Abnormalities in a Huntington's Disease Mouse Model," PNAS, Apr. 19, 2005, pp. 5820-5825, vol. 102, No. 16.

Hasholt et al., "Antisense downregulation of mutant huntingtin in a cell model" *J. Gene Med.* 5:528-538 (2003).

Kabanov et al., "A new class of antivirals: antisense oligonucleotides combined with a hydrophobic substituent effectively inhibit influenza virus reproduction and synthesis of virus-specific proteins in MDCK cells" *FEBS Lett.* 259:327-330 (1990).

Koshkin et al., "LNA (Locked Nucleic Acids): Synthesis of the Adenine, Cytosine, Guanine, 5-Methylcytosine, Thymine and Uracil Bicyclonucleoside Monomers, Oligomerisation, and Unprecedented Nucleic Acid Recognition" *Tetrahedron* 54:3607-3630 (1998).

Letsinger et al., "Cholesteryl-conjugated oligonucleotides: Synthesis, properties, and activity as inhibitors of replication of human immunodeficiency virus in cell culture" *Proc. Natl. Acad. Sci. USA* 86:6553-6556 (1989).

Li et al., "Folate-Mediated Targeting of Antisense Oligodeoxynucleotides to Ovarian Cancer Cells" *Pharm. Res.* 15:1540-1545 (1998).

Manoharan, "Oligonucleotide Conjugates as Potential Antisense Drugs with Improved Uptake, Biodistribution, Targeted Delivery, and Mechanism of Action" *Antisense Nucleic Acid Drug Dev.* 12:103-128 (2002).

Manoharan et al., "Chemical Modifications to Improve Uptake and Bioavailability of Antisense Oligonucleotides" *Ann. NY Acad. Sci.* 660:306-309 (1992).

Manoharan et al., "Introduction of a Lipophilic Thioether Tether in the Minor Groove of Nucleic Acids for Antisense Applications" *Bioorg. Med. Chem. Lett.* 3(12):2765-2770 (1993).

Manoharan et al., "Cholic Acid-Oligonucleotide Conjugates for Antisense Applications" *Bioorg. Med. Chem. Lett.* 4(8):1053-1060 (1994).

Manoharan et al., "Oligonucleotide Conjugates Alteration of the Pharmacokinetic Properties of Antisense Agents" *Nucleosides & Nucleotides* 14:969-973 (1995).

Manoharan et al., "Lipidic Nucleic Acids" *Tetrahedron* 36:3651-3654 (1995).

Martin, "A New Access to 2'-*O*-Alkylated Ribonucleosides and Properties of 2'-*O*-Alkylated Oligoribonucleotides" *Helv. Chim. Acta* 78:486-504 (1995) (English abstract included).

Martin et al., "Huntington's Disease. Pathogenesis and Management" *N. Engl. J. Med.* 315:1267-1275 (1986).

Mishra et al., "Improved leishmanicidal effect of phosphorotioate antisense oligonucleotides by LDL-mediated delivery" *Biochim. Biophys. Acta* 1264:229-237 (1995).

Nellemann, C., et al., "Inhibition of Huntingtin Synthesis by Antisense Oligodeoxynucleotides," Molecular and Cellular Neuroscience, 2000, vol. 16, pp. 313-323.

Nielsen et al., "Sequence-Selective Recognition of DNA by Strand Displacement with a Thymine-Substituted Polyamide" *Science* 254:1497-1500 (1991).

Oberhauser et al., "Effective incorporation of 2'-O-methyl-oligoribonucleotides into liposomes and enhanced cell association through modification with thiocholesterol" *Nucleic Acids Res.* 20:533-538 (1992).

Obika et al., "Stability and structural features of the duplexes containing nucleoside analogues with a fixed N-type conformation, 2'-*O*,4'-*C*-methyleneribonucleosides" *Tetrahedron Lett.* 39:5401-5404 (1998).

Ouchi et al., "Synthesis and antitumor activity of poly(ethylene glycol)s linked to 5-fluorouracil via a urethane or urea bond" *Drug Des. Discov.* 9:93-105 (1992).

Park, C., et al., "Double-stranded siRNA targeted to the Huntingtin gene does not induce DNA methylation," Biochemical and Biophysical Research Communications, Oct. 8, 2004, pp. 275-280, vol. 323, No. 1.

Polushin et al., "Synthesis of Oligonucleotides Containing 2'-Azido- and 2'-Amino-2'-deoxyuridine Using Phosphotriester Chemistry" *Tetrahedron Lett.* 37:3227-3230 (1996).

Ravasio et al., "Selective Hydrogenations Promoted by Copper Catalysts. 1. Chemoselectivity, Regioselectivity, and Stereoselectivity in the Hydrogenation of 3-Substituted Steroids" *J. Org. Chem.* 56:4329-4333 (1991).

Rodriguez-Lebron, E. et al., "Intrastriatal rAAV-Mediated Delivery of Anti-huntingtin shRNAs Induces Partial Reversal of Disease Progression in R6/1 Huntington's Disease Transgenic Mice," Molecular Therapy, Oct. 2005, pp. 618-633, vol. 12, No. 4.

Saison-Behmoaras et al., "Short modified antisense oligonucleotides directed against Ha-*ras* point mutation induce selective cleavage of the mRNA and inhibit T24 cells proliferation" *EMBO J.* 10:1111-1118 (1991).

Samukov et al., "2-(4-Nitrophenyl)sulfonylethoxycarbonyl (Nsc) Group As a Base-Labile α-Amino Protection for Solid Phase Peptide Synthesis" *Tetrahedron Lett.* 35:7821-7824 (1994).

Scherer et al., "Approaches for the sequence-specific knockdown of mRNA" *Nat. Biotechnol.* 21:1457-1465 (2003).

Secrist III et al., "Synthesis and biological activity of 4'-thionucleosides" Abstract 21, *Program & Abstracts, Tenth International Roundtable, Nucleosides, Nucleotides and their Biological Applications*, Park City, Utah (Sep. 16-20, 1992).

Shea et al., "Synthesis, hybridization properties and antiviral activity of lipid-oligodeoxynucleotide conjugates" *Nucleic Acids Res.* 18:3777-3783 (1990).

Svinarchuk et al., "Inhibition of HIV proliferation in MT-4 cells by antisense oligonucleotide conjugated to lipophilic groups" *Biochimie* 75:49-54 (1993).

Tamm et al., "Antisense therapy in oncology: new hope for an old idea?" *Lancet* 358:489-497 (2001).

Thomson et al., "Synthesis and Properties of Diuridine Phosphate Analogues Containing Thio and Amino Modifications" *J. Org. Chem.* 61:6273-6281 (1996).

Tuschl, T., "Functional genomics: RNA sets the standard," Nature, Jan. 16, 2003, vol. 421, No. 6920, pp. 220-221.

Tuschl T., "RNA Interference and Small Interfering RNAs" Chembiochem, 2001, pp. 239-245, vol. 2.

Tuschl, T., et al., "Small Interfering RNAs: A Revolutionary Tool for the Analysis of Gene Function and Gene Therapy," Molecular Interventions, 2002, pp. 158-167, vol. 2, No. 3.

Tuschl, T., "Mammalian RNA Interference," RNAi, A Guide to Gene Silencing, Chapter 13, G.J. Hannon (ed,), 2003, pp. 265-295.

Tuschl, T., et al., "Targeted mRNA Degradation by Double-Stranded RNA in Vitro," Genes & Development, 1999, pp. 3191-3197, vol. 13.

Tuschl, T., "Expanding small RNA interference," Nature Biotechnology, May 2002, pp. 446-448, vol. 20.

van Dellen et al., "Genetic and environmental factors in the pathogenesis of Huntington's disease" *Neurogenetics* 5:9-17 (2004).

Verhart et al., "New base-labile amino-protective groups for peptide synthesis" *Recl. Trav. Chim. Pays-Bas* 107:621-626 (1988).

Vickers, T., et al., "Efficient Reduction of Target RNAs by Small Interfering RNA and RNase H-dependent Antisense Agents," The Journal of Biological Chemistry, Feb. 28, 2003, pp. 7108-7118, vol. 278, No. 9.

Wagner, "The state of the art in antisense research" *Nat. Med.* 1:1116-1118 (1995).

Wang, Y.L. et al., "Clinico-pathological Rescue of a Model Mouse of Huntington's Disease by siRNA," Neuroscience Research, Nov. 2005, Epub Aug. 10, 2005, pp. 241-249, vol. 53, No. 3.

Yang et al., "Evidence that processed small dsRNAs may mediate sequence-specific mRNA degradation during RNAi in *Drosophila* embryos" *Curr. Biol.* 10:1191-1200 (2000).

Yen, L., et al., "Sequence-Specific Cleavage of Huntingtin mRNA by Catalytic DNA," Annals of Neurology, 1999, vol. 46, pp. 366-373.

Yuan et al., "siRNA Selection Server: an automated siRNA oligonucleotide prediction server" *Nucleic Acids Res.* 32:W130-W134 (2004).

PCT International Search Report and Written Opinion, PCT/US2006/042420, Jun. 1, 2007, 12 Pages.

Supplementary European Search Report for European Patent Application No. EP 06827135, Sep. 30, 2010, 10 Pages.

Examiner's First Report on Australia Patent Application No. 2006305886, Aug. 18, 2010, 3 pages.

European Search Report for European Patent Application No. EP 11000550, Apr. 26, 2011, 6 Pages.
First Office Action for Chinese Patent Application No. CN 200680046400.X, Nov. 24, 2010, 13 Pages.
Communication pursuant to Article 94(3) EPC for European Patent Application No. EP 11000550.1, Jan. 3, 2012, 4 pages.
Office Action for Canadian Patent Application No. CA 2,627,025, Nov. 14, 2011, 4 pages.
Second Office Action for Chinese Patent Application No. CN 200680046400.X, Aug. 3, 2011, 9 Pages.
Notice of Reasons for Rejection, Japanese Patent Application No. JP 2008-538099, Jun. 1, 2011, 9 Pages.
Reynolds, et al. (2004) "Rational siRNA design for RNA interference," Nature Biotechnology, vol. 22, No. 3, pp. 326-330.

Robbins, M., et al., "Stable expression of shRNAs in human CD34+progenitor cells can avoid induction of interferon responses to siRNAs in vitro," Nature Biotechnology, May 2006, pp. 566-571, vol. 24, No. 5.
Rose, S., et al., "Functional polarity is introduced by Dicer processing of short substrate RNAs," Nucleic Acids Research, 2005, pp. 4140-4156, vol. 33, No. 13.
Weil, et al (2002) "Targeting the Kinesin Eg5 to Monitor siRNA Transfection in Mammalian Cells," *Biotechniques* 33(6):1244-1248.
Zimmerman, et al. (2006) "RNAi-mediated gene silencing in non-human primates," *Nature*, vol. 441, May 4: 111-114.

\* cited by examiner

SEQUENCE LISTING

<160> NUMBER OF SEQ ID NOS: 890

<210> SEQ ID NO 1
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

```
<400> SEQUENCE: 1
gaaucgagau cggauguca                                              19

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 2
gaaucgagau cggaugucat t                                           21

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 3
ugacauccga ucucgauuct t                                           21

<210> SEQ ID NO 4
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 4
aaauccugcu uuagucgag                                              19

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 5
aaauccugcu uuagucgagt t                                           21

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 6
cucgacuaaa gcaggauuut t                                           21
```

```
<210> SEQ ID NO 7
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 7
agucaguccg gguagaacu                                                     19

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 8
agucaguccg gguagaacut t                                                  21

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 9
aguucuaccc ggacugacut t                                                  21

<210> SEQ ID NO 10
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 10
gguuuaugaa cugacguua                                                     19

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 11
gguuuaugaa cugacguuat t                                                  21

<210> SEQ ID NO 12
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 12
uaacgucagu ucauaaacct t                                                    21

<210> SEQ ID NO 13
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 13
guuacggguu aauuacugu                                                       19

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 14
guuacggguu aauuacugut t                                                    21

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 15
acaguaauua acccguaact t                                                    21

<210> SEQ ID NO 16
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 16
ugcuuuaguc gagaaccaa                                                       19

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin
```

-continued

<400> SEQUENCE: 17
ugcuuuaguc gagaaccaat t                                              21

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 18
uugguucucg acuaaagcat t                                              21

<210> SEQ ID NO 19
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 19
ucuguaccgu ugaguccca                                                 19

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 20
ucuguaccgu ugagucccat t                                              21

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 21
ugggacucaa cgguacagat t                                              21

<210> SEQ ID NO 22
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 22
aaauuguguu agacgguac                                                 19

```
<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 23
aaauuguguu agacgguact t                                                 21

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 24
guaccgucua acacaauuut t                                                 21

<210> SEQ ID NO 25
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 25
uggccggaaa cuugcuugc                                                    19

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 26
uggccggaaa cuugcuugct t                                                 21

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 27
gcaagcaagu uuccggccat t                                                 21

<210> SEQ ID NO 28
<211> LENGTH: 19
<212> TYPE: RNA
```

```
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 28
guucaguuac ggguuaauu                                                    19

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 29
guucaguuac ggguuaauut t                                                 21

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 30
aauuaacccg uaacugaact t                                                 21

<210> SEQ ID NO 31
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 31
gcgggcucgu uccaugauc                                                    19

<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 32
gcgggcucgu uccaugauct t                                                 21

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
```

Synthetic siRNA sequence specific for huntingtin

<400> SEQUENCE: 33
gaucauggaa cgagcccgct t                                              21

<210> SEQ ID NO 34
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 34
gacuccgagc acuuaacgu                                                 19

<210> SEQ ID NO 35
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 35
gacuccgagc acuuaacgut t                                              21

<210> SEQ ID NO 36
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 36
acguuaagug cucggaguct t                                              21

<210> SEQ ID NO 37
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 37
cgcauggucg acauccuug                                                 19

<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 38
cgcauggucg acauccuugt t                                              21

<210> SEQ ID NO 39
<211> LENGTH: 21
<212> TYPE: DNA
<213> ORGANISM: Artificial Sequence
<220> FEATURE:
<223> OTHER INFORMATION: Description of Artificial Sequence: Synthetic siRNA sequence specific for huntingtin
<220> FEATURE:
<223> OTHER INFORMATION: Description of Combined DNA/RNA Molecule: Synthetic siRNA sequence specific for huntingtin

<400> SEQUENCE: 39
caaggauguc gaccaugcgt t                                               21

<210> SEQ ID NO 40
<211> LENGTH: 19
<212> TYPE: RNA
<213> ORGANISM: Artificial Sequence
<220> FEATURE:
<223> OTHER INFORMATION: Description of Artificial Sequence: Synthetic siRNA sequence specific for huntingtin

<400> SEQUENCE: 40
aagacgagau ccucgcuca                                                  19

<210> SEQ ID NO 41
<211> LENGTH: 21
<212> TYPE: DNA
<213> ORGANISM: Artificial Sequence
<220> FEATURE:
<223> OTHER INFORMATION: Description of Artificial Sequence: Synthetic siRNA sequence specific for huntingtin
<220> FEATURE:
<223> OTHER INFORMATION: Description of Combined DNA/RNA Molecule: Synthetic siRNA sequence specific for huntingtin

<400> SEQUENCE: 41
aagacgagau ccucgcucat t                                               21

<210> SEQ ID NO 42
<211> LENGTH: 21
<212> TYPE: DNA
<213> ORGANISM: Artificial Sequence
<220> FEATURE:
<223> OTHER INFORMATION: Description of Artificial Sequence: Synthetic siRNA sequence specific for huntingtin
<220> FEATURE:
<223> OTHER INFORMATION: Description of Combined DNA/RNA Molecule: Synthetic siRNA sequence specific for huntingtin

<400> SEQUENCE: 42
ugagcgagga ucucgucuut t                                               21

<210> SEQ ID NO 43
<211> LENGTH: 19
<212> TYPE: RNA
<213> ORGANISM: Artificial Sequence
<220> FEATURE:
<223> OTHER INFORMATION: Description of Artificial Sequence: Synthetic siRNA sequence specific for huntingtin

<400> SEQUENCE: 43
aagucagucc ggguagaac                                                  19

<210> SEQ ID NO 44
<211> LENGTH: 21
<212> TYPE: DNA
<213> ORGANISM: Artificial Sequence
<220> FEATURE:

```
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 44
aagucagucc gggtagaact t                                              21

<210> SEQ ID NO 45
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 45
guucuacccg gacugacuut t                                              21

<210> SEQ ID NO 46
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 46
aaggccuuca uagcgaacc                                                 19

<210> SEQ ID NO 47
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 47
aaggccuuca uagcgaacct t                                              21

<210> SEQ ID NO 48
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 48
gguucgcuau gaaggccuut t                                              21

<210> SEQ ID NO 49
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin
```

```
<400> SEQUENCE: 49
aggccuucau agcgaaccu                                                    19

<210> SEQ ID NO 50
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 50
aggccuucau agcgaaccut t                                                 21

<210> SEQ ID NO 51
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 51
agguucgcua ugaaggccut t                                                 21

<210> SEQ ID NO 52
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 52
acuccgagca cuuaacgug                                                    19

<210> SEQ ID NO 53
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 53
acuccgagca cuuaacgugt t                                                 21

<210> SEQ ID NO 54
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 54
cacguuaagu gcucggagut t                                                 21
```

```
<210> SEQ ID NO 55
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 55
uaaaggccuu cauagcgaa                                                      19

<210> SEQ ID NO 56
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 56
uaaaggccuu cauagcgaat t                                                   21

<210> SEQ ID NO 57
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 57
uucgcuauga aggccuuuat t                                                   21

<210> SEQ ID NO 58
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 58
ucugaaucga gaucggaug                                                      19

<210> SEQ ID NO 59
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 59
ucugaaucga gaucggaugt t                                                   21

<210> SEQ ID NO 60
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 60
cauccgaucu cgauucagat t                                              21

<210> SEQ ID NO 61
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 61
ugaaauugug uuagacggu                                                 19

<210> SEQ ID NO 62
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 62
ugaaauugug uuagacggut t                                              21

<210> SEQ ID NO 63
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 63
accgucuaac acaauuucat t                                              21

<210> SEQ ID NO 64
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 64
uggcucgcau ggucgacau                                                 19

<210> SEQ ID NO 65
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin
```

-continued

```
<400> SEQUENCE: 65
uggcucgcau ggucgacaut t                                              21

<210> SEQ ID NO 66
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 66
augucgacca ugcgagccat t                                              21

<210> SEQ ID NO 67
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 67
aaagucaguc cggguagaa                                                 19

<210> SEQ ID NO 68
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 68
aaagucaguc cggguagaat t                                              21

<210> SEQ ID NO 69
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 69
uucuacccgg acugacuuut t                                              21

<210> SEQ ID NO 70
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 70
gagugcccgu gucgguucu                                                 19
```

<210> SEQ ID NO 71
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 71
gagugcccgu gucgguucut t                                              21

<210> SEQ ID NO 72
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 72
agaaccgaca cgggcacuct t                                              21

<210> SEQ ID NO 73
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 73
ggagcucggg acggauagu                                                 19

<210> SEQ ID NO 74
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 74
ggagcucggg acggauagut t                                              21

<210> SEQ ID NO 75
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 75
acuauccguc ccgagcucct t                                              21

<210> SEQ ID NO 76
<211> LENGTH: 19
<212> TYPE: RNA

```
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 76
agaaaacaag ccuugccgc                                                    19

<210> SEQ ID NO 77
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 77
agaaaacaag ccuugccgct t                                                 21

<210> SEQ ID NO 78
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 78
gcggcaaggc uuguuuucut t                                                 21

<210> SEQ ID NO 79
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 79
auaaucacau ucguuuguu                                                    19

<210> SEQ ID NO 80
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 80
auaaucacau ucguuuguut t                                                 21

<210> SEQ ID NO 81
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
```

```
      Synthetic siRNA sequence specific for huntingtin

<400> SEQUENCE: 81
aacaaacgaa ugugauuaut t                                              21

<210> SEQ ID NO 82
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 82
ucugggcauc gcuauggaa                                                 19

<210> SEQ ID NO 83
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 83
ucugggcauc gcuauggaat t                                              21

<210> SEQ ID NO 84
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 84
uuccauagcg augcccagat t                                              21

<210> SEQ ID NO 85
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 85
ggccuucaua gcgaaccug                                                 19

<210> SEQ ID NO 86
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 86
ggccuucaua gcgaaccugt t                                              21
```

<210> SEQ ID NO 87
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 87
cagguucgcu augaaggcct t                                              21

<210> SEQ ID NO 88
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 88
cuaaaugugc ucuuaggcu                                                 19

<210> SEQ ID NO 89
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 89
cuaaaugugc ucuuaggcut t                                              21

<210> SEQ ID NO 90
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 90
agccuaagag cacauuuagt t                                              21

<210> SEQ ID NO 91
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 91
guuuaugaac ugacguuac                                                 19

<210> SEQ ID NO 92
<211> LENGTH: 21
<212> TYPE: DNA
<213> ORGANISM: Artificial Sequence
<220> FEATURE:

<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 92
guuuaugaac ugacguuact t                                            21

<210> SEQ ID NO 93
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 93
guaacgucag uucauaaact t                                            21

<210> SEQ ID NO 94
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 94
uuuaugaacu gacguuaca                                               19

<210> SEQ ID NO 95
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 95
uuuaugaacu gacguuacat t                                            21

<210> SEQ ID NO 96
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 96
uguaacguca guucauaaat t                                            21

<210> SEQ ID NO 97
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

```
<400> SEQUENCE: 97
augaacugac guuacauca                                                19

<210> SEQ ID NO 98
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 98
augaacugac guuacaucat t                                             21

<210> SEQ ID NO 99
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 99
ugauguaacg ucaguucaut t                                             21

<210> SEQ ID NO 100
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 100
ccacaauguu gugaccgga                                                19

<210> SEQ ID NO 101
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 101
ccacaauguu gugaccggat t                                             21

<210> SEQ ID NO 102
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 102
uccggucaca acauguggt t                                              21
```

<210> SEQ ID NO 103
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 103
cugguggccg aagccguag                                                19

<210> SEQ ID NO 104
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 104
cugguggccg aagccguagt t                                             21

<210> SEQ ID NO 105
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 105
cuacggcuuc ggccaccagt t                                             21

<210> SEQ ID NO 106
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 106
aauuguguua gacgguacc                                                19

<210> SEQ ID NO 107
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 107
aauuguguua gacgguacct t                                             21

<210> SEQ ID NO 108
<211> LENGTH: 21
<212> TYPE: DNA
<213> ORGANISM: Artificial Sequence

```
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 108
gguaccgucu aacacaauut t                                                     21

<210> SEQ ID NO 109
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 109
uuguguuaga cgguaccga                                                        19

<210> SEQ ID NO 110
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 110
uuguguuaga cgguaccgat t                                                     21

<210> SEQ ID NO 111
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 111
ucgguaccgu cuaacacaat t                                                     21

<210> SEQ ID NO 112
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 112
aaaacaagcc uugccgcau                                                        19

<210> SEQ ID NO 113
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin
```

```
<400> SEQUENCE: 113
aaaacaagcc uugccgcaut t                                        21

<210> SEQ ID NO 114
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 114
augcggcaag gcuuguuuut t                                        21

<210> SEQ ID NO 115
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 115
aagagcugua ccguuggga                                           19

<210> SEQ ID NO 116
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 116
aagagcugua ccguugggat t                                        21

<210> SEQ ID NO 117
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 117
ucccaacggu acagcucuut t                                        21

<210> SEQ ID NO 118
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 118
auaccucagg uccuguuac                                           19
```

```
<210> SEQ ID NO 119
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 119
auaccucagg uccuguuact t                                             21

<210> SEQ ID NO 120
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 120
guaacaggac cugagguaut t                                             21

<210> SEQ ID NO 121
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 121
uccugcuuua gucgagaac                                                19

<210> SEQ ID NO 122
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 122
uccugcuuua gucgagaact t                                             21

<210> SEQ ID NO 123
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 123
guucucgacu aaagcaggat t                                             21

<210> SEQ ID NO 124
<211> LENGTH: 19
<212> TYPE: RNA
```

```
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 124
cauaaucaca uucguuugu                                                    19

<210> SEQ ID NO 125
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 125
cauaaucaca uucguuugut t                                                 21

<210> SEQ ID NO 126
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 126
acaaacgaau gugauuaugt t                                                 21

<210> SEQ ID NO 127
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 127
aagcgacugu cucgacaga                                                    19

<210> SEQ ID NO 128
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 128
aagcgacugu cucgacagat t                                                 21

<210> SEQ ID NO 129
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
```

-continued

Synthetic siRNA sequence specific for huntingtin

<400> SEQUENCE: 129
ucugucgaga cagucgcuut t                                              21

<210> SEQ ID NO 130
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 130
ccgagcacuu aacguggcu                                                 19

<210> SEQ ID NO 131
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 131
ccgagcacuu aacguggcut t                                              21

<210> SEQ ID NO 132
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 132
agccacguua agugcucggt t                                              21

<210> SEQ ID NO 133
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 133
cuggcucgca uggucgaca                                                 19

<210> SEQ ID NO 134
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 134
cuggcucgca uggucgacat t                                              21

<210> SEQ ID NO 135
<211> LENGTH: 21
<212> TYPE: DNA
<213> ORGANISM: Artificial Sequence
<220> FEATURE:
<223> OTHER INFORMATION: Description of Artificial Sequence: Synthetic
siRNA sequence specific for huntingtin
<220> FEATURE:
<223> OTHER INFORMATION: Description of Combined DNA/RNA Molecule:
Synthetic siRNA sequence specific for huntingtin

<400> SEQUENCE: 135
ugucgaccau gcgagccagt t                                              21

<210> SEQ ID NO 136
<211> LENGTH: 19
<212> TYPE: RNA
<213> ORGANISM: Artificial Sequence
<220> FEATURE:
<223> OTHER INFORMATION: Description of Artificial Sequence: Synthetic
siRNA sequence specific for huntingtin

<400> SEQUENCE: 136
uugucgccgg guagaaaug                                                 19

<210> SEQ ID NO 137
<211> LENGTH: 21
<212> TYPE: DNA
<213> ORGANISM: Artificial Sequence
<220> FEATURE:
<223> OTHER INFORMATION: Description of Artificial Sequence: Synthetic
siRNA sequence specific for huntingtin
<220> FEATURE:
<223> OTHER INFORMATION: Description of Combined DNA/RNA Molecule:
Synthetic siRNA sequence specific for huntingtin

<400> SEQUENCE: 137
uugucgccgg guagaaaugt t                                              21

<210> SEQ ID NO 138
<211> LENGTH: 21
<212> TYPE: DNA
<213> ORGANISM: Artificial Sequence
<220> FEATURE:
<223> OTHER INFORMATION: Description of Artificial Sequence: Synthetic
siRNA sequence specific for huntingtin
<220> FEATURE:
<223> OTHER INFORMATION: Description of Combined DNA/RNA Molecule:
Synthetic siRNA sequence specific for huntingtin

<400> SEQUENCE: 138
cauuucuacc cggcgacaat t                                              21

<210> SEQ ID NO 139
<211> LENGTH: 19
<212> TYPE: RNA
<213> ORGANISM: Artificial Sequence
<220> FEATURE:
<223> OTHER INFORMATION: Description of Artificial Sequence: Synthetic
siRNA sequence specific for huntingtin

<400> SEQUENCE: 139
ugcaagacuc acuuagucc                                                 19

<210> SEQ ID NO 140
<211> LENGTH: 21
<212> TYPE: DNA
<213> ORGANISM: Artificial Sequence
<220> FEATURE:

<223> OTHER INFORMATION: Description of Artificial Sequence: Synthetic
     siRNA sequence specific for huntingtin
<220> FEATURE:
<223> OTHER INFORMATION: Description of Combined DNA/RNA Molecule:
     Synthetic siRNA sequence specific for huntingtin

<400> SEQUENCE: 140
ugcaagacuc acuuagucct t                                          21

<210> SEQ ID NO 141
<211> LENGTH: 21
<212> TYPE: DNA
<213> ORGANISM: Artificial Sequence
<220> FEATURE:
<223> OTHER INFORMATION: Description of Artificial Sequence: Synthetic
     siRNA sequence specific for huntingtin
<220> FEATURE:
<223> OTHER INFORMATION: Description of Combined DNA/RNA Molecule:
     Synthetic siRNA sequence specific for huntingtin

<400> SEQUENCE: 141
ggacuaagug agucuugcat t                                          21

<210> SEQ ID NO 142
<211> LENGTH: 19
<212> TYPE: RNA
<213> ORGANISM: Artificial Sequence
<220> FEATURE:
<223> OTHER INFORMATION: Description of Artificial Sequence: Synthetic
     siRNA sequence specific for huntingtin

<400> SEQUENCE: 142
gaaacaguga guccggaca                                             19

<210> SEQ ID NO 143
<211> LENGTH: 21
<212> TYPE: DNA
<213> ORGANISM: Artificial Sequence
<220> FEATURE:
<223> OTHER INFORMATION: Description of Artificial Sequence: Synthetic
     siRNA sequence specific for huntingtin
<220> FEATURE:
<223> OTHER INFORMATION: Description of Combined DNA/RNA Molecule:
     Synthetic siRNA sequence specific for huntingtin

<400> SEQUENCE: 143
gaaacaguga guccggacat t                                          21

<210> SEQ ID NO 144
<211> LENGTH: 21
<212> TYPE: DNA
<213> ORGANISM: Artificial Sequence
<220> FEATURE:
<223> OTHER INFORMATION: Description of Artificial Sequence: Synthetic
     siRNA sequence specific for huntingtin
<220> FEATURE:
<223> OTHER INFORMATION: Description of Combined DNA/RNA Molecule:
     Synthetic siRNA sequence specific for huntingtin

<400> SEQUENCE: 144
uguccggacu cacuguuuct t                                          21

<210> SEQ ID NO 145
<211> LENGTH: 19
<212> TYPE: RNA
<213> ORGANISM: Artificial Sequence
<220> FEATURE:
<223> OTHER INFORMATION: Description of Artificial Sequence: Synthetic
     siRNA sequence specific for huntingtin

```
<400> SEQUENCE: 145
aaaucccagu guuggacca                                              19

<210> SEQ ID NO 146
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 146
aaaucccagu guuggaccat t                                           21

<210> SEQ ID NO 147
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 147
ugguccaaca cugggauuut t                                           21

<210> SEQ ID NO 148
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 148
gcuagcucca ugcuuaagc                                              19

<210> SEQ ID NO 149
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 149
gcuagcucca ugcuuaagct t                                           21

<210> SEQ ID NO 150
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 150
gcuuaagcau ggagcuagct t                                           21
```

-continued

```
<210> SEQ ID NO 151
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 151
uccaugcuua agccuaggg                                                        19

<210> SEQ ID NO 152
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 152
uccaugcuua agccuagggt t                                                     21

<210> SEQ ID NO 153
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 153
cccuaggcuu aagcauggat t                                                     21

<210> SEQ ID NO 154
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 154
ccaugcuuaa gccuaggga                                                        19

<210> SEQ ID NO 155
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 155
ccaugcuuaa gccuagggat t                                                     21

<210> SEQ ID NO 156
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 156
ucccuaggcu uaagcauggt t                                             21

<210> SEQ ID NO 157
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 157
ucaacagcua cacacgugu                                                19

<210> SEQ ID NO 158
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 158
ucaacagcua cacacgugut t                                             21

<210> SEQ ID NO 159
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 159
acacgugugu agcuguugat t                                             21

<210> SEQ ID NO 160
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 160
augugugcca cugcguuuu                                                19

<210> SEQ ID NO 161
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin
```

```
<400> SEQUENCE: 161
augugugcca cugcguuuut t                                              21

<210> SEQ ID NO 162
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 162
aaaacgcagu ggcacacaut t                                              21

<210> SEQ ID NO 163
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 163
ugugugccac ugcguuuua                                                 19

<210> SEQ ID NO 164
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 164
ugugugccac ugcguuuuat t                                              21

<210> SEQ ID NO 165
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 165
uaaaacgcag uggcacacat t                                              21

<210> SEQ ID NO 166
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 166
ucaguccggg uagaacuuc                                                 19
```

```
<210> SEQ ID NO 167
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 167
ucaguccggg uagaacuuct t                                            21

<210> SEQ ID NO 168
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 168
gaaguucuac ccggacugat t                                            21

<210> SEQ ID NO 169
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 169
aguccgggua gaacuucag                                               19

<210> SEQ ID NO 170
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 170
aguccgggua gaacuucagt t                                            21

<210> SEQ ID NO 171
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 171
cugaaguucu acccggacut t                                            21

<210> SEQ ID NO 172
<211> LENGTH: 19
<212> TYPE: RNA
```

```
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 172
gauuguugcu auggagcgg                                                    19

<210> SEQ ID NO 173
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 173
gauuguugcu auggagcggt t                                                 21

<210> SEQ ID NO 174
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 174
ccgcuccaua gcaacaauct t                                                 21

<210> SEQ ID NO 175
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 175
acuuguuuac gaaaugucc                                                    19

<210> SEQ ID NO 176
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 176
acuuguuuac gaaaugucct t                                                 21

<210> SEQ ID NO 177
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
```

Synthetic siRNA sequence specific for huntingtin

<400> SEQUENCE: 177
ggacauuucg uaaacaagut t                                              21

<210> SEQ ID NO 178
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 178
cuuguuuacg aaaugucca                                                 19

<210> SEQ ID NO 179
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 179
cuuguuuacg aaauguccat t                                              21

<210> SEQ ID NO 180
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 180
uggacauuuc guaaacaagt t                                              21

<210> SEQ ID NO 181
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 181
gcuuccgcac augccgcgg                                                 19

<210> SEQ ID NO 182
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 182
gcuuccgcac augccgcggt t                                              21

<210> SEQ ID NO 183
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 183
ccgcggcaug ugcggaagct t                                              21

<210> SEQ ID NO 184
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 184
uaauuuuaac guaacucuu                                                 19

<210> SEQ ID NO 185
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 185
uaauuuuaac guaacucuut t                                              21

<210> SEQ ID NO 186
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 186
aagaguuacg uuaaaauuat t                                              21

<210> SEQ ID NO 187
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 187
cuuucuaugc ccguguaaa                                                 19

<210> SEQ ID NO 188
<211> LENGTH: 21
<212> TYPE: DNA
<213> ORGANISM: Artificial Sequence
<220> FEATURE:

-continued

<223> OTHER INFORMATION: Description of Artificial Sequence: Synthetic
     siRNA sequence specific for huntingtin
<220> FEATURE:
<223> OTHER INFORMATION: Description of Combined DNA/RNA Molecule:
     Synthetic siRNA sequence specific for huntingtin

<400> SEQUENCE: 188
cuuucuaugc ccguguaaat t                                            21

<210> SEQ ID NO 189
<211> LENGTH: 21
<212> TYPE: DNA
<213> ORGANISM: Artificial Sequence
<220> FEATURE:
<223> OTHER INFORMATION: Description of Artificial Sequence: Synthetic
     siRNA sequence specific for huntingtin
<220> FEATURE:
<223> OTHER INFORMATION: Description of Combined DNA/RNA Molecule:
     Synthetic siRNA sequence specific for huntingtin

<400> SEQUENCE: 189
uuuacacggg cauagaaagt t                                            21

<210> SEQ ID NO 190
<211> LENGTH: 19
<212> TYPE: RNA
<213> ORGANISM: Artificial Sequence
<220> FEATURE:
<223> OTHER INFORMATION: Description of Artificial Sequence: Synthetic
     siRNA sequence specific for huntingtin

<400> SEQUENCE: 190
aaagggaagg acugacgag                                               19

<210> SEQ ID NO 191
<211> LENGTH: 21
<212> TYPE: DNA
<213> ORGANISM: Artificial Sequence
<220> FEATURE:
<223> OTHER INFORMATION: Description of Artificial Sequence: Synthetic
     siRNA sequence specific for huntingtin
<220> FEATURE:
<223> OTHER INFORMATION: Description of Combined DNA/RNA Molecule:
     Synthetic siRNA sequence specific for huntingtin

<400> SEQUENCE: 191
aaagggaagg acugacgagt t                                            21

<210> SEQ ID NO 192
<211> LENGTH: 21
<212> TYPE: DNA
<213> ORGANISM: Artificial Sequence
<220> FEATURE:
<223> OTHER INFORMATION: Description of Artificial Sequence: Synthetic
     siRNA sequence specific for huntingtin
<220> FEATURE:
<223> OTHER INFORMATION: Description of Combined DNA/RNA Molecule:
     Synthetic siRNA sequence specific for huntingtin

<400> SEQUENCE: 192
cucgucaguc cuucccuuut t                                            21

<210> SEQ ID NO 193
<211> LENGTH: 19
<212> TYPE: RNA
<213> ORGANISM: Artificial Sequence
<220> FEATURE:
<223> OTHER INFORMATION: Description of Artificial Sequence: Synthetic
     siRNA sequence specific for huntingtin

```
<400> SEQUENCE: 193
gcuggcucgc auggucgac                                              19

<210> SEQ ID NO 194
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 194
gcuggcucgc auggucgact t                                           21

<210> SEQ ID NO 195
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 195
gucgaccaug cgagccagct t                                           21

<210> SEQ ID NO 196
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 196
ugacguuaca ucauacaca                                              19

<210> SEQ ID NO 197
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 197
ugacguuaca ucauacacat t                                           21

<210> SEQ ID NO 198
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 198
uguguaugau guaacgucat t                                           21
```

<210> SEQ ID NO 199
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 199
acgguaccga caaccagua                                                        19

<210> SEQ ID NO 200
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 200
acgguaccga caaccaguat t                                                     21

<210> SEQ ID NO 201
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 201
uacugguugu cgguaccgut t                                                     21

<210> SEQ ID NO 202
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 202
gguaccgaca accaguauu                                                        19

<210> SEQ ID NO 203
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 203
gguaccgaca accaguauut t                                                     21

<210> SEQ ID NO 204
<211> LENGTH: 21
<212> TYPE: DNA
<213> ORGANISM: Artificial Sequence

```
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 204
aauacugguu gucgguacct t                                              21

<210> SEQ ID NO 205
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 205
acgagugcuc aauaauguu                                                 19

<210> SEQ ID NO 206
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 206
acgagugcuc aauaauguut t                                              21

<210> SEQ ID NO 207
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 207
aacauuauug agcacucgut t                                              21

<210> SEQ ID NO 208
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 208
caucggagag uuucugucc                                                 19

<210> SEQ ID NO 209
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin
```

<400> SEQUENCE: 209
caucggagag uuucugucct t                 21

<210> SEQ ID NO 210
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 210
ggacagaaac ucuccgaugt t                 21

<210> SEQ ID NO 211
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 211
gcgaaccuga agucaagcu                 19

<210> SEQ ID NO 212
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 212
gcgaaccuga agucaagcut t                 21

<210> SEQ ID NO 213
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 213
agcuugacuu cagguucgct t                 21

<210> SEQ ID NO 214
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 214
cugaaucgag aucggaugu                 19

```
<210> SEQ ID NO 215
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 215
cugaaucgag aucggaugut t                                              21

<210> SEQ ID NO 216
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 216
acauccgauc ucgauucagt t                                              21

<210> SEQ ID NO 217
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 217
cgguaccgac aaccaguau                                                 19

<210> SEQ ID NO 218
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 218
cgguaccgac aaccaguaut t                                              21

<210> SEQ ID NO 219
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 219
auacugguug ucgguaccgt t                                              21

<210> SEQ ID NO 220
<211> LENGTH: 19
<212> TYPE: RNA
```

```
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 220
acugaaccgg gugaucaag                                              19

<210> SEQ ID NO 221
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 221
acugaaccgg gugaucaagt t                                           21

<210> SEQ ID NO 222
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 222
cuugaucacc cgguucagut t                                           21

<210> SEQ ID NO 223
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 223
ccuugccgca ucaaggug                                               19

<210> SEQ ID NO 224
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 224
ccuugccgca ucaaggugt t                                            21

<210> SEQ ID NO 225
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
```

Synthetic siRNA sequence specific for huntingtin

<400> SEQUENCE: 225
caccuuugau gcggcaaggt t                                                    21

<210> SEQ ID NO 226
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 226 cuuggcgga uugcauucc                                                        19

<210> SEQ ID NO 227
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 227 cuuggcgga uugcauucct t                                                     21

<210> SEQ ID NO 228
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 228
ggaaugcaau ccgccaaagt t                                                    21

<210> SEQ ID NO 229
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 229
cuguaccguu gagucccaa                                                       19

<210> SEQ ID NO 230
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 230
cuguaccguu gagucccaat t                                                    21

```
<210> SEQ ID NO 231
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 231
uugggacuca acgguacagt t                                              21

<210> SEQ ID NO 232
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 232
uguaccguug agucccaag                                                 19

<210> SEQ ID NO 233
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 233
uguaccguug agucccaagt t                                              21

<210> SEQ ID NO 234
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 234
cuugggacuc aacgguacat t                                              21

<210> SEQ ID NO 235
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 235
agucgagaac caaugaugg                                                 19

<210> SEQ ID NO 236
<211> LENGTH: 21
<212> TYPE: DNA
<213> ORGANISM: Artificial Sequence
<220> FEATURE:
```

```
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 236
agucgagaac caaugauggt t                                               21

<210> SEQ ID NO 237
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 237
ccaucauugg uucucgacut t                                               21

<210> SEQ ID NO 238
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 238
ccgacuaccg cugugggc                                                   19

<210> SEQ ID NO 239
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 239
ccgacuaccg cugugggct t                                                21

<210> SEQ ID NO 240
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 240
gcccaccagc gguagucggt t                                               21

<210> SEQ ID NO 241
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin
```

```
<400> SEQUENCE: 241
auaucaccgg cugcugacu                                                    19

<210> SEQ ID NO 242
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 242
auaucaccgg cugcugacut t                                                 21

<210> SEQ ID NO 243
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 243
agucagcagc cggugauaut t                                                 21

<210> SEQ ID NO 244
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 244
ugcauaucgc ugggcucaa                                                    19

<210> SEQ ID NO 245
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 245
ugcauaucgc ugggcucaat t                                                 21

<210> SEQ ID NO 246
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 246
uugagcccag cgauaugcat t                                                 21
```

```
<210> SEQ ID NO 247
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 247
uuguuuacga cgugaucua                                                  19

<210> SEQ ID NO 248
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 248
uuguuuacga cgugaucuat t                                               21

<210> SEQ ID NO 249
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 249
uagaucacgu cguaaacaat t                                               21

<210> SEQ ID NO 250
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 250
guguuagacg guaccgaca                                                  19

<210> SEQ ID NO 251
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 251
guguuagacg guaccgacat t                                               21

<210> SEQ ID NO 252
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 252
ugucgguacc gucuaacact t                                              21

<210> SEQ ID NO 253
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 253
cuugaacuac aucgaucau                                                 19

<210> SEQ ID NO 254
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 254
cuugaacuac aucgaucaut t                                              21

<210> SEQ ID NO 255
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 255
augaucgaug uaguucaagt t                                              21

<210> SEQ ID NO 256
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 256
ggccggaaac uugcuugca                                                 19

<210> SEQ ID NO 257
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin
```

```
<400> SEQUENCE: 257
ggccggaaac uugcuugcat t                                          21

<210> SEQ ID NO 258
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 258
ugcaagcaag uuuccggcct t                                          21

<210> SEQ ID NO 259
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 259
cugucucgac agauagcug                                             19

<210> SEQ ID NO 260
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 260
cugucucgac agauagcugt t                                          21

<210> SEQ ID NO 261
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 261
cagcuaucug ucgagacagt t                                          21

<210> SEQ ID NO 262
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 262
gcaucgcuau ggaacuuuu                                             19
```

```
<210> SEQ ID NO 263
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 263
gcaucgcuau ggaacuuuut t                                                21

<210> SEQ ID NO 264
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 264
aaaaguucca uagcgaugct t                                                21

<210> SEQ ID NO 265
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 265
acugacguua caucauaca                                                   19

<210> SEQ ID NO 266
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 266
acugacguua caucauacat t                                                21

<210> SEQ ID NO 267
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 267
uguaugaugu aacgucagut t                                                21

<210> SEQ ID NO 268
<211> LENGTH: 19
<212> TYPE: RNA
```

```
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 268
cugacguuac aucauacac                                                  19

<210> SEQ ID NO 269
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 269
cugacguuac aucauacact t                                               21

<210> SEQ ID NO 270
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 270
guguaugaug uaacgucagt t                                               21

<210> SEQ ID NO 271
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 271
ugaaucgaga ucggauguc                                                  19

<210> SEQ ID NO 272
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 272
ugaaucgaga ucggauguct t                                               21

<210> SEQ ID NO 273
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
```

Synthetic siRNA sequence specific for huntingtin

<400> SEQUENCE: 273
gacauccgau cucgauucat t                                              21

<210> SEQ ID NO 274
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 274
uagacgguac cgacaacca                                                 19

<210> SEQ ID NO 275
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 275
uagacgguac cgacaaccat t                                              21

<210> SEQ ID NO 276
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 276
ugguugucgg uaccgucuat t                                              21

<210> SEQ ID NO 277
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 277
uugccgcauc aaaggugac                                                 19

<210> SEQ ID NO 278
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 278
uugccgcauc aaaggugact t                                              21

<210> SEQ ID NO 279
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 279
gucaccuuug augcggcaat t                                              21

<210> SEQ ID NO 280
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 280
aacuacaucg aucauggag                                                 19

<210> SEQ ID NO 281
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 281
aacuacaucg aucauggagt t                                              21

<210> SEQ ID NO 282
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 282
cuccaugauc gauguaguut t                                              21

<210> SEQ ID NO 283
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 283
uuuggcggau ugcauuccu                                                 19

<210> SEQ ID NO 284
<211> LENGTH: 21
<212> TYPE: DNA
<213> ORGANISM: Artificial Sequence
<220> FEATURE:

<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 284
uuuggcggau ugcauuccut t                                              21

<210> SEQ ID NO 285
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 285
aggaaugcaa uccgccaaat t                                              21

<210> SEQ ID NO 286
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 286
gcuuuagucg agaaccaau                                                 19

<210> SEQ ID NO 287
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 287
gcuuuagucg agaaccaaut t                                              21

<210> SEQ ID NO 288
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 288
auugguucuc gacuaaagct t                                              21

<210> SEQ ID NO 289
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

```
<400> SEQUENCE: 289
uuuagucgag aaccaauga                                              19

<210> SEQ ID NO 290
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 290
uuuagucgag aaccaaugat t                                           21

<210> SEQ ID NO 291
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 291
ucauugguuc ucgacuaaat t                                           21

<210> SEQ ID NO 292
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 292
uagucgagaa ccaaugaug                                              19

<210> SEQ ID NO 293
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 293
uagucgagaa ccaaugaugt t                                           21

<210> SEQ ID NO 294
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 294
caucauuggu ucucgacuat t                                           21
```

<210> SEQ ID NO 295
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 295
aagugucuac ccaguugaa                                              19

<210> SEQ ID NO 296
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 296
aagugucuac ccaguugaat t                                           21

<210> SEQ ID NO 297
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 297
uucaacuggg uagacacuut t                                           21

<210> SEQ ID NO 298
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 298
ucaguuacgg guuaauuac                                              19

<210> SEQ ID NO 299
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 299
ucaguuacgg guuaauuact t                                           21

<210> SEQ ID NO 300
<211> LENGTH: 21
<212> TYPE: DNA
<213> ORGANISM: Artificial Sequence

```
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 300
guaauuaacc cguaacugat t                                               21

<210> SEQ ID NO 301
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 301
uuacggguua auuacuguc                                                  19

<210> SEQ ID NO 302
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 302
uuacggguua auuacuguct t                                               21

<210> SEQ ID NO 303
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 303
gacaguaauu aacccguaat t                                               21

<210> SEQ ID NO 304
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 304
uacgggguaa uuacugucu                                                  19

<210> SEQ ID NO 305
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin
```

```
<400> SEQUENCE: 305
uacggguuaa uuacugucut t                                              21

<210> SEQ ID NO 306
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 306
agacaguaau uaacccguat t                                              21

<210> SEQ ID NO 307
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 307
gucucgacag auagcugac                                                 19

<210> SEQ ID NO 308
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 308
gucucgacag auagcugact t                                              21

<210> SEQ ID NO 309
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 309
gucagcuauc ugucgagact t                                              21

<210> SEQ ID NO 310
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 310
ucucgacaga uagcugaca                                                 19
```

-continued

<210> SEQ ID NO 311
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 311
ucucgacaga uagcugacat t                                              21

<210> SEQ ID NO 312
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 312
ugucagcuau cugucgagat t                                              21

<210> SEQ ID NO 313
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 313
ugcgggcucg uuccaugau                                                 19

<210> SEQ ID NO 314
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 314
ugcgggcucg uuccaugaut t                                              21

<210> SEQ ID NO 315
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 315
aucauggaac gagcccgcat t                                              21

<210> SEQ ID NO 316
<211> LENGTH: 19
<212> TYPE: RNA

```
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 316
uucagucucg uugugaaaa                                                    19

<210> SEQ ID NO 317
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 317
uucagucucg uugugaaaat t                                                 21

<210> SEQ ID NO 318
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 318
uuuucacaac gagacugaat t                                                 21

<210> SEQ ID NO 319
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 319
ugucgccggg uagaaaugc                                                    19

<210> SEQ ID NO 320
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 320
ugucgccggg uagaaaugct t                                                 21

<210> SEQ ID NO 321
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
```

Synthetic siRNA sequence specific for huntingtin

<400> SEQUENCE: 321
gcauuucuac ccggcgacat t                                              21

<210> SEQ ID NO 322
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 322
ucggaguuca accuaagcc                                                 19

<210> SEQ ID NO 323
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 323
ucggaguuca accuaagcct t                                              21

<210> SEQ ID NO 324
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 324
ggcuuagguu gaacuccgat t                                              21

<210> SEQ ID NO 325
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 325
caugcuuaag ccuagggau                                                 19

<210> SEQ ID NO 326
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 326
caugcuuaag ccuagggaut t                                              21

<210> SEQ ID NO 327
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 327
aucccuaggc uuaagcaugt t                                           21

<210> SEQ ID NO 328
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 328
ccgcugaguc uggaucucc                                              19

<210> SEQ ID NO 329
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 329
ccgcugaguc uggaucucct t                                           21

<210> SEQ ID NO 330
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 330
ggagauccag acucagcggt t                                           21

<210> SEQ ID NO 331
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 331
ugucaacagc uacacacgu                                              19

<210> SEQ ID NO 332
<211> LENGTH: 21
<212> TYPE: DNA
<213> ORGANISM: Artificial Sequence
<220> FEATURE:

<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 332
ugucaacagc uacacacgut t                                                   21

<210> SEQ ID NO 333
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 333
acguguguag cguugacat t                                                    21

<210> SEQ ID NO 334
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 334
guggccggca acccagcug                                                      19

<210> SEQ ID NO 335
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 335
guggccggca acccagcugt t                                                   21

<210> SEQ ID NO 336
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 336 cagcugggu gccggccact t                                                    21

<210> SEQ ID NO 337
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

```
<400> SEQUENCE: 337
gaaagggauc gcccacugc                                                19

<210> SEQ ID NO 338
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 338
gaaagggauc gcccacugct t                                             21

<210> SEQ ID NO 339
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 339
gcagugggcg aucccuuuct t                                             21

<210> SEQ ID NO 340
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 340
aaagggaucg cccacugcg                                                19

<210> SEQ ID NO 341
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 341
aaagggaucg cccacugcgt t                                             21

<210> SEQ ID NO 342
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 342
cgcagugggc gaucccuuut t                                             21
```

```
<210> SEQ ID NO 343
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 343
cggguagaac uucagaccc                                                  19

<210> SEQ ID NO 344
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 344
cggguagaac uucagaccct t                                               21

<210> SEQ ID NO 345
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 345
gggucugaag uucuacccgt t                                               21

<210> SEQ ID NO 346
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 346
gcucgaccgc agggccuuc                                                  19

<210> SEQ ID NO 347
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 347
gcucgaccgc agggccuuct t                                               21

<210> SEQ ID NO 348
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 348
gaaggcccug cggucgagct t                                             21

<210> SEQ ID NO 349
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 349
agcccauauc accggcugc                                                19

<210> SEQ ID NO 350
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 350
agcccauauc accggcugct t                                             21

<210> SEQ ID NO 351
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 351
gcagccggug auaugggcut t                                             21

<210> SEQ ID NO 352
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 352
uucuaugccc guguaaagu                                                19

<210> SEQ ID NO 353
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin
```

<400> SEQUENCE: 353
uucuaugccc guguaaagut t                                        21

<210> SEQ ID NO 354
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 354
acuuuacacg ggcauagaat t                                        21

<210> SEQ ID NO 355
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 355
cccuuuuagu caggagagu                                           19

<210> SEQ ID NO 356
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 356
cccuuuuagu caggagagut t                                        21

<210> SEQ ID NO 357
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 357
acucuccuga cuaaaagggt t                                        21

<210> SEQ ID NO 358
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 358
gguuggcgac ugucaugug                                           19

```
<210> SEQ ID NO 359
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 359
gguuggcgac ugucaugugt t                                              21

<210> SEQ ID NO 360
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 360
cacaugacag ucgccaacct t                                              21

<210> SEQ ID NO 361
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 361
acugucucga cagauagcu                                                 19

<210> SEQ ID NO 362
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 362
acugucucga cagauagcut t                                              21

<210> SEQ ID NO 363
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 363
agcuaucugu cgagacagut t                                              21

<210> SEQ ID NO 364
<211> LENGTH: 19
<212> TYPE: RNA
```

-continued

```
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 364
uugucugaca auaugugaa                                                19

<210> SEQ ID NO 365
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 365
uugucugaca auaugugaat t                                             21

<210> SEQ ID NO 366
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 366
uucacauauu gucagacaat t                                             21

<210> SEQ ID NO 367
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 367
cugggcaucg cuauggaac                                                19

<210> SEQ ID NO 368
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 368
cugggcaucg cuauggaact t                                             21

<210> SEQ ID NO 369
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
```

-continued

Synthetic siRNA sequence specific for huntingtin

<400> SEQUENCE: 369
guuccauagc gaugcccagt t                                           21

<210> SEQ ID NO 370
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 370
cucggaguuu gcgugcugc                                              19

<210> SEQ ID NO 371
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 371
cucggaguuu gcgugcugct t                                           21

<210> SEQ ID NO 372
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 372
gcagcacgca aacuccgagt t                                           21

<210> SEQ ID NO 373
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 373
uguuaaaggc cuucauagc                                              19

<210> SEQ ID NO 374
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 374
uguuaaaggc cuucauagct t                                           21

<210> SEQ ID NO 375
<211> LENGTH: 21
<212> TYPE: DNA
<213> ORGANISM: Artificial Sequence
<220> FEATURE:
<223> OTHER INFORMATION: Description of Artificial Sequence: Synthetic
siRNA sequence specific for huntingtin
<220> FEATURE:
<223> OTHER INFORMATION: Description of Combined DNA/RNA Molecule:
Synthetic siRNA sequence specific for huntingtin

<400> SEQUENCE: 375
gcuaugaagg ccuuuaacat t                                              21

<210> SEQ ID NO 376
<211> LENGTH: 19
<212> TYPE: RNA
<213> ORGANISM: Artificial Sequence
<220> FEATURE:
<223> OTHER INFORMATION: Description of Artificial Sequence: Synthetic
siRNA sequence specific for huntingtin

<400> SEQUENCE: 376
uuaaaggccu ucauagcga                                                 19

<210> SEQ ID NO 377
<211> LENGTH: 21
<212> TYPE: DNA
<213> ORGANISM: Artificial Sequence
<220> FEATURE:
<223> OTHER INFORMATION: Description of Artificial Sequence: Synthetic
siRNA sequence specific for huntingtin
<220> FEATURE:
<223> OTHER INFORMATION: Description of Combined DNA/RNA Molecule:
Synthetic siRNA sequence specific for huntingtin

<400> SEQUENCE: 377
uuaaaggccu ucauagcgat t                                              21

<210> SEQ ID NO 378
<211> LENGTH: 21
<212> TYPE: DNA
<213> ORGANISM: Artificial Sequence
<220> FEATURE:
<223> OTHER INFORMATION: Description of Artificial Sequence: Synthetic
siRNA sequence specific for huntingtin
<220> FEATURE:
<223> OTHER INFORMATION: Description of Combined DNA/RNA Molecule:
Synthetic siRNA sequence specific for huntingtin

<400> SEQUENCE: 378
ucgcuaugaa ggccuuuaat t                                              21

<210> SEQ ID NO 379
<211> LENGTH: 19
<212> TYPE: RNA
<213> ORGANISM: Artificial Sequence
<220> FEATURE:
<223> OTHER INFORMATION: Description of Artificial Sequence: Synthetic
siRNA sequence specific for huntingtin

<400> SEQUENCE: 379
gccuucauag cgaaccuga                                                 19

<210> SEQ ID NO 380
<211> LENGTH: 21
<212> TYPE: DNA
<213> ORGANISM: Artificial Sequence
<220> FEATURE:

```
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 380
gccuucauag cgaaccugat t                                              21

<210> SEQ ID NO 381
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 381
ucagguucgc uaugaaggct t                                              21

<210> SEQ ID NO 382
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 382
aaggcagcuu cggagugac                                                 19

<210> SEQ ID NO 383
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 383
aaggcagcuu cggagugact t                                              21

<210> SEQ ID NO 384
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 384
gucacuccga agcugccuut t                                              21

<210> SEQ ID NO 385
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin
```

```
<400> SEQUENCE: 385
agguuuauga acugacguu                                                19

<210> SEQ ID NO 386
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 386
agguuuauga acugacguut t                                             21

<210> SEQ ID NO 387
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 387
aacgucaguu cauaaaccut t                                             21

<210> SEQ ID NO 388
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 388
aacugacguu acaucauac                                                19

<210> SEQ ID NO 389
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 389
aacugacguu acaucauact t                                             21

<210> SEQ ID NO 390
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 390
guaugaugua acgucaguut t                                             21
```

```
<210> SEQ ID NO 391
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 391
cacaauguug ugaccggag                                                  19

<210> SEQ ID NO 392
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 392
cacaauguug ugaccggagt t                                               21

<210> SEQ ID NO 393
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 393
cuccggucac aacauugugt t                                               21

<210> SEQ ID NO 394
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 394
caauguugug accggagcc                                                  19

<210> SEQ ID NO 395
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 395
caauguugug accggagcct t                                               21

<210> SEQ ID NO 396
<211> LENGTH: 21
<212> TYPE: DNA
<213> ORGANISM: Artificial Sequence
```

```
-continued
```

<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 396
ggcuccgguc acaacauugt t                                                21

<210> SEQ ID NO 397
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 397
agcagcucuu cagaacgcc                                                   19

<210> SEQ ID NO 398
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 398
agcagcucuu cagaacgcct t                                                21

<210> SEQ ID NO 399
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 399
ggcguucuga agagcugcut t                                                21

<210> SEQ ID NO 400
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 400
guggccgaag ccguagugg                                                   19

<210> SEQ ID NO 401
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 401
guggccgaag ccguaguggt t                                              21

<210> SEQ ID NO 402
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 402
ccacuacggc uucggccact t                                              21

<210> SEQ ID NO 403
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 403
cguaguggga guauugugg                                                 19

<210> SEQ ID NO 404
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 404
cguaguggga guauuguggt t                                              21

<210> SEQ ID NO 405
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 405
ccacaauacu cccacuacgt t                                              21

<210> SEQ ID NO 406
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 406
ggaguauugu ggaacuuau                                                 19

```
<210> SEQ ID NO 407
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 407
ggaguauugu ggaacuuaut t                                             21

<210> SEQ ID NO 408
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 408
auaaguucca caauacucct t                                             21

<210> SEQ ID NO 409
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 409
aguauugugg aacuuauag                                                19

<210> SEQ ID NO 410
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 410
aguauugugg aacuuauagt t                                             21

<210> SEQ ID NO 411
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 411
cuauaaguuc cacaauacut t                                             21

<210> SEQ ID NO 412
<211> LENGTH: 19
<212> TYPE: RNA
```

```
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 412
gagaucggau gucagcagc                                                    19

<210> SEQ ID NO 413
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 413
gagaucggau gucagcagct t                                                 21

<210> SEQ ID NO 414
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 414
gcugcugaca uccgaucuct t                                                 21

<210> SEQ ID NO 415
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 415
cagcgccguc ccaucugac                                                    19

<210> SEQ ID NO 416
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 416
cagcgccguc ccaucugact t                                                 21

<210> SEQ ID NO 417
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
```

Synthetic siRNA sequence specific for huntingtin

<400> SEQUENCE: 417
gucagauggg acggcgcugt t      21

<210> SEQ ID NO 418
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 418
ccaccgaagg gccugauuc      19

<210> SEQ ID NO 419
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 419
ccaccgaagg gccugauuct t      21

<210> SEQ ID NO 420
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 420
gaaucaggcc cuucgguggt t      21

<210> SEQ ID NO 421
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 421
auuguguuag acgguaccg      19

<210> SEQ ID NO 422
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 422
auuguguuag acgguaccgt t      21

<210> SEQ ID NO 423
<211> LENGTH: 21
<212> TYPE: DNA
<213> ORGANISM: Artificial Sequence
<220> FEATURE:
<223> OTHER INFORMATION: Description of Artificial Sequence: Synthetic siRNA sequence specific for huntingtin
<220> FEATURE:
<223> OTHER INFORMATION: Description of Combined DNA/RNA Molecule: Synthetic siRNA sequence specific for huntingtin

<400> SEQUENCE: 423
cgguaccguc uaacacaaut t                                              21

<210> SEQ ID NO 424
<211> LENGTH: 19
<212> TYPE: RNA
<213> ORGANISM: Artificial Sequence
<220> FEATURE:
<223> OTHER INFORMATION: Description of Artificial Sequence: Synthetic siRNA sequence specific for huntingtin

<400> SEQUENCE: 424
ccgacaacca guauuuggg                                                 19

<210> SEQ ID NO 425
<211> LENGTH: 21
<212> TYPE: DNA
<213> ORGANISM: Artificial Sequence
<220> FEATURE:
<223> OTHER INFORMATION: Description of Artificial Sequence: Synthetic siRNA sequence specific for huntingtin
<220> FEATURE:
<223> OTHER INFORMATION: Description of Combined DNA/RNA Molecule: Synthetic siRNA sequence specific for huntingtin

<400> SEQUENCE: 425
ccgacaacca guauugggt t                                               21

<210> SEQ ID NO 426
<211> LENGTH: 21
<212> TYPE: DNA
<213> ORGANISM: Artificial Sequence
<220> FEATURE:
<223> OTHER INFORMATION: Description of Artificial Sequence: Synthetic siRNA sequence specific for huntingtin
<220> FEATURE:
<223> OTHER INFORMATION: Description of Combined DNA/RNA Molecule: Synthetic siRNA sequence specific for huntingtin

<400> SEQUENCE: 426
cccaaauacu gguugucggt t                                              21

<210> SEQ ID NO 427
<211> LENGTH: 19
<212> TYPE: RNA
<213> ORGANISM: Artificial Sequence
<220> FEATURE:
<223> OTHER INFORMATION: Description of Artificial Sequence: Synthetic siRNA sequence specific for huntingtin

<400> SEQUENCE: 427
aaacaagccu ugccgcauc                                                 19

<210> SEQ ID NO 428
<211> LENGTH: 21
<212> TYPE: DNA
<213> ORGANISM: Artificial Sequence
<220> FEATURE:

<223> OTHER INFORMATION: Description of Artificial Sequence: Synthetic
       siRNA sequence specific for huntingtin
<220> FEATURE:
<223> OTHER INFORMATION: Description of Combined DNA/RNA Molecule:
       Synthetic siRNA sequence specific for huntingtin

<400> SEQUENCE: 428
aaacaagccu ugccgcauct t                                              21

<210> SEQ ID NO 429
<211> LENGTH: 21
<212> TYPE: DNA
<213> ORGANISM: Artificial Sequence
<220> FEATURE:
<223> OTHER INFORMATION: Description of Artificial Sequence: Synthetic
       siRNA sequence specific for huntingtin
<220> FEATURE:
<223> OTHER INFORMATION: Description of Combined DNA/RNA Molecule:
       Synthetic siRNA sequence specific for huntingtin

<400> SEQUENCE: 429
gaugcggcaa ggcuuguuut t                                              21

<210> SEQ ID NO 430
<211> LENGTH: 19
<212> TYPE: RNA
<213> ORGANISM: Artificial Sequence
<220> FEATURE:
<223> OTHER INFORMATION: Description of Artificial Sequence: Synthetic
       siRNA sequence specific for huntingtin
<220> FEATURE:
<223> OTHER INFORMATION: Description of Combined DNA/RNA Molecule:
       Synthetic siRNA sequence specific for huntingtin

<400> SEQUENCE: 430
gccuugccgc aucaaaggu                                                 19

<210> SEQ ID NO 431
<211> LENGTH: 21
<212> TYPE: DNA
<213> ORGANISM: Artificial Sequence
<220> FEATURE:
<223> OTHER INFORMATION: Description of Artificial Sequence: Synthetic
       siRNA sequence specific for huntingtin

<400> SEQUENCE: 431
gccuugccgc aucaaaggut t                                              21

<210> SEQ ID NO 432
<211> LENGTH: 21
<212> TYPE: DNA
<213> ORGANISM: Artificial Sequence
<220> FEATURE:
<223> OTHER INFORMATION: Description of Artificial Sequence: Synthetic
       siRNA sequence specific for huntingtin
<220> FEATURE:
<223> OTHER INFORMATION: Description of Combined DNA/RNA Molecule:
       Synthetic siRNA sequence specific for huntingtin

<400> SEQUENCE: 432
accuuugaug cggcaaggct t                                              21

<210> SEQ ID NO 433
<211> LENGTH: 19
<212> TYPE: RNA
<213> ORGANISM: Artificial Sequence
<220> FEATURE:
<223> OTHER INFORMATION: Description of Artificial Sequence: Synthetic
       siRNA sequence specific for huntingtin

```
<400> SEQUENCE: 433
aucuugaacu acaucgauc                                                    19

<210> SEQ ID NO 434
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 434
aucuugaacu acaucgauct t                                                 21

<210> SEQ ID NO 435
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 435
gaucgaugua guucaagaut t                                                 21

<210> SEQ ID NO 436
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 436
aucgaucaug gagacccac                                                    19

<210> SEQ ID NO 437
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 437
aucgaucaug gagacccact t                                                 21

<210> SEQ ID NO 438
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 438
gugggucucc augaucgaut t                                                 21
```

```
<210> SEQ ID NO 439
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 439
uggagaccca cagguucga                                                      19

<210> SEQ ID NO 440
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 440
uggagaccca cagguucgat t                                                   21

<210> SEQ ID NO 441
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 441
ucgaaccugu gggucuccat t                                                   21

<210> SEQ ID NO 442
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 442
ggagacccac agguucgag                                                      19

<210> SEQ ID NO 443
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 443
ggagacccac agguucgagt t                                                   21

<210> SEQ ID NO 444
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 444
cucgaaccug ugggucucct t                                              21

<210> SEQ ID NO 445
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 445
ccgcuuccac gugggagau                                                 19

<210> SEQ ID NO 446
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 446
ccgcuuccac gugggagaut t                                              21

<210> SEQ ID NO 447
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 447
aucucccacg uggaagcggt t                                              21

<210> SEQ ID NO 448
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 448
ucuuuggcgg auugcauuc                                                 19

<210> SEQ ID NO 449
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin
```

```
<400> SEQUENCE: 449
ucuuuggcgg auugcauuct t                                              21

<210> SEQ ID NO 450
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 450
gaaugcaauc cgccaaagat t                                              21

<210> SEQ ID NO 451
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 451
uuggcggauu gcauuccuu                                                 19

<210> SEQ ID NO 452
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 452
uuggcggauu gcauuccuut t                                              21

<210> SEQ ID NO 453
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 453
aaggaaugca auccgccaat t                                              21

<210> SEQ ID NO 454
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 454
agcagcuaca gugaguuag                                                 19
```

```
<210> SEQ ID NO 455
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 455
agcagcuaca gugaguuagt t                                              21

<210> SEQ ID NO 456
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 456
cuaacucacu guagcugcut t                                              21

<210> SEQ ID NO 457
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 457
cgagugcuca auaauguug                                                 19

<210> SEQ ID NO 458
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 458
cgagugcuca auaauguugt t                                              21

<210> SEQ ID NO 459
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 459
caacauuauu gagcacucgt t                                              21

<210> SEQ ID NO 460
<211> LENGTH: 19
<212> TYPE: RNA
```

```
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 460
aauuaggcuu gucccaaag                                                   19

<210> SEQ ID NO 461
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 461
aauuaggcuu gucccaaagt t                                                21

<210> SEQ ID NO 462
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 462 cuugggaca agccuaauut t                                                 21

<210> SEQ ID NO 463
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 463
uggaguuuag guuggcacu                                                   19

<210> SEQ ID NO 464
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 464
uggaguuuag guuggcacut t                                                21

<210> SEQ ID NO 465
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
```

```
                Synthetic siRNA sequence specific for huntingtin

<400> SEQUENCE: 465
agugccaacc uaaacuccat t                                              21

<210> SEQ ID NO 466
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 466
cuugguuccc auuggaucu                                                 19

<210> SEQ ID NO 467
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 467
cuugguuccc auuggaucut t                                              21

<210> SEQ ID NO 468
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 468
agauccaaug ggaaccaagt t                                              21

<210> SEQ ID NO 469
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 469
uuuuggccgg aaacuugcu                                                 19

<210> SEQ ID NO 470
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 470
uuuuggccgg aaacuugcut t                                              21
```

```
<210> SEQ ID NO 471
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 471
agcaaguuuc cggccaaaat t                                            21

<210> SEQ ID NO 472
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 472
ugccuucucu aacaaaccc                                               19

<210> SEQ ID NO 473
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 473
ugccuucucu aacaaaccct t                                            21

<210> SEQ ID NO 474
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 474
ggguuuguua gagaaggcat t                                            21

<210> SEQ ID NO 475
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 475
uaagucccau ccgacgaaa                                               19

<210> SEQ ID NO 476
<211> LENGTH: 21
<212> TYPE: DNA
<213> ORGANISM: Artificial Sequence
<220> FEATURE:
```

<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 476
uaagucccau ccgacgaaat t                                          21

<210> SEQ ID NO 477
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 477
uuucgucgga ugggacuuat t                                          21

<210> SEQ ID NO 478
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 478
ugauaccuca gguccuguu                                             19

<210> SEQ ID NO 479
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 479
ugauaccuca gguccuguut t                                          21

<210> SEQ ID NO 480
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 480
aacaggaccu gagguaucat t                                          21

<210> SEQ ID NO 481
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

```
<400> SEQUENCE: 481
gauaccucag guccuguua                                                 19

<210> SEQ ID NO 482
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 482
gauaccucag guccuguuat t                                              21

<210> SEQ ID NO 483
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 483
uaacaggacc ugagguauct t                                              21

<210> SEQ ID NO 484
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 484
uguuacaaca aguaaaucc                                                 19

<210> SEQ ID NO 485
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 485
uguuacaaca aguaaaucct t                                              21

<210> SEQ ID NO 486
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 486
ggauuuacuu guuguaacat t                                              21
```

```
<210> SEQ ID NO 487
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 487
cuaggauacc ugaaauccu                                                 19

<210> SEQ ID NO 488
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 488
cuaggauacc ugaaauccut t                                              21

<210> SEQ ID NO 489
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 489
aggauuucag guauccuagt t                                              21

<210> SEQ ID NO 490
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 490
cuuuagucga gaaccaaug                                                 19

<210> SEQ ID NO 491
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 491
cuuuagucga gaaccaaugt t                                              21

<210> SEQ ID NO 492
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 492
cauugguucu cgacuaaagt t                                          21

<210> SEQ ID NO 493
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 493
acuguuugug uucaacaau                                             19

<210> SEQ ID NO 494
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 494
acuguuugug uucaacaaut t                                          21

<210> SEQ ID NO 495
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 495
auuguugaac acaaacagut t                                          21

<210> SEQ ID NO 496
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 496
caauuguuga agacucucu                                             19

<210> SEQ ID NO 497
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin
```

```
<400> SEQUENCE: 497
caauuguuga agacucucut t                                              21

<210> SEQ ID NO 498
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 498
agagagucuu caacaauugt t                                              21

<210> SEQ ID NO 499
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 499
caagucacaa ggccgagca                                                 19

<210> SEQ ID NO 500
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 500
caagucacaa ggccgagcat t                                              21

<210> SEQ ID NO 501
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 501
ugcucggccu ugugacuugt t                                              21

<210> SEQ ID NO 502
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 502
aagucacaag gccgagcac                                                 19
```

```
<210> SEQ ID NO 503
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 503
aagucacaag gccgagcact t                                            21

<210> SEQ ID NO 504
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 504
gugcucggcc uugugacuut t                                            21

<210> SEQ ID NO 505
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 505
ggcuuguacc acuacugcu                                               19

<210> SEQ ID NO 506
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 506
ggcuuguacc acuacugcut t                                            21

<210> SEQ ID NO 507
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 507
agcaguagug guacaagcct t                                            21

<210> SEQ ID NO 508
<211> LENGTH: 19
<212> TYPE: RNA
```

```
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 508
acgacaccuc gggaugguu                                                      19

<210> SEQ ID NO 509
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 509
acgacaccuc gggaugguut t                                                   21

<210> SEQ ID NO 510
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 510
aaccaucccg aggugucgut t                                                   21

<210> SEQ ID NO 511
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 511
caccucggga ugguuugau                                                      19

<210> SEQ ID NO 512
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 512
caccucggga ugguuugaut t                                                   21

<210> SEQ ID NO 513
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
```

Synthetic siRNA sequence specific for huntingtin

<400> SEQUENCE: 513
aucaaaccau cccgaggugt t                                              21

<210> SEQ ID NO 514
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 514
cucgggaugg uuugauguc                                                 19

<210> SEQ ID NO 515
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 515
cucgggaugg uuugauguct t                                              21

<210> SEQ ID NO 516
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 516
gacaucaaac caucccgagt t                                              21

<210> SEQ ID NO 517
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 517
agugucacaa agaaccgug                                                 19

<210> SEQ ID NO 518
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 518
agugucacaa agaaccgugt t                                              21

<210> SEQ ID NO 519
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 519
cacgguucuu ugugacacut t                                              21

<210> SEQ ID NO 520
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 520
gugucacaaa gaaccgugc                                                 19

<210> SEQ ID NO 521
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 521
gugucacaaa gaaccgugct t                                              21

<210> SEQ ID NO 522
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 522
gcacgguucu uugugacact t                                              21

<210> SEQ ID NO 523
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 523
aaccgugcag auaagaaug                                                 19

<210> SEQ ID NO 524
<211> LENGTH: 21
<212> TYPE: DNA
<213> ORGANISM: Artificial Sequence
<220> FEATURE:

```
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 524
aaccgugcag auaagaaugt t                                              21

<210> SEQ ID NO 525
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 525
cauucuuauc ugcacgguut t                                              21

<210> SEQ ID NO 526
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 526
accgugcaga uaagaaugc                                                 19

<210> SEQ ID NO 527
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 527
accgugcaga uaagaaugct t                                              21

<210> SEQ ID NO 528
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 528
gcauucuuau cugcacgguut t                                             21

<210> SEQ ID NO 529
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin
```

```
<400> SEQUENCE: 529
ccgugcagau aagaaugcu                                                    19

<210> SEQ ID NO 530
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 530
ccgugcagau aagaaugcut t                                                 21

<210> SEQ ID NO 531
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 531
agcauucuua ucugcacggt t                                                 21

<210> SEQ ID NO 532
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 532
gcagauaaga augcuauuc                                                    19

<210> SEQ ID NO 533
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 533
gcagauaaga augcuauuct t                                                 21

<210> SEQ ID NO 534
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 534
gaauagcauu cuuaucugct t                                                 21
```

<210> SEQ ID NO 535
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 535
acauucguuu guuugaacc                                                   19

<210> SEQ ID NO 536
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 536
acauucguuu guuugaacct t                                                21

<210> SEQ ID NO 537
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 537
gguucaaaca aacgaaugut t                                                21

<210> SEQ ID NO 538
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 538
ugaaccucuu guuauaaaa                                                   19

<210> SEQ ID NO 539
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 539
ugaaccucuu guuauaaaat t                                                21

<210> SEQ ID NO 540
<211> LENGTH: 21
<212> TYPE: DNA
<213> ORGANISM: Artificial Sequence

```
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 540
uuuuauaaca agagguucat t                                              21

<210> SEQ ID NO 541
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 541
uuuagauuug cuggcgcag                                                 19

<210> SEQ ID NO 542
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 542
uuuagauuug cuggcgcagt t                                              21

<210> SEQ ID NO 543
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 543
cugcgccagc aaaucuaaat t                                              21

<210> SEQ ID NO 544
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 544
ugguucaguu acggguuaa                                                 19

<210> SEQ ID NO 545
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin
```

```
<400> SEQUENCE: 545
ugguucaguu acgguuaat t                                          21

<210> SEQ ID NO 546
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 546
uuaacccgua acugaaccat t                                         21

<210> SEQ ID NO 547
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 547
gggccaguuc agggaauca                                            19

<210> SEQ ID NO 548
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 548
gggccaguuc agggaaucat t                                         21

<210> SEQ ID NO 549
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 549 ugauuccug aacuggccct t                                          21

<210> SEQ ID NO 550
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 550
uggaagcgac ugucucgac                                            19
```

```
<210> SEQ ID NO 551
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 551
uggaagcgac ugucucgact t                                              21

<210> SEQ ID NO 552
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 552
gucgagacag ucgcuuccat t                                              21

<210> SEQ ID NO 553
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 553
ggaagcgacu gucucgaca                                                 19

<210> SEQ ID NO 554
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 554
ggaagcgacu gucucgacat t                                              21

<210> SEQ ID NO 555
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 555
ugucgagaca gucgcuucct t                                              21

<210> SEQ ID NO 556
<211> LENGTH: 19
<212> TYPE: RNA
```

```
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 556
gaagcgacug ucucgacag                                                  19

<210> SEQ ID NO 557
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 557
gaagcgacug ucucgacagt t                                               21

<210> SEQ ID NO 558
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 558
cugucgagac agucgcuuct t                                               21

<210> SEQ ID NO 559
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 559
gcgacugucu cgacagaua                                                  19

<210> SEQ ID NO 560
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 560
gcgacugucu cgacagauat t                                               21

<210> SEQ ID NO 561
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
```

Synthetic siRNA sequence specific for huntingtin

<400> SEQUENCE: 561
uaucugucga gacagucgct t                                             21

<210> SEQ ID NO 562
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 562
ugucucgaca gauagcuga                                                19

<210> SEQ ID NO 563
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 563
ugucucgaca gauagcugat t                                             21

<210> SEQ ID NO 564
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 564
ucagcuaucu gucgagacat t                                             21

<210> SEQ ID NO 565
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 565
cucgacagau agcugacau                                                19

<210> SEQ ID NO 566
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 566
cucgacagau agcugacaut t                                             21

```
<210> SEQ ID NO 567
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 567
augucagcua ucugucgagt t                                           21

<210> SEQ ID NO 568
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 568
agguggaaau gagugagca                                              19

<210> SEQ ID NO 569
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 569
agguggaaau gagugagcat t                                           21

<210> SEQ ID NO 570
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 570
ugcucacuca uuuccaccut t                                           21

<210> SEQ ID NO 571
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 571
agugagcagc aacauacuu                                              19

<210> SEQ ID NO 572
<211> LENGTH: 21
<212> TYPE: DNA
<213> ORGANISM: Artificial Sequence
<220> FEATURE:
```

<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 572
agugagcagc aacauacuut t                                              21

<210> SEQ ID NO 573
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 573
aaguauguug cugcucacut t                                              21

<210> SEQ ID NO 574
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 574
guuccgcagu gauggcugu                                                 19

<210> SEQ ID NO 575
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 575
guuccgcagu gauggcugut t                                              21

<210> SEQ ID NO 576
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 576
acagccauca cugcggaact t                                              21

<210> SEQ ID NO 577
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

```
<400> SEQUENCE: 577
caaccacacc gacuaccgc                                                    19

<210> SEQ ID NO 578
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 578
caaccacacc gacuaccgct t                                                 21

<210> SEQ ID NO 579
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 579
gcgguagucg gugugguugt t                                                 21

<210> SEQ ID NO 580
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 580
aaccacaccg acuaccgcu                                                    19

<210> SEQ ID NO 581
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 581
aaccacaccg acuaccgcut t                                                 21

<210> SEQ ID NO 582
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 582
agcgguaguc gguguggut t                                                  21
```

```
<210> SEQ ID NO 583
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 583
accacaccga cuaccgcug                                                   19

<210> SEQ ID NO 584
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 584
accacaccga cuaccgcugt t                                                21

<210> SEQ ID NO 585
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 585
cagcgguagu cggugugghut t                                               21

<210> SEQ ID NO 586
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 586
cccgaaaaga cacagucug                                                   19

<210> SEQ ID NO 587
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 587
cccgaaaaga cacagucugt t                                                21

<210> SEQ ID NO 588
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 588
cagacugugu cuuuucgggt t                                            21

<210> SEQ ID NO 589
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 589
uccagcacaa aguuacuua                                               19

<210> SEQ ID NO 590
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 590
uccagcacaa aguuacuuat t                                            21

<210> SEQ ID NO 591
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 591
uaaguaacuu ugugcuggat t                                            21

<210> SEQ ID NO 592
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 592
uuggaaugug caauagaga                                               19

<210> SEQ ID NO 593
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin
```

```
<400> SEQUENCE: 593
uuggaaugug caauagagat t                                              21

<210> SEQ ID NO 594
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 594
ucucuauugc acauccaat t                                               21

<210> SEQ ID NO 595
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 595
agaucugauc agccuuucc                                                 19

<210> SEQ ID NO 596
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 596
agaucugauc agccuuucct t                                              21

<210> SEQ ID NO 597
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 597
ggaaaggcug aucagaucut t                                              21

<210> SEQ ID NO 598
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 598
caggcaauuc agucucguu                                                 19
```

```
<210> SEQ ID NO 599
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 599
caggcaauuc agucucguut t                                              21

<210> SEQ ID NO 600
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 600
aacgagacug aauugccugt t                                              21

<210> SEQ ID NO 601
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 601
ggcaauucag ucucguugu                                                 19

<210> SEQ ID NO 602
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 602
ggcaauucag ucucguugut t                                              21

<210> SEQ ID NO 603
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 603
acaacgagac ugaauugcct t                                              21

<210> SEQ ID NO 604
<211> LENGTH: 19
<212> TYPE: RNA
```

```
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 604
gcaauucagu cucguugug                                                        19

<210> SEQ ID NO 605
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 605
gcaauucagu cucguugugt t                                                     21

<210> SEQ ID NO 606
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 606
cacaacgaga cugaauugct t                                                     21

<210> SEQ ID NO 607
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 607
aauucagucu cguugugaa                                                        19

<210> SEQ ID NO 608
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 608
aauucagucu cguugugaat t                                                     21

<210> SEQ ID NO 609
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
```

Synthetic siRNA sequence specific for huntingtin

<400> SEQUENCE: 609
uucacaacga gacugaauut t                                              21

<210> SEQ ID NO 610
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 610
ucagucucgu ugugaaaac                                                 19

<210> SEQ ID NO 611
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 611
ucagucucgu ugugaaaact t                                              21

<210> SEQ ID NO 612
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 612
guuuucacaa cgagacugat t                                              21

<210> SEQ ID NO 613
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 613
aaaccuuuca acuccaacc                                                 19

<210> SEQ ID NO 614
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 614
aaaccuuuca acuccaacct t                                              21

<210> SEQ ID NO 615
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 615
gguuggaguu gaaagguuut t                                              21

<210> SEQ ID NO 616
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 616 cuuccgugu gcuggcucg                                                  19

<210> SEQ ID NO 617
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 617 cuuccgugu gcuggcucgt t                                               21

<210> SEQ ID NO 618
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 618
cgagccagca cacggaaagt t                                              21

<210> SEQ ID NO 619
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 619
ccgugugcug gcucgcaug                                                 19

<210> SEQ ID NO 620
<211> LENGTH: 21
<212> TYPE: DNA
<213> ORGANISM: Artificial Sequence
<220> FEATURE:

```
<223> OTHER INFORMATION: Description of Artificial Sequence: Synthetic
      siRNA sequence specific for huntingtin

<400> SEQUENCE: 620
ccgugugcug gcucgcaugt t                                              21

<210> SEQ ID NO 621
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 621
caugcgagcc agcacacggt t                                              21

<210> SEQ ID NO 622
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 622
ucgacauccu ugcuugucg                                                 19

<210> SEQ ID NO 623
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 623
ucgacauccu ugcuugucgt t                                              21

<210> SEQ ID NO 624
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 624
cgacaagcaa ggaugucgat t                                              21

<210> SEQ ID NO 625
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 625
ugcuugucgc cggguagaa                                                 19
```

-continued

<210> SEQ ID NO 626
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 626
ugcuugucgc cggguagaat t                                              21

<210> SEQ ID NO 627
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 627
uucuacccgg cgacaagcat t                                              21

<210> SEQ ID NO 628
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 628
gcuugucgcc ggguagaaa                                                 19

<210> SEQ ID NO 629
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 629
gcuugucgcc ggguagaaat t                                              21

<210> SEQ ID NO 630
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 630
uuucuacccg gcgacaagct t                                              21

<210> SEQ ID NO 631

```
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 631
cuugucgccg gguagaaau                                                    19

<210> SEQ ID NO 632
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 632
cuugucgccg gguagaaaut t                                                 21

<210> SEQ ID NO 633
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 633
auuucuaccc ggcgacaagt t                                                 21

<210> SEQ ID NO 634
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 634
ggcccaguug ccauggaa                                                     19

<210> SEQ ID NO 635
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 635
ggcccaguug ccauggaat t                                                  21

<210> SEQ ID NO 636
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
```

```
<220> FEATURE:
<223> OTHER INFORMATION: Description of Combined DNA/RNA Molecule:
      Synthetic siRNA sequence specific for huntingtin

<400> SEQUENCE: 636
uuccauuggc aacugggcct t                                              21

<210> SEQ ID NO 637
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 637
cagguuucgu cucuccacc                                                 19

<210> SEQ ID NO 638
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 638
cagguuucgu cucuccacct t                                              21

<210> SEQ ID NO 639
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 639
gguggagaga cgaaaccugt t                                              21

<210> SEQ ID NO 640
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 640
ggcacguguc acuggaaac                                                 19

<210> SEQ ID NO 641
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 641
```
ggcacguguc acuggaaact t         21

<210> SEQ ID NO 642
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 642
guuuccagug acacgugcct t         21

<210> SEQ ID NO 643
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 643
cuggaaacag ugaguccgg         19

<210> SEQ ID NO 644
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 644
cuggaaacag ugaguccggt t         21

<210> SEQ ID NO 645
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 645
ccggacucac uguuuccagt t         21

<210> SEQ ID NO 646
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 646
caaaucccag uguuggacc         19

<210> SEQ ID NO 647
<211> LENGTH: 21
<212> TYPE: DNA

```
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 647
caaaucccag uguuggacct t                                              21

<210> SEQ ID NO 648
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 648
gguccaacac uggauuugt t                                               21

<210> SEQ ID NO 649
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 649
acucggaguu caaccuaag                                                 19

<210> SEQ ID NO 650
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 650
acucggaguu caaccuaagt t                                              21

<210> SEQ ID NO 651
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 651
cuuagguuga acuccgagut t                                              21

<210> SEQ ID NO 652
<211> LENGTH: 19
<212> TYPE: RNA
<213> ORGANISM: Artificial Sequence
<220> FEATURE:
<223> OTHER INFORMATION: Description of Artificial Sequence: Synthetic
```

```
                            siRNA sequence specific for huntingtin

<400> SEQUENCE: 652
cucggaguuc aaccuaagc                                                    19

<210> SEQ ID NO 653
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 653
cucggaguuc aaccuaagct t                                                 21

<210> SEQ ID NO 654
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 654
gcuuagguug aacuccgagt t                                                 21

<210> SEQ ID NO 655
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 655
agccuaggga ugagugaaa                                                    19

<210> SEQ ID NO 656
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 656
agccuaggga ugagugaaat t                                                 21

<210> SEQ ID NO 657
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 657
```
uuucacucau cccuaggcut t                                              21

<210> SEQ ID NO 658
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 658
gucaacagcu acacacgug                                                 19

<210> SEQ ID NO 659
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 659
gucaacagcu acacacgugt t                                              21

<210> SEQ ID NO 660
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 660
cacgugugua gcuguugact t                                              21

<210> SEQ ID NO 661
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 661
gauggucacc caaaccggg                                                 19

<210> SEQ ID NO 662
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 662
gauggucacc caaaccgggt t                                              21

<210> SEQ ID NO 663
<211> LENGTH: 21

```
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 663
cccgguuugg gugaccauct t                                              21

<210> SEQ ID NO 664
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 664
ugacagaacu gcgaagggu                                                 19

<210> SEQ ID NO 665
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 665
ugacagaacu gcgaagggut t                                              21

<210> SEQ ID NO 666
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 666
acccuucgca guucugucat t                                              21

<210> SEQ ID NO 667
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 667
gaagacgaga uccucgcuc                                                 19

<210> SEQ ID NO 668
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
```

<223> OTHER INFORMATION: Description of Combined DNA/RNA Molecule:
      Synthetic siRNA sequence specific for huntingtin

<400> SEQUENCE: 668
gaagacgaga uccucgcuct t                                              21

<210> SEQ ID NO 669
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 669
gagcgaggau cucgucuuct t                                              21

<210> SEQ ID NO 670
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 670
acgagauccu cgcucagua                                                 19

<210> SEQ ID NO 671
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 671
acgagauccu cgcucaguat t                                              21

<210> SEQ ID NO 672
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 672
uacugagcga ggaucucgut t                                              21

<210> SEQ ID NO 673
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 673
aaccugaaag ggaucgccc                                                 19

<210> SEQ ID NO 674
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 674
aaccugaaag ggaucgccct t                                              21

<210> SEQ ID NO 675
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 675
gggcgauccc uuucagguut t                                              21

<210> SEQ ID NO 676
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 676
gaucgcccac ugcgugaac                                                 19

<210> SEQ ID NO 677
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 677
gaucgcccac ugcgugaact t                                              21

<210> SEQ ID NO 678
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 678
guucacgcag ugggcgauct t                                              21

<210> SEQ ID NO 679

```
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 679
cacugcguga acauucaca                                                       19

<210> SEQ ID NO 680
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 680
cacugcguga acauucacat t                                                    21

<210> SEQ ID NO 681
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 681
ugugaauguu cacgcagugt t                                                    21

<210> SEQ ID NO 682
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 682
agaacuaucc ucuggacgu                                                       19

<210> SEQ ID NO 683
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 683
agaacuaucc ucuggacgut t                                                    21

<210> SEQ ID NO 684
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
```

```
<220> FEATURE:
<223> OTHER INFORMATION: Description of Combined DNA/RNA Molecule:
      Synthetic siRNA sequence specific for huntingtin

<400> SEQUENCE: 684
acguccagag gauaguucut t                                              21

<210> SEQ ID NO 685
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 685
gucaguccgg guagaacuu                                                 19

<210> SEQ ID NO 686
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 686
gucaguccgg guagaacuut t                                              21

<210> SEQ ID NO 687
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 687
aaguucuacc cggacugact t                                              21

<210> SEQ ID NO 688
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 688
ugaacaaagu caucggaga                                                 19

<210> SEQ ID NO 689
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 689
```
ugaacaaagu caucggagat t                                              21

<210> SEQ ID NO 690
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 690
ucuccgauga cuuuguucat t                                              21

<210> SEQ ID NO 691
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 691
aagucaucgg agaguuucu                                                 19

<210> SEQ ID NO 692
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 692
aagucaucgg agaguuucut t                                              21

<210> SEQ ID NO 693
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 693
agaaacucuc cgaugacuut t                                              21

<210> SEQ ID NO 694
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 694
gucaucggag aguuucugu                                                 19

<210> SEQ ID NO 695
<211> LENGTH: 21
<212> TYPE: DNA

```
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic
      siRNA sequence specific for huntingtin

<400> SEQUENCE: 695
gucaucggag aguuucugut t                                          21

<210> SEQ ID NO 696
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 696
acagaaacuc uccgaugact t                                          21

<210> SEQ ID NO 697
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 697
ggccaccgug guguauaag                                             19

<210> SEQ ID NO 698
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 698
ggccaccgug guguauaagt t                                          21

<210> SEQ ID NO 699
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 699
cuuauacacc acgguggcct t                                          21

<210> SEQ ID NO 700
<211> LENGTH: 19
<212> TYPE: RNA
<213> ORGANISM: Artificial Sequence
<220> FEATURE:
```

-continued

<223> OTHER INFORMATION: Description of Artificial Sequence: Synthetic
      siRNA sequence specific for huntingtin

<400> SEQUENCE: 700
accguggugu auaaggugu                                                  19

<210> SEQ ID NO 701
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 701
accguggugu auaaggugut t                                               21

<210> SEQ ID NO 702
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 702
acaccuuaua caccacggut t                                               21

<210> SEQ ID NO 703
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 703
cugacuuguu uacgaaaug                                                  19

<210> SEQ ID NO 704
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 704
cugacuuguu uacgaaaugt t                                               21

<210> SEQ ID NO 705
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin -continued

```
<400> SEQUENCE: 705
cauuucguaa acaagucagt t                                              21

<210> SEQ ID NO 706
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 706
uguuuacgaa auguccaca                                                 19

<210> SEQ ID NO 707
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 707
uguuuacgaa auguccacat t                                              21

<210> SEQ ID NO 708
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 708
uguggacauu ucguaaacat t                                              21

<210> SEQ ID NO 709
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 709
ccaccgagcc agcuugguc                                                 19

<210> SEQ ID NO 710
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 710
ccaccgagcc agcuugguct t                                              21

<210> SEQ ID NO 711
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 711
gaccaagcug gcucgguggt t                                              21

<210> SEQ ID NO 712
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 712
caccgagcca gcuuggucc                                                 19

<210> SEQ ID NO 713
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 713
caccgagcca gcuuggucct t                                              21

<210> SEQ ID NO 714
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 714
ggaccaagcu ggcucggugt t                                              21

<210> SEQ ID NO 715
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 715
caggcaacgu gcgugucuc                                                 19

<210> SEQ ID NO 716
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
```

```
<220> FEATURE:
<223> OTHER INFORMATION: Description of Combined DNA/RNA Molecule:
      Synthetic siRNA sequence specific for huntingtin

<400> SEQUENCE: 716
caggcaacgu gcgugucuct t                                              21

<210> SEQ ID NO 717
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 717
gagacacgca cguugccugt t                                              21

<210> SEQ ID NO 718
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 718
aacgugcgug ucucugcca                                                 19

<210> SEQ ID NO 719
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 719
aacgugcgug ucucugccat t                                              21

<210> SEQ ID NO 720
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 720
uggcagagac acgcacguut t                                              21

<210> SEQ ID NO 721
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 721
```
uuaauuuuaa cguaacucu                                                    19

<210> SEQ ID NO 722
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 722
uuaauuuuaa cguaacucut t                                                 21

<210> SEQ ID NO 723
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 723
agaguuacgu uaaaauuaat t                                                 21

<210> SEQ ID NO 724
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 724
uuaacguaac ucuuucuau                                                    19

<210> SEQ ID NO 725
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 725
uuaacguaac ucuuucuaut t                                                 21

<210> SEQ ID NO 726
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 726
auagaaagag uuacguuaat t                                                 21

```
<210> SEQ ID NO 727
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 727
uaacguaacu cuuucuaug                                                    19

<210> SEQ ID NO 728
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 728
uaacguaacu cuuucuaugt t                                                 21

<210> SEQ ID NO 729
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 729
cauagaaaga guuacguuat t                                                 21

<210> SEQ ID NO 730
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 730
aacguaacuc uuucuaugc                                                    19

<210> SEQ ID NO 731
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 731
aacguaacuc uuucuaugct t                                                 21

<210> SEQ ID NO 732
<211> LENGTH: 21
<212> TYPE: DNA
<213> ORGANISM: Artificial Sequence
<220> FEATURE:
<223> OTHER INFORMATION: Description of Artificial Sequence: Synthetic
```

-continued siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 732
gcauagaaag aguuacguut t                                              21

<210> SEQ ID NO 733
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 733
guaacucuuu cuaugcccg                                                 19

<210> SEQ ID NO 734
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 734
guaacucuuu cuaugcccgt t                                              21

<210> SEQ ID NO 735
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 735
cgggcauaga aagaguuact t                                              21

<210> SEQ ID NO 736
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 736
uaugcccgug uaaaguaug                                                 19

<210> SEQ ID NO 737
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 737
uaugcccgug uaaaguaugt t                                        21

<210> SEQ ID NO 738
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 738
cauacuuuac acgggcauat t                                        21

<210> SEQ ID NO 739
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 739 ugcccguguaa aaguaugug                                          19

<210> SEQ ID NO 740
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 740
ugcccgugua aaguaugugt t                                        21

<210> SEQ ID NO 741
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 741
cacauacuuu acacgggcat t                                        21

<210> SEQ ID NO 742
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 742
ugagcacccg cugacauuu                                           19

<210> SEQ ID NO 743
<211> LENGTH: 21

```
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 743
ugagcacccg cugacauuut t                                              21

<210> SEQ ID NO 744
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 744
aaaugucagc gggugcucat t                                              21

<210> SEQ ID NO 745
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 745
cacccgcuga cauuccgu                                                  19

<210> SEQ ID NO 746
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 746
cacccgcuga cauuccgut t                                               21

<210> SEQ ID NO 747
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 747
acggaaaugu cagcgggugt t                                              21

<210> SEQ ID NO 748
<211> LENGTH: 19
<212> TYPE: RNA
<213> ORGANISM: Artificial Sequence
<220> FEATURE:
```

```
<223> OTHER INFORMATION: Description of Artificial Sequence: Synthetic
      siRNA sequence specific for huntingtin

<400> SEQUENCE: 748
uuuuagucag gagagugca                                                  19

<210> SEQ ID NO 749
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 749
uuuuagucag gagagugcat t                                               21

<210> SEQ ID NO 750
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 750
ugcacucucc ugacuaaaat t                                               21

<210> SEQ ID NO 751
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 751
agccaaguca uuaaaaugg                                                  19

<210> SEQ ID NO 752
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 752
agccaaguca uuaaaauggt t                                               21

<210> SEQ ID NO 753
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin
```

```
<400> SEQUENCE: 753
ccauuuuaau gacuuggcut t                                              21

<210> SEQ ID NO 754
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 754
guuggcgacu gucaugugg                                                 19

<210> SEQ ID NO 755
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 755
guuggcgacu gucauguggt t                                              21

<210> SEQ ID NO 756
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 756
ccacaugaca gucgccaact t                                              21

<210> SEQ ID NO 757
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 757
gcccuuaagg gaagcuacu                                                 19

<210> SEQ ID NO 758
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 758
gcccuuaagg gaagcuacut t                                              21

<210> SEQ ID NO 759
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 759
aguagcuucc cuuaagggct t                                              21

<210> SEQ ID NO 760
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 760
gcauaucgcu gggcucaac                                                 19

<210> SEQ ID NO 761
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 761
gcauaucgcu gggcucaact t                                              21

<210> SEQ ID NO 762
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 762
guugagccca gcgauaugct t                                              21

<210> SEQ ID NO 763
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 763
aauaugagcu cauuaguaa                                                 19

<210> SEQ ID NO 764
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
```

```
<220> FEATURE:
<223> OTHER INFORMATION: Description of Combined DNA/RNA Molecule:
      Synthetic siRNA sequence specific for huntingtin

<400> SEQUENCE: 764
aauaugagcu cauuaguaat t                                              21

<210> SEQ ID NO 765
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 765
uuacuaauga gcucauauut t                                              21

<210> SEQ ID NO 766
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 766
gugcccgugu cgguucuuc                                                 19

<210> SEQ ID NO 767
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 767
gugcccgugu cgguucuuct t                                              21

<210> SEQ ID NO 768
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 768
gaagaaccga cacgggcact t                                              21

<210> SEQ ID NO 769
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 769
```
aaugaaacca ggguagaau                                                19

<210> SEQ ID NO 770
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 770
aaugaaacca ggguagaaut t                                             21

<210> SEQ ID NO 771
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 771
auucuacccu gguuucauut t                                             21

<210> SEQ ID NO 772
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 772
cacccagaau guagcaucu                                                19

<210> SEQ ID NO 773
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 773
cacccagaau guagcaucut t                                             21

<210> SEQ ID NO 774
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 774
agaugcuaca uucugggugt t                                             21

<210> SEQ ID NO 775
<211> LENGTH: 19
<212> TYPE: RNA

```
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 775
gagcucggga cggauagua                                                   19

<210> SEQ ID NO 776
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 776
gagcucggga cggauaguat t                                                21

<210> SEQ ID NO 777
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 777
uacuauccgu cccgagcuct t                                                21

<210> SEQ ID NO 778
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 778
ugacaacuga aggcaaccu                                                   19

<210> SEQ ID NO 779
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 779
ugacaacuga aggcaaccut t                                                21

<210> SEQ ID NO 780
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
```

Synthetic siRNA sequence specific for huntingtin

<400> SEQUENCE: 780
agguugccuu caguugucat t					21

<210> SEQ ID NO 781
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 781
caacguggac cugccuacg					19

<210> SEQ ID NO 782
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 782
caacguggac cugccuacgt t					21

<210> SEQ ID NO 783
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 783
cguaggcagg uccacguugt t					21

<210> SEQ ID NO 784
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 784
gacugacgag agauguaua					19

<210> SEQ ID NO 785
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 785
gacugacgag agauguauat t					21

```
<210> SEQ ID NO 786
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 786
uauacaucuc ucgucaguct t                                            21

<210> SEQ ID NO 787
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 787
acgagagaug uauauuuaa                                               19

<210> SEQ ID NO 788
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 788
acgagagaug uauauuuaat t                                            21

<210> SEQ ID NO 789
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 789
uuaaauauac aucucucgut t                                            21

<210> SEQ ID NO 790
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 790
cuuuagucga gaaccaaugt t                                            21

<210> SEQ ID NO 791
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 791
cauugguucu cgacuaaagt t                                              21

<210> SEQ ID NO 792
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 792
gucacaaaga accgugcagt t                                              21

<210> SEQ ID NO 793
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 793
cugcacgguu cuuugugact t                                              21

<210> SEQ ID NO 794
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 794
ucggaguuca accuaagcct t                                              21

<210> SEQ ID NO 795
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 795
ggcuuagguu gaacuccgat t                                              21

<210> SEQ ID NO 796
<211> LENGTH: 21
```

-continued

```
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 796
gaaauccugc uuuagucgat t                                              21

<210> SEQ ID NO 797
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 797
ucgacuaaag caggauuuct t                                              21

<210> SEQ ID NO 798
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 798
uccugcuuua gucgagaact t                                              21

<210> SEQ ID NO 799
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 799
guucucgacu aaagcaggat t                                              21

<210> SEQ ID NO 800
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 800
uuagucgaga accaaugaut t                                              21

<210> SEQ ID NO 801
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 801
aucauugguu cucgacuaat t                                              21

<210> SEQ ID NO 802
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 802
uagucgagaa ccaaugaugt t                                              21

<210> SEQ ID NO 803
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 803
caucauuggu ucucgacuat t                                              21

<210> SEQ ID NO 804
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 804
cugcuuuagu cgagaaccat t                                              21

<210> SEQ ID NO 805
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 805
ugguucucga cuaaagcagt t                                              21

<210> SEQ ID NO 806
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 806
cgcugcaccg accaaagaat t                                              21

<210> SEQ ID NO 807
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 807
uucuuugguc ggugcagcgt t                                              21

<210> SEQ ID NO 808
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 808
ugcuuuaguc gagaaccaat t                                              21

<210> SEQ ID NO 809
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 809
uugguucucg acuaaagcat t                                              21

<210> SEQ ID NO 810
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 810
gaacuacauc gaucauggat t                                              21

<210> SEQ ID NO 811
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 811
uccaugaucg auguaguuct t                                              21

<210> SEQ ID NO 812
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 812
ugaacuacau cgaucauggt t                                              21

<210> SEQ ID NO 813
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 813
ccaugaucga uguaguucat t                                              21

<210> SEQ ID NO 814
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 814
caaagaaccg ugcagauaat t                                              21

<210> SEQ ID NO 815
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 815
uuaucugcac gguucuuugt t                                              21

<210> SEQ ID NO 816
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 816
cccacugcgu gaacauucat t                                              21

<210> SEQ ID NO 817
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 817
ugaauguuca cgcagugggt t                                              21

<210> SEQ ID NO 818
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 818
uuuagucgag aaccaaugat t                                              21

<210> SEQ ID NO 819
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 819
ucauugguuc ucgacuaaat t                                              21

<210> SEQ ID NO 820
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 820
uggaauguuc cggagaauct t                                              21

<210> SEQ ID NO 821
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 821
gauucuccgg aacauuccat t                                           21

<210> SEQ ID NO 822
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 822
cggaguucaa ccuaagccut t                                           21

<210> SEQ ID NO 823
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 823
aggcuuaggu ugaacuccgt t                                           21

<210> SEQ ID NO 824
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 824
uggcauuuga uccaugagct t                                           21

<210> SEQ ID NO 825
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 825
gcucauggau caaaugccat t                                           21

<210> SEQ ID NO 826
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 826
ucuggaaugu uccggagaat t                                            21

<210> SEQ ID NO 827
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 827
uucuccggaa cauuccagat t                                            21

<210> SEQ ID NO 828
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 828
ggcugcaaau uuacagagct t                                            21

<210> SEQ ID NO 829
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 829
gcucuguaaa uuugcagcct t                                            21

<210> SEQ ID NO 830
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 830
gcgugaacau ucacagccat t                                            21

<210> SEQ ID NO 831
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 831
uggcugugaa uguucacgct t                                             21

<210> SEQ ID NO 832
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 832
uccagguuua ugaacugact t                                             21

<210> SEQ ID NO 833
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 833
gucaguucau aaaccuggat t                                             21

<210> SEQ ID NO 834
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 834
aggcaaagug cucuuaggat t                                             21

<210> SEQ ID NO 835
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 835
uccuaagagc acuuugccut t                                             21

<210> SEQ ID NO 836
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 836
aacuacaucg aucauggagt t                                             21

<210> SEQ ID NO 837
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 837
cuccaugauc gauguaguut t                                             21

<210> SEQ ID NO 838
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 838
cauuggaauu ccuaaaauct t                                             21

<210> SEQ ID NO 839
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 839
gauuuuagga auuccaaugt t                                             21

<210> SEQ ID NO 840
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 840
auccugcuuu agucgagaat t                                             21

<210> SEQ ID NO 841
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 841
uucucgacua aagcaggaut t                                              21

<210> SEQ ID NO 842
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 842
acuacaucga ucauggagat t                                              21

<210> SEQ ID NO 843
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 843
ucuccaugau cgauguagut t                                              21

<210> SEQ ID NO 844
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 844
aauccugcuu uagucgagat t                                              21

<210> SEQ ID NO 845
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 845
ucucgacuaa agcaggauut t                                              21

<210> SEQ ID NO 846
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 846
uguccagguu uaugaacugt t                                              21

<210> SEQ ID NO 847
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 847
caguucauaa accuggacat t                                              21

<210> SEQ ID NO 848
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 848
cucggaguuc aaccuaagct t                                              21

<210> SEQ ID NO 849
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 849
gcuuagguug aacuccgagt t                                              21

<210> SEQ ID NO 850
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 850
ugaaauccug cuuuagucgt t                                              21

<210> SEQ ID NO 851
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 851
cgacuaaagc aggauuucat t                                              21

<210> SEQ ID NO 852
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 852
cagcuugucc agguuuaugt t                                              21

<210> SEQ ID NO 853
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 853
cauaaaccug gacaagcugt t                                              21

<210> SEQ ID NO 854
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 854
cgugaacauu cacagccagt t                                              21

<210> SEQ ID NO 855
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 855
cuggcuguga auguucacgt t                                              21

<210> SEQ ID NO 856
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 856
cuggcucgca uggucgacat t                                              21

<210> SEQ ID NO 857
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 857
ugucgaccau gcgagccagt t                                              21

<210> SEQ ID NO 858
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 858
agcuugucca gguuuaugat t                                              21

<210> SEQ ID NO 859
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 859
ucauaaaccu ggacaagcut t                                              21

<210> SEQ ID NO 860
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 860
ggcaaagugc ucuuaggagt t                                              21

<210> SEQ ID NO 861
<211> LENGTH: 21
```

-continued

```
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 861
cuccuaagag cacuuugcct t                                             21

<210> SEQ ID NO 862
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 862
gaucauugga auuccuaaat t                                             21

<210> SEQ ID NO 863
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 863
uuuaggaauu ccaaugauct t                                             21

<210> SEQ ID NO 864
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 864
cacugcguga acauucacat t                                             21

<210> SEQ ID NO 865
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 865
ugugaauguu cacgcagugt t                                             21

<210> SEQ ID NO 866
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 866
gucgagaacc aaugauggct t                                          21

<210> SEQ ID NO 867
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 867
gccaucauug guucucgact t                                          21

<210> SEQ ID NO 868
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 868
cuuguccagg uuuaugaact t                                          21

<210> SEQ ID NO 869
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 869
guucauaaac cuggacaagt t                                          21

<210> SEQ ID NO 870
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 870
ugugauggca ucauggccat t                                          21

<210> SEQ ID NO 871
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 871
uggccaugau gccaucacat t                                              21

<210> SEQ ID NO 872
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 872
cacaaagaac cgugcagaut t                                              21

<210> SEQ ID NO 873
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 873
aucugcacgg uucuuugugt t                                              21

<210> SEQ ID NO 874
<211> LENGTH: 18
<212> TYPE: RNA
<213> ORGANISM: Artificial Sequence
<220> FEATURE:
<223> OTHER INFORMATION: Description of Artificial Sequence: Synthetic
      fragment of siRNA specific for huntingtin

<400> SEQUENCE: 874
gauuuuagga auuccaau                                                  18

<210> SEQ ID NO 875
<211> LENGTH: 20
<212> TYPE: DNA
<213> ORGANISM: Artificial Sequence
<220> FEATURE:
<223> OTHER INFORMATION: Description of Artificial Sequence: Synthetic
      fragment of siRNA specific for huntingtin
<220> FEATURE:
<223> OTHER INFORMATION: Description of Combined DNA/RNA Molecule:
      Synthetic fragment of siRNA specific for huntingtin

<400> SEQUENCE: 875
uuaggaauuc caaugauctt                                                20

<210> SEQ ID NO 876
<211> LENGTH: 21
<212> TYPE: DNA
<213> ORGANISM: Artificial Sequence
<220> FEATURE:
```

<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 876
cauuggaauu ccuaaaauct t                                              21

<210> SEQ ID NO 877
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 877
gauuuuagga auuccaaugt t                                              21

<210> SEQ ID NO 878
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 878
gaucauugga auccuaaat t                                               21

<210> SEQ ID NO 879
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 879
uuuaggaauu ccaaugauct t                                              21

<210> SEQ ID NO 880
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 880
gucacaaaga accgugcagt t                                              21

<210> SEQ ID NO 881
<211> LENGTH: 21
<212> TYPE: DNA
<213> ORGANISM: Artificial Sequence
<220> FEATURE:

<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 881
cugcacgguu cuuugugact t                                            21

<210> SEQ ID NO 882
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 882
uccugcuuua gucgagaact t                                            21

<210> SEQ ID NO 883
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 883
guucucgacu aaagcaggat t                                            21

<210> SEQ ID NO 884
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 884
cauuggaauu ccuaaaauct t                                            21

<210> SEQ ID NO 885
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 885
gauuuuagga auuccaaugt t                                            21

<210> SEQ ID NO 886
<211> LENGTH: 21
<212> TYPE: DNA
<213> ORGANISM: Artificial Sequence
<220> FEATURE:

-continued

```
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 886
gucacaaaga accgugcagt t                                              21

<210> SEQ ID NO 887
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<221> NAME/KEY: modified_base
<222> LOCATION: (20)..(21)
<223> OTHER INFORMATION: 5-bromo-2'-deoxyuridine

<400> SEQUENCE: 887
cugcacgguu cuuugugacn n                                              21

<210> SEQ ID NO 888
<211> LENGTH: 21
<212> TYPE: DNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<223> OTHER INFORMATION: Description of Combined DNA/RNA Molecule:
      Synthetic siRNA sequence specific for huntingtin

<400> SEQUENCE: 888
gucacaaaga accgugcagt t                                              21

<210> SEQ ID NO 889
<211> LENGTH: 21
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin
<220> FEATURE:
<221> NAME/KEY: modified_base
<222> LOCATION: (20)..(21)
<223> OTHER INFORMATION: 5-bromo-2'-deoxyuridine

<400> SEQUENCE: 889
cugcacgguu cuuugugacn n                                              21

<210> SEQ ID NO 890
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA sequence specific for huntingtin

<400> SEQUENCE: 890
gucacaaaga accgugcag                                                 19
```

COMPOSITIONS AND METHODS FOR INHIBITING EXPRESSION OF HUNTINGTIN GENE

RELATED APPLICATIONS

This application is a continuation of U.S. patent application Ser. No. 12/417,502 filed on Apr. 2, 2009, now U.S. Pat. No. 8,080,532, issued on Dec. 20, 2011, which is a continuation of U.S. patent application Ser. No. 11/944,961 filed Nov. 26, 2007, now U.S. Pat. No. 7,749,978, issued on Jul. 6, 2010, which is a continuation of U.S. patent application Ser. No. 11/588,674, filed Oct. 27, 2006, now U.S. Pat. No. 7,320,965, issued on Jan. 22, 2008 which all claim the benefit of U.S. Provisional Application No. 60/731,555, filed Oct. 28, 2005, U.S. Provisional Application No. 60/819,038, filed Jul. 7, 2006, and U.S. Provisional Application No. 60/836,040, filed Aug. 7, 2006. The contents of each of these priority applications are incorporated herein by reference in their entirety.

SEQUENCE LISTING

The instant application contains a Sequence Listing which has been submitted via EFS-Web and is hereby incorporated by reference in its entirety. Said ASCII copy, created on Oct. 4, 2011, is named 19545US_CRF_sequencelisting.txt, and is 303,121 bytes in size.

FIELD OF THE INVENTION

This invention relates to double-stranded ribonucleic acid (dsRNA), and its use in mediating RNA interference to inhibit the expression of the Huntingtin gene.

BACKGROUND OF THE INVENTION

Recently, double-stranded RNA molecules (dsRNA) have been shown to block gene expression in a highly conserved regulatory mechanism known as RNA interference (RNAi). WO 99/32619 (Fire et al.) discloses the use of a dsRNA of at least 25 nucleotides in length to inhibit the expression of genes in *C. elegans*. dsRNA has also been shown to degrade target RNA in other organisms, including plants (see, e.g., WO 99/53050, Waterhouse et al.; and WO 99/61631, Heifetz et al.), *Drosophila* (see, e.g., Yang, D., et al., *Curr. Biol.* (2000) 10:1191-1200), and mammals (see WO 00/44895, Limmer; and DE 101 00 586.5, Kreutzer et al.). This natural mechanism has now become the focus for the development of a new class of pharmaceutical agents for treating disorders that are caused by the aberrant regulation of genes or the expression of a mutant form of a gene.

Huntington's disease is a progressive neurodegenerative disorder characterized by motor disturbance, cognitive loss and psychiatric manifestations (Martin and Gusella, N. Engl. J. Med. 315:1267-1276 (1986). It is inherited in an autosomal dominant fashion, and affects about 1/10,000 individuals in most populations of European origin (Harper, P. S. et al., in Huntington's disease, W. B. Saunders, Philadelphia, 1991). The hallmark of Huntington's disease is a distinctive choreic movement disorder that typically has a subtle, insidious onset in the fourth to fifth decade of life and gradually worsens over a course of 10 to 20 years until death. Occasionally, Huntington's disease is expressed in juveniles typically manifesting with more severe symptoms including rigidity and a more rapid course. Juvenile onset of Huntington's disease is associated with a preponderance of paternal transmission of the disease allele. The neuropathology of Huntington's disease also displays a distinctive pattern, with selective loss of neurons that is most severe in the caudate and putamen regions of the brain. The biochemical basis for neuronal death in Huntington's disease has not yet been explained, and there is consequently no treatment effective in delaying or preventing the onset and progression of this devastating disorder.

Although an actual mechanism for Huntington's disease remains elusive, Huntington's disease has been shown to be an autosomal dominant neurodegenerative disorder caused by an expanding glutamine repeat in a gene termed IT15 or Huntingtin (HD). Although this gene is widely expressed and is required for normal development, the pathology of Huntington's disease is restricted to the brain, for reasons that remain poorly understood. The Huntingtin gene product is expressed at similar levels in patients and controls, and the genetics of the disorder suggest that the expansion of the polyglutamine repeat induces a toxic gain of function, perhaps through interactions with other cellular proteins.

Treatment for Huntington's disease is currently not available. The choreic movements and agitated behaviors may be suppressed, usually only partially, by antipsychotics (e.g., chlorpromazine 100 to 900 mg/day po or haloperidol 10 to 90 mg/day po) or reserpine begun with 0.1 mg/day po and increased until adverse effects of lethargy, hypotension, or parkinsonism occur.

Despite significant advances in the field of RNAi and Huntington's disease treatment, there remains a need for an agent that can selectively and efficiently silence the HD gene using the cell's own RNAi machinery that has both high biological activity and in vivo stability, and that can effectively inhibit expression of a target Huntingtin gene.

SUMMARY OF THE INVENTION

The invention provides double-stranded ribonucleic acid (dsRNA), as well as compositions and methods for inhibiting the expression of the HD gene in a cell or mammal using such dsRNA. The invention also provides compositions and methods for treating diseases caused by the expression of a mutant form of the HD gene. The dsRNA of the invention comprises an RNA strand (the antisense strand) having a region which is less than 30 nucleotides in length and is substantially complementary to at least part of an mRNA transcript of the HD gene.

In one embodiment, the invention provides double-stranded ribonucleic acid (dsRNA) molecules for inhibiting the expression of the HD gene. The dsRNA comprises at least two sequences that are complementary to each other. The dsRNA comprises a sense strand comprising a first sequence and an antisense strand comprising a second sequence. The antisense strand comprises a nucleotide sequence which is substantially complementary to at least part of an mRNA encoding the huntingtin protein, and the region of complementarity is less than 30 nucleotides in length. The dsRNA, upon contacting with a cell expressing the HD gene, inhibits the expression of the HD gene by at least 20%.

For example, the dsRNA molecules of the invention can be comprised of a first sequence of the dsRNA that is selected from the group consisting of the sense sequences of Tables 1, 2, 7, 8 or 10 and the second sequence is selected from the group consisting of the antisense sequences of Tables 1, 2, 7, 8 or 10. The dsRNA molecules of the invention can be comprised of naturally occurring nucleotides or can be comprised of at least one modified nucleotide, such as a 2'-O-methyl modified nucleotide, a nucleotide comprising a 5'-phosphorothioate group, and a terminal nucleotide linked to a cholesteryl derivative or dodecanoic acid bisdecylamide group. Alternatively, the modified nucleotide may be chosen from the group of: a 2'-deoxy-2'-fluoro modified nucleotide, a 2'-deoxy-modified nucleotide, a locked nucleotide, an abasic nucleotide, 2'-amino-modified nucleotide, 2'-alkyl-modified nucleotide, morpholino nucleotide, a phosphoramidate, and a non-natural base comprising nucleotide. Preferably, the first sequence of said dsRNA is selected from the group consisting of the sense sequences of Table 2 and the second sequence is selected from the group consisting of the antisense sequences of Table 2.

In another embodiment, the invention provides a cell comprising one of the dsRNAs of the invention. The cell is preferably a mammalian cell, such as a human cell.

In another embodiment, the invention provides a pharmaceutical composition for inhibiting the expression of the HD gene in an organism, comprising one or more of the dsRNA of the invention and a pharmaceutically acceptable carrier.

In another embodiment, the invention provides a method for inhibiting the expression of the HD gene in a cell, comprising the following steps:
  (a) introducing into the cell a double-stranded ribonucleic acid (dsRNA), wherein the dsRNA comprises at least two sequences that are complementary to each other. The dsRNA comprises a sense strand comprising a first sequence and an antisense strand comprising a second sequence. The antisense strand comprises a region of complementarity which is substantially complementary to at least a part of a mRNA encoding the HD gene, and wherein the region of complementarity is less than 30 nucleotides in length and wherein the dsRNA, upon contact with a cell expressing the HD gene, inhibits expression of the HD gene by at least 20%; and
  (b) maintaining the cell produced in step (a) for a time sufficient to obtain degradation of the mRNA transcript of the HD gene, thereby inhibiting expression of the HD gene in the cell.

In another embodiment, the invention provides methods for treating, preventing or managing Huntington's disease comprising administering to a patient in need of such treatment, prevention or management a therapeutically or prophylactically effective amount of one or more of the dsRNAs of the invention.

In another embodiment, the invention provides vectors for inhibiting the expression of the HD gene in a cell, comprising a regulatory sequence operably linked to a nucleotide sequence that encodes at least one strand of one of the dsRNA of the invention.

In another embodiment, the invention provides cell comprising a vector for inhibiting the expression of the HD gene in a cell. The vector comprises a regulatory sequence operably linked to a nucleotide sequence that encodes at least one strand of one of the dsRNA of the invention.

DETAILED DESCRIPTION OF THE INVENTION

Figure 1:
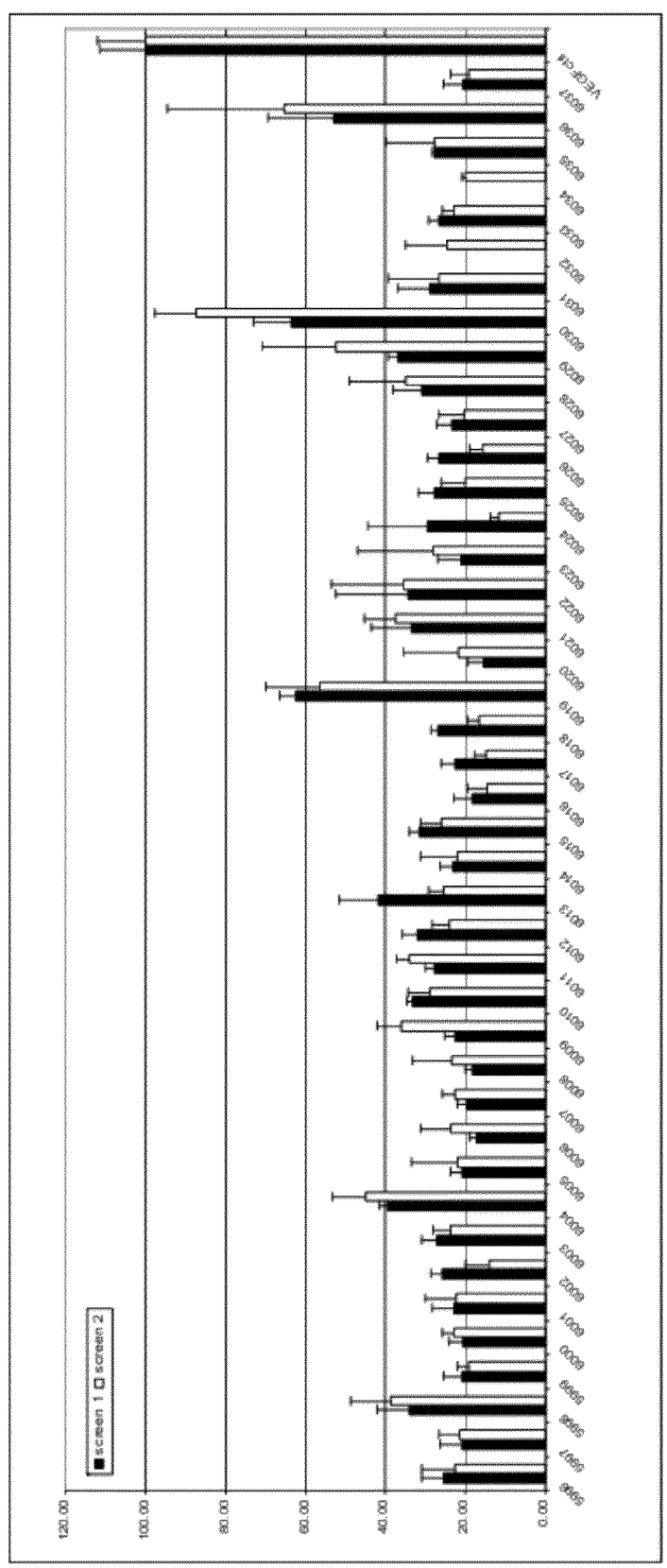
FIG. 1. In vitro activity of the dsRNAs provided in Table 2 against endogenous human HD mRNA expression in HeLa cells.

The invention provides double-stranded ribonucleic acid (dsRNA), as well as compositions and methods for inhibiting the expression of the HD gene in a cell or mammal using the dsRNA. The invention also provides compositions and methods for treating diseases in a mammal caused by the expression of the HD gene, or a mutant form thereof, using dsRNA. dsRNA directs the sequence-specific degradation of mRNA through a process known as RNA interference (RNAi). The process occurs in a wide variety of organisms, including mammals and other vertebrates.

The dsRNA of the invention comprises an RNA strand (the antisense strand) having a region which is less than 30 nucleotides in length and is substantially complementary to at least part of an mRNA transcript of the HD gene. The use of these dsRNAs enables the targeted degradation of mRNAs of genes that are implicated in Huntington Disease. Using cell-based and animal assays, the present inventors have demonstrated that very low dosages of these dsRNA can specifically and efficiently mediate RNAi, resulting in significant inhibition of expression of the HD gene. Thus, the methods and compositions of the invention comprising these dsRNAs are useful for treating Huntington disease.

The following detailed description discloses how to make and use the dsRNA and compositions containing dsRNA to inhibit the expression of a target HD gene, as well as compositions and methods for treating diseases and disorders caused by the expression of these genes. The pharmaceutical compositions of the invention comprise a dsRNA having an antisense strand comprising a region of complementarity which is less than 30 nucleotides in length and is substantially complementary to at least part of an RNA transcript of the HD gene, together with a pharmaceutically acceptable carrier (Human HD mRNA (NM-002111), mouse HD mRNA (NM_010414) and rat HD mRNA (U18650)).

Accordingly, certain aspects of the invention provide pharmaceutical compositions comprising the dsRNA of the invention together with a pharmaceutically acceptable carrier, methods of using the compositions to inhibit expression of the HD gene, and methods of using the pharmaceutical compositions to treat diseases caused by expression of a mutant form of the HD gene.

I. DEFINITIONS

For convenience, the meaning of certain terms and phrases used in the specification, examples, and appended claims, are provided below. If there is an apparent discrepancy between the usage of a term in other parts of this specification and its definition provided in this section, the definition in this section shall prevail.

"G," "C," "A" and "U" each generally stand for a nucleotide that contains guanine, cytosine, adenine, and uracil as a base, respectively. However, it will be understood that the term "ribonucleotide" or "nucleotide" can also refer to a modified nucleotide, as further detailed below, or a surrogate replacement moiety. The skilled person is well aware that guanine, cytosine, adenine, and uracil may be replaced by other moieties without substantially altering the base pairing properties of an oligonucleotide comprising a nucleotide bearing such replacement moiety. For example, without limitation, a nucleotide comprising inosine as its base may base pair with nucleotides containing adenine, cytosine, or uracil. Hence, nucleotides containing uracil, guanine, or adenine may be replaced in the nucleotide sequences of the invention by a nucleotide containing, for example, inosine. Sequences comprising such replacement moieties are embodiments of the invention.

The gene involved in Huntington's disease (IT-15) is located at the end of the short arm of chromosome 4. A mutation occurs in the coding region of this gene and produces an unstable expanded trinucleotide repeat (cytosine-adenosine-guanosine), resulting in a protein with an expanded glutamate sequence. The normal and abnormal functions of this protein (termed huntingtin) are unknown. The abnormal huntingtin protein appears to accumulate in neuronal nuclei of transgenic mice, but the causal relationship of this accumulation to neuronal death is uncertain.

By "Huntingtin" or "HD" as used herein is meant, any Huntingtin protein, peptide, or polypeptide associated with the development or maintenance of Huntington disease. The terms "Huntingtin" and "HD" also refer to nucleic acid sequences encoding any huntingtin protein, peptide, or polypeptide, such as Huntingtin RNA or Huntingtin DNA (see for example Van Dellen et al., Jan. 24, 2004, Neurogenetics). For the Examples, the HD mRNA sequences used were Human HD mRNA (NM-002111), mouse HD mRNA (NM_010414) and rat HD mRNA (U18650).

As used herein, "target sequence" refers to a contiguous portion of the nucleotide sequence of an mRNA molecule formed during the transcription of the HD gene, including mRNA that is a product of RNA processing of a primary transcription product.

As used herein, the term "strand comprising a sequence" refers to an oligonucleotide comprising a chain of nucleotides that is described by the sequence referred to using the standard nucleotide nomenclature.

As used herein, and unless otherwise indicated, the term "complementary," when used to describe a first nucleotide sequence in relation to a second nucleotide sequence, refers to the ability of an oligonucleotide or polynucleotide comprising the first nucleotide sequence to hybridize and form a duplex structure under certain conditions with an oligonucleotide or polynucleotide comprising the second nucleotide sequence, as will be understood by the skilled person. Such conditions can, for example, be stringent conditions, where stringent conditions may include: 400 mM NaCl, 40 mM PIPES pH 6.4, 1 mM EDTA, 50° C. or 70° C. for 12-16 hours followed by washing. Other conditions, such as physiologically relevant conditions as may be encountered inside an organism, can apply. The skilled person will be able to determine the set of conditions most appropriate for a test of complementarity of two sequences in accordance with the ultimate application of the hybridized nucleotides.

This includes base-pairing of the oligonucleotide or polynucleotide comprising the first nucleotide sequence to the oligonucleotide or polynucleotide comprising the second nucleotide sequence over the entire length of the first and second nucleotide sequence. Such sequences can be referred to as "fully complementary" with respect to each other herein. However, where a first sequence is referred to as "substantially complementary" with respect to a second sequence herein, the two sequences can be fully complementary, or they may form one or more, but preferably not more than 4, 3 or 2 mismatched base pairs upon hybridization, while retaining the ability to hybridize under the conditions most relevant to their ultimate application. However, where two oligonucleotides are designed to form, upon hybridization, one or more single stranded overhangs, such overhangs shall not be regarded as mismatches with regard to the determination of complementarity. For example, a dsRNA comprising one oligonucleotide 21 nucleotides in length and another oligonucleotide 23 nucleotides in length, wherein the longer oligonucleotide comprises a sequence of 21 nucleotides that is fully complementary to the shorter oligonucleotide, may yet be referred to as "fully complementary" for the purposes of the invention.

"Complementary" sequences, as used herein, may also include, or be formed entirely from, non-Watson-Crick base pairs and/or base pairs formed from non-natural and modified nucleotides, in as far as the above requirements with respect to their ability to hybridize are fulfilled.

The terms "complementary", "fully complementary" and "substantially complementary" herein may be used with respect to the base matching between the sense strand and the antisense strand of a dsRNA, or between the antisense strand of a dsRNA and a target sequence, as will be understood from the context of their use.

As used herein, a polynucleotide which is "substantially complementary to at least part of" a messenger RNA (mRNA) refers to a polynucleotide which is substantially complementary to a contiguous portion of the mRNA of interest (e.g., encoding HD). For example, a polynucleotide is complementary to at least a part of a HD mRNA if the sequence is substantially complementary to a non-interrupted portion of a mRNA encoding HD.

The term "double-stranded RNA" or "dsRNA", as used herein, refers to a ribonucleic acid molecule, or complex of ribonucleic acid molecules, having a duplex structure comprising two anti-parallel and substantially complementary, as defined above, nucleic acid strands. The two strands forming the duplex structure may be different portions of one larger RNA molecule, or they may be separate RNA molecules. Where the two strands are part of one larger molecule, and therefore are connected by an uninterrupted chain of nucleotides between the 3'-end of one strand and the 5'end of the respective other strand forming the duplex structure, the connecting RNA chain is referred to as a "hairpin loop". Where the two strands are connected covalently by means other than an uninterrupted chain of nucleotides between the 3'-end of one strand and the 5'end of the respective other strand forming the duplex structure, the connecting structure is referred to as a "linker". The RNA strands may have the same or a different number of nucleotides. The maximum number of base pairs is the number of nucleotides in the shortest strand of the dsRNA. In addition to the duplex structure, a dsRNA may comprise one or more nucleotide overhangs.

As used herein, a "nucleotide overhang" refers to the unpaired nucleotide or nucleotides that protrude from the duplex structure of a dsRNA when a 3'-end of one strand of the dsRNA extends beyond the 5'-end of the other strand, or vice versa. "Blunt" or "blunt end" means that there are no unpaired nucleotides at that end of the dsRNA, i.e., no nucleotide overhang. A "blunt ended" dsRNA is a dsRNA that is double-stranded over its entire length, i.e., no nucleotide overhang at either end of the molecule.

The term "antisense strand" refers to the strand of a dsRNA which includes a region that is substantially complementary to a target sequence. As used herein, the term "region of complementarity" refers to the region on the antisense strand that is substantially complementary to a sequence, for example a target sequence, as defined herein. Where the region of complementarity is not fully complementary to the target sequence, the mismatches are most tolerated in the terminal regions and, if present, are preferably in a terminal region or regions, e.g., within 6, 5, 4, 3, or 2 nucleotides of the 5' and/or 3' terminus.

The term "sense strand," as used herein, refers to the strand of a dsRNA that includes a region that is substantially complementary to a region of the antisense strand.

"Introducing into a cell", when referring to a dsRNA, means facilitating uptake or absorption into the cell, as is understood by those skilled in the art. Absorption or uptake of dsRNA can occur through unaided diffusive or active cellular processes, or by auxiliary agents or devices. The meaning of this term is not limited to cells in vitro; a dsRNA may also be "introduced into a cell", wherein the cell is part of a living organism. In such instance, introduction into the cell will include the delivery to the organism. For example, for in vivo delivery, dsRNA can be injected into a tissue site or administered systemically. In vitro introduction into a cell includes methods known in the art such as electroporation and lipofection.

The terms "silence" and "inhibit the expression of", in as far as they refer to the HD gene, herein refer to the at least partial suppression of the expression of the HD gene, as manifested by a reduction of the amount of mRNA transcribed from the HD gene which may be isolated from a first cell or group of cells in which the HD gene is transcribed and which has or have been treated such that the expression of the HD gene is inhibited, as compared to a second cell or group of cells substantially identical to the first cell or group of cells but which has or have not been so treated (control cells). The degree of inhibition is usually expressed in terms of $$\frac{(mRNA \text{ in control cells}) - (mRNA \text{ in treated cells})}{(mRNA \text{ in control cells})} \cdot 100\%$$

Alternatively, the degree of inhibition may be given in terms of a reduction of a parameter that is functionally linked to HD gene transcription, e.g. the amount of protein encoded by the HD gene which is secreted by a cell, or the number of cells displaying a certain phenotype, e.g. apoptosis. In principle, HD gene silencing may be determined in any cell expressing the target, either constitutively or by genomic engineering, and by any appropriate assay. However, when a reference is needed in order to determine whether a given siRNA inhibits the expression of the HD gene by a certain degree and therefore is encompassed by the instant invention, the assay provided in the Examples below shall serve as such reference.

For example, in certain instances, expression of the HD gene is suppressed by at least about 20%, 25%, 35%, or 50% by administration of the double-stranded oligonucleotide of the invention. In a preferred embodiment, the HD gene is suppressed by at least about 60%, 70%, or 80% by administration of the double-stranded oligonucleotide of the invention. In a more preferred embodiment, the HD gene is suppressed by at least about 85%, 90%, or 95% by administration of the double-stranded oligonucleotide of the invention. In a most preferred embodiment, the HD gene is suppressed by at least about 98%, 99% or more by administration of the double-stranded oligonucleotide of the invention.

As used herein, the term "treatment" refers to the application or administration of a therapeutic agent to a patient, or application or administration of a therapeutic agent to an isolated tissue or cell line from a patient, who has a disorder, e.g., a disease or condition, a symptom of disease, or a predisposition toward a disease, with the purpose to cure, heal, alleviate, relieve, alter, remedy, ameliorate, improve, or affect the disease, the symptoms of disease, or the predisposition toward disease. A "patient" may be a human, but can also be a non-human animal. Treatment can refer to the reduction of any one of the overt symptoms of Huntington's disease, such as dementia or psychiatric disturbances, ranging from apathy and irritability to full-blown bipolar or schizophreniform disorder, motor manifestations include flicking movements of the extremities, a lilting gait, motor impersistence (inability to sustain a motor act, such as tongue protrusion), facial grimacing, ataxia, and dystonia.

As used herein, the phrases "therapeutically effective amount" and "prophylactically effective amount" refer to an amount that provides a therapeutic benefit in the treatment, prevention, or management of Huntington's disease or an overt symptom of the disease. The specific amount that is therapeutically effective can be readily determined by ordinary medical practitioner, and may vary depending on factors known in the art, such as, e.g. the type of Huntington's disease, the patient's history and age, the stage of Huntington's disease, and the administration of other anti-Huntington's disease agents.

As used herein, a "pharmaceutical composition" comprises a pharmacologically effective amount of a dsRNA and a pharmaceutically acceptable carrier. As used herein, "pharmacologically effective amount," "therapeutically effective amount" or simply "effective amount" refers to that amount of an RNA effective to produce the intended pharmacological, therapeutic or preventive result. For example, if a given clinical treatment is considered effective when there is at least a 25% reduction in a measurable parameter associated with a disease or disorder, a therapeutically effective amount of a drug for the treatment of that disease or disorder is the amount necessary to effect at least a 25% reduction in that parameter.

The term "pharmaceutically acceptable carrier" refers to a carrier for administration of a therapeutic agent. Such carriers include, but are not limited to, saline, buffered saline, dextrose, water, glycerol, ethanol, and combinations thereof. The term specifically excludes cell culture medium. For drugs administered orally, pharmaceutically acceptable carriers include, but are not limited to pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

As used herein, a "transformed cell" is a cell into which a vector has been introduced from which a dsRNA molecule may be expressed.

II. DOUBLE-STRANDED RIBONUCLEIC ACID (dsRNA)

In one embodiment, the invention provides double-stranded ribonucleic acid (dsRNA) molecules for inhibiting the expression of the HD gene in a cell or mammal, wherein the dsRNA comprises an antisense strand comprising a region of complementarity which is complementary to at least a part of an mRNA formed in the expression of the HD gene, and wherein the region of complementarity is less than 30 nucleotides in length and wherein said dsRNA, upon contact with a cell expressing said HD gene, inhibits the expression of said HD gene by at least 20%. The dsRNA comprises two RNA strands that are sufficiently complementary to hybridize to form a duplex structure. One strand of the dsRNA (the antisense strand) comprises a region of complementarity that is substantially complementary, and preferably fully complementary, to a target sequence, derived from the sequence of an mRNA formed during the expression of the HD gene, the other strand (the sense strand) comprises a region which is complementary to the antisense strand, such that the two strands hybridize and form a duplex structure when combined under suitable conditions. Preferably, the duplex structure is between 15 and 30, more preferably between 18 and 25, yet more preferably between 19 and 24, and most preferably between 21 and 23 base pairs in length. Similarly, the region of complementarity to the target sequence is between 15 and 30, more preferably between 18 and 25, yet more preferably between 19 and 24, and most preferably between 21 and 23 nucleotides in length. The dsRNA of the invention may further comprise one or more single-stranded nucleotide overhang(s). The dsRNA can be synthesized by standard methods known in the art as further discussed below, e.g., by use of an automated DNA synthesizer, such as are commercially available from, for example, Biosearch, Applied Biosystems, Inc. In a preferred embodiment, the HD gene is the human HD gene. In specific embodiments, the antisense strand of the dsRNA comprises the antisense sequences of Tables 1, 2, 7, 8 or 10 and the second sequence is selected from the group consisting of the sense sequences of Tables 1, 2, 7, 8 or 10.

In further embodiments, the dsRNA comprises at least one nucleotide sequence selected from the groups of sequences provided in Tables 1, 2, 7, 8 or 10. In other embodiments, the dsRNA comprises at least two sequences selected from this group, wherein one of the at least two sequences is complementary to another of the at least two sequences, and one of the at least two sequences is substantially complementary to a sequence of an mRNA generated in the expression of the HD gene. Preferably, the dsRNA comprises two oligonucleotides, wherein one oligonucleotide is described by Tables 1, 2, 7, 8 or 10 and the second oligonucleotide is described Tables 1, 2, 7, 8 or 10.

The skilled person is well aware that dsRNAs comprising a duplex structure of between 20 and 23, but specifically 21, base pairs have been hailed as particularly effective in inducing RNA interference (Elbashir et al., EMBO 2001, 20:6877-6888). However, others have found that shorter or longer dsRNAs can be effective as well. In the embodiments described above, by virtue of the nature of the oligonucleotide sequences provided in Tables 1, 2, 7, 8 or 10, the dsRNAs of the invention can comprise at least one strand of a length of minimally 21 nt. It can be reasonably expected that shorter dsRNAs comprising one of the sequences of Tables 1, 2, 7, 8 or 10 minus only a few nucleotides on one or both ends may be similarly effective as compared to the dsRNAs described above. Hence, dsRNAs comprising a partial sequence of at least 15, 16, 17, 18, 19, 20, or more contiguous nucleotides from one of the sequences of Tables 1, 2, 7, 8 or 10, and differing in their ability to inhibit the expression of the HD gene in a FACS assay as described herein below by not more than 5, 10, 15, 20, 25, or 30% inhibition from a dsRNA comprising the full sequence, are contemplated by the invention.

The dsRNA of the invention can contain one or more mismatches to the target sequence. In a preferred embodiment, the dsRNA of the invention contains no more than 3 mismatches. If the antisense strand of the dsRNA contains mismatches to a target sequence, it is preferable that the area of mismatch not be located in the center of the region of complementarity. If the antisense strand of the dsRNA contains mismatches to the target sequence, it is preferable that the mismatch be restricted to 5 nucleotides from either end, for example 5, 4, 3, 2, or 1 nucleotide from either the 5' or 3' end of the region of complementarity. For example, for a 23 nucleotide dsRNA strand which is complementary to a region of the HD gene, the dsRNA preferably does not contain any mismatch within the central 13 nucleotides. The methods described within the invention can be used to determine whether a dsRNA containing a mismatch to a target sequence is effective in inhibiting the expression of the HD gene. Consideration of the efficacy of dsRNAs with mismatches in inhibiting expression of the HD gene is important, especially if the particular region of complementarity in the HD gene is known to have polymorphic sequence variation within the population.

In one embodiment, at least one end of the dsRNA has a single-stranded nucleotide overhang of 1 to 4, preferably 1 or 2 nucleotides. dsRNAs having at least one nucleotide overhang have unexpectedly superior inhibitory properties than their blunt-ended counterparts. Moreover, the present inventors have discovered that the presence of only one nucleotide overhang strengthens the interference activity of the dsRNA, without affecting its overall stability. dsRNA having only one overhang has proven particularly stable and effective in vivo, as well as in a variety of cells, cell culture mediums, blood, and serum. Preferably, the single-stranded overhang is located at the 3'-terminal end of the antisense strand or, alternatively, at the 3'-terminal end of the sense strand. The dsRNA may also have a blunt end, preferably located at the 5'-end of the antisense strand. Such dsRNAs have improved stability and inhibitory activity, thus allowing administration at low dosages, i.e., less than 5 mg/kg body weight of the recipient per day. Preferably, the antisense strand of the dsRNA has a nucleotide overhang at the 3'-end, and the 5'-end is blunt. In another embodiment, one or more of the nucleotides in the overhang is replaced with a nucleoside thiophosphate.

In yet another embodiment, the dsRNA is chemically modified to enhance stability. The nucleic acids of the invention may be synthesized and/or modified by methods well established in the art, such as those described in "Current protocols in nucleic acid chemistry", Beaucage, S. L. et al. (Edrs.), John Wiley & Sons, Inc., New York, N.Y., USA, which is hereby incorporated herein by reference. Chemical modifications may include, but are not limited to 2' modifications, introduction of non-natural bases, covalent attachment to a ligand, and replacement of phosphate linkages with thiophosphate linkages. In this embodiment, the integrity of the duplex structure is strengthened by at least one, and preferably two, chemical linkages. Chemical linking may be achieved by any of a variety of well-known techniques, for example by introducing covalent, ionic or hydrogen bonds; hydrophobic interactions, van der Waals or stacking interactions; by means of metal-ion coordination, or through use of purine analogues. Preferably, the chemical groups that can be used to modify the dsRNA include, without limitation, methylene blue; bifunctional groups, preferably bis-(2-chloroethyl)amine; N-acetyl-N'-(p-glyoxylbenzoyl)cystamine; 4-thiouracil; and psoralen. In one preferred embodiment, the linker is a hexa-ethylene glycol linker. In this case, the dsRNA are produced by solid phase synthesis and the hexa-ethylene glycol linker is incorporated according to standard methods (e.g., Williams, D. J., and K. B. Hall, *Biochem.* (1996) 35:14665-14670). In a particular embodiment, the 5'-end of the antisense strand and the 3'-end of the sense strand are chemically linked via a hexaethylene glycol linker. In another embodiment, at least one nucleotide of the dsRNA comprises a phosphorothioate or phosphorodithioate groups. The chemical bond at the ends of the dsRNA is preferably formed by triple-helix bonds. Table 2 provides examples of modified RNAi agents of the invention.

In certain embodiments, a chemical bond may be formed by means of one or several bonding groups, wherein such bonding groups are preferably poly-(oxyphosphinicooxy-1, 3-propandiol)- and/or polyethylene glycol chains. In other embodiments, a chemical bond may also be formed by means of purine analogs introduced into the double-stranded structure instead of purines. In further embodiments, a chemical bond may be formed by azabenzene units introduced into the double-stranded structure. In still further embodiments, a chemical bond may be formed by branched nucleotide analogs instead of nucleotides introduced into the double-stranded structure. In certain embodiments, a chemical bond may be induced by ultraviolet light.

In yet another embodiment, the nucleotides at one or both of the two single strands may be modified to prevent or inhibit the activation of cellular enzymes, such as, for example, without limitation, certain nucleases. Techniques for inhibiting the activation of cellular enzymes are known in the art including, but not limited to, 2'-amino modifications, 2'-amino sugar modifications, 2'-F sugar modifications, 2'-F modifications, 2'-alkyl sugar modifications, uncharged backbone modifications, morpholino modifications, 2'-O-methyl modifications, and phosphoramidate (see, e.g., Wagner, *Nat. Med.* (1995) 1:1116-8). Thus, at least one 2'-hydroxyl group of the nucleotides on a dsRNA is replaced by a chemical group, preferably by a 2'-amino or a 2'-methyl group. Also, at least one nucleotide may be modified to form a locked nucleotide. Such locked nucleotide contains a methylene bridge that connects the 2'-oxygen of ribose with the 4'-carbon of ribose. Oligonucleotides containing the locked nucleotide are described in (Koshkin, A. A., et al., *Tetrahedron* (1998), 54: 3607-3630 and Obika, S. et al., *Tetrahedron Lett.* (1998), 39: 5401-5404). Introduction of a locked nucleotide into an oligonucleotide improves the affinity for complementary sequences and increases the melting temperature by several degrees (Braasch, D. A. and D. R. Corey, *Chem. Biol.* (2001), 8:1-7).

Conjugating a ligand to a dsRNA can enhance its cellular absorption. In certain instances, a hydrophobic ligand is conjugated to the dsRNA to facilitate direct permeation of the cellular membrane. Alternatively, the ligand conjugated to the dsRNA is a substrate for receptor-mediated endocytosis. These approaches have been used to facilitate cell permeation of antisense oligonucleotides. For example, cholesterol has been conjugated to various antisense oligonucleotides resulting in compounds that are substantially more active compared to their non-conjugated analogs. See M. Manoharan *Antisense & Nucleic Acid Drug Development* 2002, 12, 103. Other lipophilic compounds that have been conjugated to oligonucleotides include 1-pyrene butyric acid, 1,3-bis-O-(hexadecyl)glycerol, and menthol. One example of a ligand for receptor-mediated endocytosis is folic acid. Folic acid enters the cell by folate-receptor-mediated endocytosis. dsRNA compounds bearing folic acid would be efficiently transported into the cell via the folate-receptor-mediated endocytosis. Li and coworkers report that attachment of folic acid to the 3'-terminus of an oligonucleotide resulted in an 8-fold increase in cellular uptake of the oligonucleotide. Li, S.; Deshmukh, H. M.; Huang, L. *Pharm. Res.* 1998, 15, 1540. Other ligands that have been conjugated to oligonucleotides include polyethylene glycols, carbohydrate clusters, cross-linking agents, porphyrin conjugates, and delivery peptides.

In certain instances, conjugation of a cationic ligand to oligonucleotides often results in improved resistance to nucleases. Representative examples of cationic ligands are propylammonium and dimethylpropylammonium. Interestingly, antisense oligonucleotides were reported to retain their high binding affinity to mRNA when the cationic ligand was dispersed throughout the oligonucleotide. See M. Manoharan *Antisense & Nucleic Acid Drug Development* 2002, 12, 103 and references therein.

The ligand-conjugated dsRNA of the invention may be synthesized by the use of a dsRNA that bears a pendant reactive functionality, such as that derived from the attachment of a linking molecule onto the dsRNA. This reactive oligonucleotide may be reacted directly with commercially-available ligands, ligands that are synthesized bearing any of a variety of protecting groups, or ligands that have a linking moiety attached thereto. The methods of the invention facilitate the synthesis of ligand-conjugated dsRNA by the use of, in some preferred embodiments, nucleoside monomers that have been appropriately conjugated with ligands and that may further be attached to a solid-support material. Such ligand-nucleoside conjugates, optionally attached to a solid-support material, are prepared according to some preferred embodiments of the methods of the invention via reaction of a selected serum-binding ligand with a linking moiety located on the 5' position of a nucleoside or oligonucleotide. In certain instances, an dsRNA bearing an aralkyl ligand attached to the 3'-terminus of the dsRNA is prepared by first covalently attaching a monomer building block to a controlled-pore-glass support via a long-chain aminoalkyl group. Then, nucleotides are bonded via standard solid-phase synthesis techniques to the monomer building-block bound to the solid support. The monomer building block may be a nucleoside or other organic compound that is compatible with solid-phase synthesis.

The dsRNA used in the conjugates of the invention may be conveniently and routinely made through the well-known technique of solid-phase synthesis. Equipment for such synthesis is sold by several vendors including, for example, Applied Biosystems (Foster City, Calif.). Any other means for such synthesis known in the art may additionally or alternatively be employed. It is also known to use similar techniques to prepare other oligonucleotides, such as the phosphorothioates and alkylated derivatives.

Teachings regarding the synthesis of particular modified oligonucleotides may be found in the following U.S. patents: U.S. Pat. Nos. 5,138,045 and 5,218,105, drawn to polyamine conjugated oligonucleotides; U.S. Pat. No. 5,212,295, drawn to monomers for the preparation of oligonucleotides having chiral phosphorus linkages; U.S. Pat. Nos. 5,378,825 and 5,541,307, drawn to oligonucleotides having modified backbones; U.S. Pat. No. 5,386,023, drawn to backbone-modified oligonucleotides and the preparation thereof through reductive coupling; U.S. Pat. No. 5,457,191, drawn to modified nucleobases based on the 3-deazapurine ring system and methods of synthesis thereof; U.S. Pat. No. 5,459,255, drawn to modified nucleobases based on N-2 substituted purines; U.S. Pat. No. 5,521,302, drawn to processes for preparing oligonucleotides having chiral phosphorus linkages; U.S. Pat. No. 5,539,082, drawn to peptide nucleic acids; U.S. Pat. No. 5,554,746, drawn to oligonucleotides having β-lactam backbones; U.S. Pat. No. 5,571,902, drawn to methods and materials for the synthesis of oligonucleotides; U.S. Pat. No.

5,578,718, drawn to nucleosides having alkylthio groups, wherein such groups may be used as linkers to other moieties attached at any of a variety of positions of the nucleoside; U.S. Pat. Nos. 5,587,361 and 5,599,797, drawn to oligonucleotides having phosphorothioate linkages of high chiral purity; U.S. Pat. No. 5,506,351, drawn to processes for the preparation of 2'-O-alkyl guanosine and related compounds, including 2,6-diaminopurine compounds; U.S. Pat. No. 5,587,469, drawn to oligonucleotides having N-2 substituted purines; U.S. Pat. No. 5,587,470, drawn to oligonucleotides having 3-deazapurines; U.S. Pat. No. 5,223,168, and U.S. Pat. No. 5,608,046, both drawn to conjugated 4'-desmethyl nucleoside analogs; U.S. Pat. Nos. 5,602,240, and 5,610,289, drawn to backbone-modified oligonucleotide analogs; U.S. Pat. Nos. 6,262,241, and 5,459,255, drawn to, inter alia, methods of synthesizing 2'-fluoro-oligonucleotides.

In the ligand-conjugated dsRNA and ligand-molecule bearing sequence-specific linked nucleosides of the invention, the oligonucleotides and oligonucleosides may be assembled on a suitable DNA synthesizer utilizing standard nucleotide or nucleoside precursors, or nucleotide or nucleoside conjugate precursors that already bear the linking moiety, ligand-nucleotide or nucleoside-conjugate precursors that already bear the ligand molecule, or non-nucleoside ligand-bearing building blocks.

When using nucleotide-conjugate precursors that already bear a linking moiety, the synthesis of the sequence-specific linked nucleosides is typically completed, and the ligand molecule is then reacted with the linking moiety to form the ligand-conjugated oligonucleotide. Oligonucleotide conjugates bearing a variety of molecules such as steroids, vitamins, lipids and reporter molecules, has previously been described (see Manoharan et al., PCT Application WO 93/07883). In a preferred embodiment, the oligonucleotides or linked nucleosides of the invention are synthesized by an automated synthesizer using phosphoramidites derived from ligand-nucleoside conjugates in addition to the standard phosphoramidites and non-standard phosphoramidites that are commercially available and routinely used in oligonucleotide synthesis.

The incorporation of a 2'-O-methyl, 2'-O-ethyl, 2'-O-propyl, 2'-O-allyl, 2'-O-aminoalkyl or 2'-deoxy-2'-fluoro group in nucleosides of an oligonucleotide confers enhanced hybridization properties to the oligonucleotide. Further, oligonucleotides containing phosphorothioate backbones have enhanced nuclease stability. Thus, functionalized, linked nucleosides of the invention can be augmented to include either or both a phosphorothioate backbone or a 2'-O-methyl, 2'-O-ethyl, 2'-O-propyl, 2'-O-aminoalkyl, 2'-O-allyl or 2'-fluoro group, In some preferred embodiments, functionalized nucleoside sequences of the invention possessing an amino group at the 5'-terminus are prepared using a DNA synthesizer, and then reacted with an active ester derivative of a selected ligand. Active ester derivatives are well known to those skilled in the art. Representative active esters include N-hydrosuccinimide esters, tetrafluorophenolic esters, pentafluorophenolic esters and pentachlorophenolic esters. The reaction of the amino group and the active ester produces an oligonucleotide in which the selected ligand is attached to the 5'-position through a linking group. The amino group at the 5'-terminus can be prepared utilizing a 5'-Amino-Modifier C6 reagent. In a preferred embodiment, ligand molecules may be conjugated to oligonucleotides at the 5'-position by the use of a ligand-nucleoside phosphoramidite wherein the ligand is linked to the 5'-hydroxy group directly or indirectly via a linker. Such ligand-nucleoside phosphoramidites are typically used at the end of an automated synthesis procedure to provide a ligand-conjugated oligonucleotide bearing the ligand at the 5'-terminus.

In one preferred embodiment of the methods of the invention, the preparation of ligand conjugated oligonucleotides commences with the selection of appropriate precursor molecules upon which to construct the ligand molecule. Typically, the precursor is an appropriately-protected derivative of the commonly-used nucleosides. For example, the synthetic precursors for the synthesis of the ligand-conjugated oligonucleotides of the invention include, but are not limited to, 2'-aminoalkoxy-5'-ODMT-nucleosides, 2'-6-aminoalkylamino-5'-ODMT-nucleosides, 5'-6-aminoalkoxy-2'-deoxy-nucleosides, 5'-6-aminoalkoxy-2-protected-nucleosides, 3'-6-aminoalkoxy-5'-ODMT-nucleosides, and 3'-aminoalkylamino-5'-ODMT-nucleosides that may be protected in the nucleobase portion of the molecule. Methods for the synthesis of such amino-linked protected nucleoside precursors are known to those of ordinary skill in the art.

In many cases, protecting groups are used during the preparation of the compounds of the invention. As used herein, the term "protected" means that the indicated moiety has a protecting group appended thereon. In some preferred embodiments of the invention, compounds contain one or more protecting groups. A wide variety of protecting groups can be employed in the methods of the invention. In general, protecting groups render chemical functionalities inert to specific reaction conditions, and can be appended to and removed from such functionalities in a molecule without substantially damaging the remainder of the molecule.

Representative hydroxyl protecting groups, for example, are disclosed by Beaucage et al. (*Tetrahedron*, 1992, 48:2223-2311). Further hydroxyl protecting groups, as well as other representative protecting groups, are disclosed in Greene and Wuts, *Protective Groups in Organic Synthesis*, Chapter 2, 2d ed., John Wiley & Sons, New York, 1991, and *Oligonucleotides And Analogues A Practical Approach*, Ekstein, F. Ed., IRL Press, N.Y, 1991.

Examples of hydroxyl protecting groups include, but are not limited to, t-butyl, t-butoxymethyl, methoxymethyl, tetrahydropyranyl, 1-ethoxyethyl, 1-(2-chloroethoxy)ethyl, 2-trimethylsilylethyl, p-chlorophenyl, 2,4-dinitrophenyl, benzyl, 2,6-dichlorobenzyl, diphenylmethyl, p,p'-dinitrobenzhydryl, p-nitrobenzyl, triphenylmethyl, trimethylsilyl, triethylsilyl, t-butyldimethylsilyl, t-butyldiphenylsilyl, triphenylsilyl, benzoylformate, acetate, chloroacetate, trichloroacetate, trifluoroacetate, pivaloate, benzoate, p-phenylbenzoate, 9-fluorenylmethyl carbonate, mesylate and tosylate.

Amino-protecting groups stable to acid treatment are selectively removed with base treatment, and are used to make reactive amino groups selectively available for substitution. Examples of such groups are the Fmoc (E. Atherton and R. C. Sheppard in *The Peptides*, S. Udenfriend, J. Meienhofer, Eds., Academic Press, Orlando, 1987, volume 9, p. 1)

and various substituted sulfonylethyl carbamates exemplified by the Nsc group (Samukov et al., *Tetrahedron Lett.*, 1994, 35:7821; Verhart and Tesser, *Rec. Trav. Chim. Pays-Bas*, 1987, 107:621).

Additional amino-protecting groups include, but are not limited to, carbamate protecting groups, such as 2-trimethylsilylethoxycarbonyl(Teoc), 1-methyl-1-(4-biphenylyl)ethoxycarbonyl (Bpoc), t-butoxycarbonyl (BOC), allyloxycarbonyl (Alloc), 9-fluorenylmethyloxycarbonyl (Fmoc), and benzyloxycarbonyl (Cbz); amide protecting groups, such as formyl, acetyl, trihaloacetyl, benzoyl, and nitrophenylacetyl; sulfonamide protecting groups, such as 2-nitrobenzenesulfonyl; and imine and cyclic imide protecting groups, such as phthalimido and dithiasuccinoyl. Equivalents of these amino-protecting groups are also encompassed by the compounds and methods of the invention.

Many solid supports are commercially available and one of ordinary skill in the art can readily select a solid support to be used in the solid-phase synthesis steps. In certain embodiments, a universal support is used. A universal support allows for preparation of oligonucleotides having unusual or modified nucleotides located at the 3'-terminus of the oligonucleotide. Universal Support 500 and Universal Support II are universal supports that are commercially available from Glen Research, 22825 Davis Drive, Sterling, Va. For further details about universal supports see Scott et al., *Innovations and Perspectives in solid-phase Synthesis*, 3rd *International Symposium*, 1994, Ed. Roger Epton, Mayflower Worldwide, 115-124]; Azhayev, A. V. *Tetrahedron* 1999, 55, 787-800; and Azhayev and Antopolsky *Tetrahedron* 2001, 57, 4977-4986. In addition, it has been reported that the oligonucleotide can be cleaved from the universal support under milder reaction conditions when oligonucleotide is bonded to the solid support via a syn-1,2-acetoxyphosphate group which more readily undergoes basic hydrolysis. See Guzaev, A. I.; Manoharan, M. *J. Am. Chem. Soc.* 2003, 125, 2380.

The nucleosides are linked by phosphorus-containing or non-phosphorus-containing covalent internucleoside linkages. For the purposes of identification, such conjugated nucleosides can be characterized as ligand-bearing nucleosides or ligand-nucleoside conjugates. The linked nucleosides having an aralkyl ligand conjugated to a nucleoside within their sequence will demonstrate enhanced dsRNA activity when compared to like dsRNA compounds that are not conjugated.

The aralkyl-ligand-conjugated oligonucleotides of the invention also include conjugates of oligonucleotides and linked nucleosides wherein the ligand is attached directly to the nucleoside or nucleotide without the intermediacy of a linker group. The ligand may preferably be attached, via linking groups, at a carboxyl, amino or oxo group of the ligand. Typical linking groups may be ester, amide or carbamate groups.

Specific examples of preferred modified oligonucleotides envisioned for use in the ligand-conjugated oligonucleotides of the invention include oligonucleotides containing modified backbones or non-natural internucleoside linkages. As defined here, oligonucleotides having modified backbones or internucleoside linkages include those that retain a phosphorus atom in the backbone and those that do not have a phosphorus atom in the backbone. For the purposes of the invention, modified oligonucleotides that do not have a phosphorus atom in their intersugar backbone can also be considered to be oligonucleosides.

Specific oligonucleotide chemical modifications are described below. It is not necessary for all positions in a given compound to be uniformly modified. Conversely, more than one modifications may be incorporated in a single dsRNA compound or even in a single nucleotide thereof.

Preferred modified internucleoside linkages or backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free-acid forms are also included.

Representative United States patents relating to the preparation of the above phosphorus-atom-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,625,050; and 5,697,248, each of which is herein incorporated by reference.

Preferred modified internucleoside linkages or backbones that do not include a phosphorus atom therein (i.e., oligonucleosides) have backbones that are formed by short chain alkyl or cycloalkyl intersugar linkages, mixed heteroatom and alkyl or cycloalkyl intersugar linkages, or one or more short chain heteroatomic or heterocyclic intersugar linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents relating to the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

In other preferred oligonucleotide mimetics, both the sugar and the internucleoside linkage, i.e., the backbone, of the nucleoside units are replaced with novel groups. The nucleobase units are maintained for hybridization with an appropriate nucleic acid target compound. One such oligonucleotide, an oligonucleotide mimetic, that has been shown to have excellent hybridization properties, is referred to as a peptide nucleic acid (PNA). In PNA compounds, the sugar-backbone of an oligonucleotide is replaced with an amide-containing backbone, in particular an aminoethylglycine backbone. The nucleobases are retained and are bound directly or indirectly to atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., *Science,* 1991, 254, 1497.

Some preferred embodiments of the invention employ oligonucleotides with phosphorothioate linkages and oligonucleosides with heteroatom backbones, and in particular —CH$_2$—NH—O—CH$_2$—, —CH$_2$—N(CH$_3$)—O—CH$_2$— [known as a methylene (methylimino) or MMI backbone], —CH$_2$—O—N(CH$_3$)—CH$_2$—, —CH$_2$—N(CH$_3$)—N(CH$_3$)—CH$_2$—, and —O—N(CH$_3$)—CH$_2$—CH$_2$— [wherein the native phosphodiester backbone is represented as —O—P—O—CH$_2$—] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

The oligonucleotides employed in the ligand-conjugated oligonucleotides of the invention may additionally or alternatively comprise nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C), and uracil (U). Modified nucleobases include other synthetic and natural nucleobases, such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine.

Further nucleobases include those disclosed in U.S. Pat. No. 3,687,808, those disclosed in the *Concise Encyclopedia Of Polymer Science And Engineering,* pages 858-859, Kroschwitz, J. I., ed. John Wiley & Sons, 1990, those disclosed by Englisch et al., *Angewandte Chemie, International Edition,* 1991, 30, 613, and those disclosed by Sanghvi, Y. S., Chapter 15, *Antisense Research and Applications,* pages 289-302, Crooke, S. T. and Lebleu, B., ed., CRC Press, 1993. Certain of these nucleobases are particularly useful for increasing the binding affinity of the oligonucleotides of the invention. These include 5-substituted pyrimidines, 6-azapyrimidines and N-2, N-6 and O-6 substituted purines, including 2-aminopropyladenine, 5-propynyluracil and 5-propynylcytosine. 5-Methylcytosine substitutions have been shown to increase nucleic acid duplex stability by 0.6-1.2° C. (Id., pages 276-278) and are presently preferred base substitutions, even more particularly when combined with 2'-methoxyethyl sugar modifications.

Representative United States patents relating to the preparation of certain of the above-noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,681,941; and 5,808,027; all of which are hereby incorporated by reference.

In certain embodiments, the oligonucleotides employed in the ligand-conjugated oligonucleotides of the invention may additionally or alternatively comprise one or more substituted sugar moieties. Preferred oligonucleotides comprise one of the following at the 2' position: OH; F; O—, S—, or N-alkyl, O-, S-, or N-alkenyl, or O, S- or N-alkynyl, wherein the alkyl, alkenyl and alkynyl may be substituted or unsubstituted C$_1$ to C$_{10}$ alkyl or C$_2$ to C$_{10}$ alkenyl and alkynyl. Particularly preferred are O[(CH$_2$)$_n$O]$_m$CH$_3$, O(CH$_2$)$_n$OCH$_3$, O(CH$_2$)$_n$NH$_2$, O(CH$_2$)$_n$CH$_3$, O(CH$_2$)$_n$ONH$_2$, and O(CH$_2$)$_n$ON[(CH$_2$)$_n$CH$_3$)]$_2$, where n and m are from 1 to about 10. Other preferred oligonucleotides comprise one of the following at the 2' position: C$_1$ to C$_{10}$ lower alkyl, substituted lower alkyl, alkaryl, aralkyl, O-alkaryl or O-aralkyl, SH, SCH$_3$, OCN, Cl, Br, CN, CF$_3$, OCF$_3$, SOCH$_3$, SO$_2$ CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. a preferred modification includes 2'-methoxyethoxy [2'-O—CH$_2$CH$_2$OCH$_3$, also known as 2'-O-(2-methoxyethyl) or 2'-MOE] (Martin et al., *Helv. Chim. Acta,* 1995, 78, 486), i.e., an alkoxyalkoxy group. A further preferred modification includes 2'-dimethylaminooxyethoxy, i.e., a O(CH$_2$)$_2$ON(CH$_3$)$_2$ group, also known as 2'-DMAOE, as described in U.S. Pat. No. 6,127,533, filed on Jan. 30, 1998, the contents of which are incorporated by reference.

Other preferred modifications include 2'-methoxy (2'-O—CH$_3$), 2'-aminopropoxy (2'-OCH$_2$CH$_2$CH$_2$NH$_2$) and 2'-fluoro (2'-F). Similar modifications may also be made at other positions on the oligonucleotide, particularly the 3' position of the sugar on the 3' terminal nucleotide or in 2'-5' linked oligonucleotides.

As used herein, the term "sugar substituent group" or "2'-substituent group" includes groups attached to the 2'-position of the ribofuranosyl moiety with or without an oxygen atom. Sugar substituent groups include, but are not limited to, fluoro, O-alkyl, O-alkylamino, O-alkylalkoxy, protected O-alkylamino, O-alkylaminoalkyl, O-alkyl imidazole and polyethers of the formula (O-alkyl)$_m$, wherein m is 1 to about 10. Preferred among these polyethers are linear and cyclic polyethylene glycols (PEGs), and (PEG)-containing groups, such as crown ethers and those which are disclosed by Ouchi et al. (Drug Design and Discovery 1992, 9:93); Ravasio et al. (*J. Org. Chem.* 1991, 56:4329); and Delgardo et. al. (*Critical Reviews in Therapeutic Drug Carrier Systems* 1992, 9:249), each of which is hereby incorporated by reference in its entirety. Further sugar modifications are disclosed by Cook (*Anti-Huntingtin disease Drug Design,* 1991, 6:585-607). Fluoro, O-alkyl, O-alkylamino, O-alkyl imidazole, O-alkylaminoalkyl, and alkyl amino substitution is described in U.S. Pat. No. 6,166,197, entitled "Oligomeric Compounds having Pyrimidine Nucleotide(s) with 2' and 5' Substitutions," hereby incorporated by reference in its entirety.

Additional sugar substituent groups amenable to the invention include 2'-SR and 2'-NR$_2$ groups, wherein each R is, independently, hydrogen, a protecting group or substituted or unsubstituted alkyl, alkenyl, or alkynyl. 2'-SR Nucleosides are disclosed in U.S. Pat. No. 5,670,633, hereby incorporated by reference in its entirety. The incorporation of 2'-SR monomer synthons is disclosed by Hamm et al. (*J. Org. Chem.*, 1997, 62:3415-3420). 2'-NR nucleosides are disclosed by Goettingen, M., *J. Org. Chem.*, 1996, 61, 6273-6281; and Polushin et al., *Tetrahedron Lett.*, 1996, 37, 3227-3230. Further representative 2'-substituent groups amenable to the invention include those having one of formula I or II:

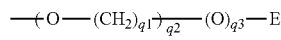

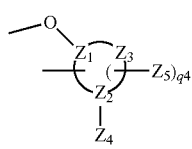

wherein,

E is $C_1$-$C_{10}$ alkyl, $N(Q_3)(Q_4)$ or $N=C(Q_3)(Q_4)$; each $Q_3$ and $Q_4$ is, independently, H, $C_1$-$C_{10}$ alkyl, dialkylaminoalkyl, a nitrogen protecting group, a tethered or untethered conjugate group, a linker to a solid support; or $Q_3$ and $Q_4$, together, form a nitrogen protecting group or a ring structure optionally including at least one additional heteroatom selected from N and O;

$q_1$ is an integer from 1 to 10;

$q_2$ is an integer from 1 to 10;

$q_3$ is 0 or 1;

$q_4$ is 0, 1 or 2;

each $Z_1$, $Z_2$ and $Z_3$ is, independently, $C_4$-$C_7$ cycloalkyl, $C_5$-$C_{14}$ aryl or $C_3$-$C_{15}$ heterocyclyl, wherein the heteroatom in said heterocyclyl group is selected from oxygen, nitrogen and sulfur;

$Z_4$ is $OM_1$, $SM_1$, or $N(M_1)_2$; each $M_1$ is, independently, H, $C_1$-$C_8$ alkyl, $C_1$-$C_8$ haloalkyl, $C(=NH)N(H)M_2$, $C(=O)N(H)M_2$ or $OC(=O)N(H)M_2$; $M_2$ is H or $C_1$-$C_8$ alkyl; and $Z_5$ is $C_1$-$C_{10}$ alkyl, $C_1$-$C_{10}$ haloalkyl, $C_2$-$C_{10}$ alkenyl, $C_2$-$C_{10}$ alkynyl, $C_6$-$C_{14}$ aryl, $N(Q_3)(Q_4)$, $OQ_3$, halo, $SQ_3$ or CN.

Representative 2'-O-sugar substituent groups of formula I are disclosed in U.S. Pat. No. 6,172,209, entitled "Capped 2'-Oxyethoxy Oligonucleotides," hereby incorporated by reference in its entirety. Representative cyclic 2'-O-sugar substituent groups of formula II are disclosed in U.S. Pat. No. 6,271,358, entitled "RNA Targeted 2'-Modified Oligonucleotides that are Conformationally Preorganized," hereby incorporated by reference in its entirety.

Sugars having O-substitutions on the ribosyl ring are also amenable to the invention. Representative substitutions for ring O include, but are not limited to, S, $CH_2$, CHF, and $CF_2$. See, e.g., Secrist et al., Abstract 21, *Program & Abstracts, Tenth International Roundtable, Nucleosides, Nucleotides and their Biological Applications*, Park City, Utah, Sep. 16-20, 1992.

Oligonucleotides may also have sugar mimetics, such as cyclobutyl moieties, in place of the pentofuranosyl sugar. Representative United States patents relating to the preparation of such modified sugars include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,0531 5,639,873; 5,646,265; 5,658,873; 5,670,633; 5,700,920; and 5,859,221, all of which are hereby incorporated by reference.

Additional modifications may also be made at other positions on the oligonucleotide, particularly the 3' position of the sugar on the 3' terminal nucleotide. For example, one additional modification of the ligand-conjugated oligonucleotides of the invention involves chemically linking to the oligonucleotide one or more additional non-ligand moieties or conjugates which enhance the activity, cellular distribution or cellular uptake of the oligonucleotide. Such moieties include but are not limited to lipid moieties, such as a cholesterol moiety (Letsinger et al., *Proc. Natl. Acad. Sci.* USA, 1989, 86, 6553), cholic acid (Manoharan et al., *Bioorg. Med. Chem. Lett.*, 1994, 4, 1053), a thioether, e.g., hexyl-S-tritylthiol (Manoharan et al., *Ann. N.Y. Acad. Sci.*, 1992, 660, 306; Manoharan et al., *Bioorg. Med. Chem. Let.*, 1993, 3, 2765), a thiocholesterol (Oberhauser et al., *Nucl. Acids Res.*, 1992, 20, 533), an aliphatic chain, e.g., dodecandiol or undecyl residues (Saison-Behmoaras et al., *EMBO J.*, 1991, 10, 111; Kabanov et al., *FEBS Lett.*, 1990, 259, 327; Svinarchuk et al., *Biochimie*, 1993, 75, 49), a phospholipid, e.g., di-hexadecyl-rac-glycerol or triethylammonium 1,2-di-O-hexadecyl-rac-glycero-3-H-phosphonate (Manoharan et al., *Tetrahedron Lett.*, 1995, 36, 3651; Shea et al., *Nucl. Acids Res.*, 1990, 18, 3777), a polyamine or a polyethylene glycol chain (Manoharan et al., *Nucleosides & Nucleotides*, 1995, 14, 969), or adamantane acetic acid (Manoharan et al., *Tetrahedron Lett.*, 1995, 36, 3651), a palmityl moiety (Mishra et al., *Biochim. Biophys. Acta*, 1995, 1264, 229), or an octadecylamine or hexylaminocarbonyl-oxycholesterol moiety (Crooke et al., *J. Pharmacol. Exp. Ther.*, 1996, 277, 923).

Representative United States patents relating to the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928; and 5,688,941, each of which is herein incorporated by reference.

The invention also includes compositions employing oligonucleotides that are substantially chirally pure with regard to particular positions within the oligonucleotides. Examples of substantially chirally pure oligonucleotides include, but are not limited to, those having phosphorothioate linkages that are at least 75% Sp or Rp (Cook et al., U.S. Pat. No. 5,587,361) and those having substantially chirally pure (Sp or Rp) alkylphosphonate, phosphoramidate or phosphotriester linkages (Cook, U.S. Pat. Nos. 5,212,295 and 5,521,302).

In certain instances, the oligonucleotide may be modified by a non-ligand group. A number of non-ligand molecules have been conjugated to oligonucleotides in order to enhance the activity, cellular distribution or cellular uptake of the oligonucleotide, and procedures for performing such conjugations are available in the scientific literature. Such non-ligand moieties have included lipid moieties, such as cholesterol (Letsinger et al., *Proc. Natl. Acad. Sci. USA*, 1989, 86:6553), cholic acid (Manoharan et al., *Bioorg. Med. Chem. Lett.*, 1994, 4:1053), a thioether, e.g., hexyl-S-tritylthiol (Manoharan et al., *Ann. N.Y. Acad. Sci.*, 1992, 660:306; Manoharan et al., *Bioorg. Med. Chem. Let.*, 1993, 3:2765), a thiocholesterol (Oberhauser et al., *Nucl. Acids Res.*, 1992, 20:533), an aliphatic chain, e.g., dodecandiol or undecyl residues (Saison-Behmoaras et al., *EMBO J.*, 1991, 10:111; Kabanov et al., *FEBS Lett.*, 1990, 259:327; Svinarchuk et al., *Biochimie*, 1993, 75:49), a phospholipid, e.g., di-hexadecyl-rac-glycerol or triethylammonium 1,2-di-O-hexadecyl-rac-glycero-3-H-phosphonate (Manoharan et al., *Tetrahedron Lett.*, 1995, 36:3651; Shea et al., *Nucl. Acids Res.*, 1990, 18:3777), a polyamine or a polyethylene glycol chain (Manoharan et al., *Nucleosides & Nucleotides*, 1995, 14:969), or adamantane acetic acid (Manoharan et al., *Tetrahedron Lett.*, 1995, 36:3651), a palmityl moiety (Mishra et al., *Biochim. Biophys. Acta*, 1995, 1264:229), or an octadecylamine or hexylamino-carbonyl-oxycholesterol moiety (Crooke et al., *J. Pharmacol. Exp. Ther.*, 1996, 277:923). Representative United States patents that teach the preparation of such oligonucleotide conjugates have been listed above. Typical conjugation protocols involve the synthesis of oligonucleotides bearing an aminolinker at one or more positions of the sequence. The amino group is then reacted with the molecule being conjugated using appropriate coupling or activating reagents. The conjugation reaction may be performed either with the oligonucleotide still bound to the solid support or following cleavage of the oligonucleotide in solution phase. Purification of the oligonucleotide conjugate by HPLC typically affords the pure conjugate.

Alternatively, the molecule being conjugated may be converted into a building block, such as a phosphoramidite, via an alcohol group present in the molecule or by attachment of a linker bearing an alcohol group that may be phosphitylated.

Importantly, each of these approaches may be used for the synthesis of ligand conjugated oligonucleotides. Amino-linked oligonucleotides may be coupled directly with ligand via the use of coupling reagents or following activation of the ligand as an NHS or pentfluorophenolate ester. Ligand phosphoramidites may be synthesized via the attachment of an aminohexanol linker to one of the carboxyl groups followed by phosphitylation of the terminal alcohol functionality. Other linkers, such as cysteamine, may also be utilized for conjugation to a chloroacetyl linker present on a synthesized oligonucleotide.

III. PHARMACEUTICAL COMPOSITIONS COMPRISING dsRNA

In one embodiment, the invention provides pharmaceutical compositions comprising a dsRNA, as described in the preceding section, and a pharmaceutically acceptable carrier, as described below. The pharmaceutical composition comprising the dsRNA is useful for treating a disease or disorder associated with the expression or activity of the HD gene.

In another embodiment, the invention provides pharmaceutical compositions comprising at least two dsRNAs, designed to target different regions of the HD gene, and a pharmaceutically acceptable carrier. In this embodiment, the individual dsRNAs are prepared as described in the preceding section, which is incorporated by reference herein. One dsRNA can have a nucleotide sequence which is substantially complementary to at least one part of the HD gene; additional dsRNAs are prepared, each of which has a nucleotide sequence that is substantially complementary to different part of the HD gene. The multiple dsRNAs may be combined in the same pharmaceutical composition, or formulated separately. If formulated individually, the compositions containing the separate dsRNAs may comprise the same or different carriers, and may be administered using the same or different routes of administration. Moreover, the pharmaceutical compositions comprising the individual dsRNAs may be administered substantially simultaneously, sequentially, or at preset intervals throughout the day or treatment period.

The pharmaceutical compositions of the invention are administered in dosages sufficient to inhibit expression of the HD gene. The present inventors have found that, because of their improved efficiency, compositions comprising the dsRNA of the invention can be administered at surprisingly low dosages. A maximum dosage of 5 mg dsRNA per kilogram body weight of recipient per day is sufficient to inhibit or completely suppress expression of the HD gene.

In general, a suitable dose of dsRNA will be in the range of 0.01 to 5.0 milligrams per kilogram body weight of the recipient per day, preferably in the range of 0.1 to 200 micrograms per kilogram body weight per day, more preferably in the range of 0.1 to 100 micrograms per kilogram body weight per day, even more preferably in the range of 1.0 to 50 micrograms per kilogram body weight per day, and most preferably in the range of 1.0 to 25 micrograms per kilogram body weight per day. The pharmaceutical composition may be administered once daily, or the dsRNA may be administered as two, three, four, five, six or more sub-doses at appropriate intervals throughout the day. In that case, the dsRNA contained in each sub-dose must be correspondingly smaller in order to achieve the total daily dosage. The dosage unit can also be compounded for delivery over several days, e.g., using a conventional sustained release formulation which provides sustained release of the dsRNA over a several day period. Sustained release formulations are well known in the art. In this embodiment, the dosage unit contains a corresponding multiple of the daily dose.

The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a composition can include a single treatment or a series of treatments. Estimates of effective dosages and in vivo half-lives for the individual dsRNAs encompassed by the invention can be made using conventional methodologies or on the basis of in vivo testing using an appropriate animal model, as described elsewhere herein.

Advances in mouse genetics have generated a number of mouse models for the study of various human diseases, such as Huntington's disease. Such models are used for in vivo testing of dsRNA, as well as for determining a therapeutically effective dose.

The pharmaceutical compositions encompassed by the invention may be administered by any means known in the art including, but not limited to oral or parenteral routes, including intracranial (including intraparenchymal and intraventricular), intrathecal, epidural, intravenous, intramuscular, intraperitoneal, subcutaneous, transdermal, airway (aerosol), nasal, rectal, vaginal and topical (including buccal and sublingual) administration. In preferred embodiments, the pharmaceutical compositions are administered by intravenous, intrathecal or intracranial infusion or injection.

For intramuscular, intracranial, intrathecal, subcutaneous and intravenous use, the pharmaceutical compositions of the invention will generally be provided in sterile aqueous solutions or suspensions, buffered to an appropriate pH and isotonicity. Suitable aqueous vehicles include Ringer's solution and isotonic sodium chloride. In a preferred embodiment, the carrier consists exclusively of an aqueous buffer. In this context, "exclusively" means no auxiliary agents or encapsulating substances are present which might affect or mediate uptake of dsRNA in the cells that express the HD gene. Such substances include, for example, micellar structures, such as liposomes or capsids, as described below. Surprisingly, the present inventors have discovered that compositions containing only naked dsRNA and a physiologically acceptable solvent are taken up by cells, where the dsRNA effectively inhibits expression of the HD gene. Although microinjection, lipofection, viruses, viroids, capsids, capsoids, or other auxiliary agents are required to introduce dsRNA into cell cultures, surprisingly these methods and agents are not necessary for uptake of dsRNA in vivo. Aqueous suspensions according to the invention may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

The pharmaceutical compositions useful according to the invention also include encapsulated formulations to protect the dsRNA against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811; PCT publication WO 91/06309; and European patent publication EP-A-43075, which are incorporated by reference herein.

Using the small interfering RNA vectors previously described, the invention also provides devices, systems, and methods for delivery of small interfering RNA to target locations of the brain. The envisioned route of delivery is through the use of implanted, indwelling, intraparenchymal catheters that provide a means for injecting small volumes of fluid containing the dsRNA of the invention directly into local brain tissue. Another envisioned route of delivery is through the use of implanted, indwelling, intraventricular catheters that provide a means for injecting small volumes of fluid containing the dsRNA of the invention directly into cerebrospinal fluid. The proximal end of these catheters may be connected to an implanted, intracerebral access port surgically affixed to the patient's cranium, or to an implanted drug pump located in the patient's torso.

Alternatively, implantable delivery devices, such as an implantable pump may be employed. Examples of the delivery devices within the scope of the invention include the Model 8506 investigational device (by Medtronic, Inc. of Minneapolis, Minn.), which can be implanted subcutaneously on the cranium, and provides an access port through which therapeutic agents may be delivered to the brain. Delivery occurs through a stereotactically implanted polyurethane catheter. Two models of catheters that can function with the Model 8506 access port include the Model 8770 ventricular catheter by Medtronic, Inc., for delivery to the intracerebral ventricles, which is disclosed in U.S. Pat. No. 6,093,180, incorporated herein by reference, and the IPA1 catheter by Medtronic, Inc., for delivery to the brain tissue itself (i.e., intraparenchymal delivery), disclosed in U.S. Ser. Nos. 09/540,444 and 09/625,751, which are incorporated herein by reference. The latter catheter has multiple outlets on its distal end to deliver the therapeutic agent to multiple sites along the catheter path. In addition to the aforementioned device, the delivery of the small interfering RNA vectors in accordance with the invention can be accomplished with a wide variety of devices, including but not limited to U.S. Pat. Nos. 5,735,814, 5,814,014, and 6,042,579, all of which are incorporated herein by reference. Using the teachings of the invention and those of skill in the art will recognize that these and other devices and systems may be suitable for delivery of small interfering RNA vectors for the treatment of neurodegenerative diseases in accordance with the invention.

In one such embodiment, the method further comprises the steps of implanting a pump outside the brain, the pump coupled to a proximal end of the catheter, and operating the pump to deliver the predetermined dosage of the at least one small interfering RNA or small interfering RNA vector through the discharge portion of the catheter. A further embodiment comprises the further step of periodically refreshing a supply of the at least one small interfering RNA or small interfering RNA vector to the pump outside said brain.

Thus, the invention includes the delivery of small interfering RNA vectors using an implantable pump and catheter, like that taught in U.S. Pat. Nos. 5,735,814 and 6,042,579, and further using a sensor as part of the infusion system to regulate the amount of small interfering RNA vectors delivered to the brain, like that taught in U.S. Pat. No. 5,814,014. Other devices and systems can be used in accordance with the method of the invention, for example, the devices and systems disclosed in U.S. Ser. Nos. 09/872,698 (filed Jun. 1, 2001) and 09/864,646 (filed May 23, 2001), which are incorporated herein by reference.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred.

The data obtained from cell culture assays and animal studies can be used in formulation a range of dosage for use in humans. The dosage of compositions of the invention lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range of the compound or, when appropriate, of the polypeptide product of a target sequence (e.g., achieving a decreased concentration of the polypeptide) that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

In addition to their administration individually or as a plurality, as discussed above, the dsRNAs of the invention can be administered in combination with other known agents effective in treatment of diseases. In any event, the administering physician can adjust the amount and timing of dsRNA administration on the basis of results observed using standard measures of efficacy known in the art or described herein.

Methods for Treating Diseases Caused by Expression of the HD Gene

In one embodiment, the invention provides a method for treating a subject having a disease or at risk of developing a disease caused by the expression of the HD gene, or a mutant form of the HD gene. In this embodiment, the dsRNA acts as a therapeutic agent for controlling the expression of the HD protein. The method comprises administering a pharmaceutical composition of the invention to the patient (e.g., human), such that expression of the HD gene is diminished at least in part. Because of their high specificity, the dsRNAs of the invention specifically target mRNAs of the HD gene.

Neurodegenerative Diseases

Huntington's disease is also known as Huntington's Chorea, Chronic Progressive Chorea, and Hereditary Chorea. Huntington's disease is an autosomal dominant genetic disorder characterized by choreiform movements and progressive intellectual deterioration, usually beginning in middle age (35 to 50 yr). The disease affects both sexes equally. The caudate nucleus atrophies, the small-cell population degenerates, and levels of the neurotransmitters gamma-aminobutyric acid (GABA) and substance P decrease. This degeneration results in characteristic "boxcar ventricles" seen on CT scans.

The gene involved in Huntington's disease (IT-15) is located at the end of the short arm of chromosome 4. A mutation occurs in the coding region of this gene and produces an unstable expanded trinucleotide repeat (cytosine-adenosine-guanosine), resulting in a protein with an expanded glutamate sequence. The normal and abnormal functions of this protein (termed huntingtin) are unknown. The abnormal huntingtin protein appears to accumulate in neuronal nuclei of transgenic mice, but the causal relationship of this accumulation to neuronal death is uncertain.

By "Huntingtin" or "HD" as used herein is meant, any Huntingtin protein, peptide, or polypeptide associated with the development or maintenance of Huntington disease. The terms "Huntingtin" and "HD" also refer to nucleic acid sequences encoding any huntingtin protein, peptide, or polypeptide, such as Huntingtin RNA or Huntingtin DNA (see for example Van Dellen et al., Jan. 24, 2004, Neurogenetics).

Symptoms and signs develop insidiously. Dementia or psychiatric disturbances, ranging from apathy and irritability to full-blown bipolar or schizophreniform disorder, may precede the movement disorder or develop during its course. Anhedonia or asocial behavior may be the first behavioral manifestation. Motor manifestations include flicking movements of the extremities, a lilting gait, motor impersistence (inability to sustain a motor act, such as tongue protrusion), facial grimacing, ataxia, and dystonia.

Treatment for Huntington's disease is currently not available. The choreic movements and agitated behaviors may be suppressed, usually only partially, by antipsychotics (e.g., chlorpromazine 100 to 900 mg/day po or haloperidol 10 to 90 mg/day po) or reserpine begun with 0.1 mg/day po and increased until adverse effects of lethargy, hypotension, or parkinsonism occur.

Another embodiment of the present invention thus provides the use of an anti-Huntingtin dsRNA administered to a human, particularly the striatum of the human brain, for the treatment of Huntington's disease The pharmaceutical compositions encompassed by the invention may be administered by any means known in the art including, but not limited to oral or parenteral routes, including intracranial (including intraparenchymal and intraventricular), intrathecal, epidural, intravenous, intramuscular, intraperitoneal, subcutaneous, transdermal, airway (aerosol), nasal, rectal, vaginal and topical (including buccal and sublingual) administration. In preferred embodiments, the pharmaceutical compositions are administered by intravenous, intrathecal or intracranial infusion or injection.

Methods for Inhibiting Expression of the HD Gene

In yet another aspect, the invention provides a method for inhibiting the expression of the HD gene in a mammal. The method comprises administering a composition of the invention to the mammal such that expression of the target HD gene is silenced. Because of their high specificity, the dsRNAs of the invention specifically target RNAs (primary or processed) of target HD gene. Compositions and methods for inhibiting the expression of these HD genes using dsRNAs can be performed as described elsewhere herein.

In one embodiment, the method comprises administering a composition comprising a dsRNA, wherein the dsRNA comprises a nucleotide sequence which is complementary to at least a part of an RNA transcript of the HD gene of the mammal to be treated. When the organism to be treated is a mammal such as a human, the composition may be administered by any means known in the art including, but not limited to oral or parenteral routes, including intracranial (including intraparenchymal and intraventricular), intrathecal, epidural, intravenous, intramuscular, intracranial, subcutaneous, transdermal, airway (aerosol), nasal, rectal, vaginal and topical (including buccal and sublingual) administration. In preferred embodiments, the compositions are administered by intravenous, intrathecal or intracranial infusion or injection.

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Examples

Gene Walking of the HD Gene

ClustalW multiple alignment function of BioEdit Sequence Alignment Editor (version 7.0.4.1) was used to generate a global alignment of human (NM-002111), mouse (NM_010414) and rat (U18650) mRNA sequences.

Conserved regions were identified by embedded sequence analysis function of the software. Conserved regions were defined as sequence stretches with a minimum length of 19 bases for all aligned sequences containing no internal gaps. Sequence positions of conserved regions were counted according to the human sequence.

The siRNA design web interface at Whitehead Institute for Biomedical Research (http://jura.wi.mit.edu/siRNAext/) (Yuan et al., Nucl. Acids. Res. 2004 32:W130-W134) was used to identify all potential siRNAs targeting the conserved regions as well as their respective off-target hits to sequences in the human, mouse and rat RefSeq database. siRNAs satisfying the cross-reactivity criteria selected out of the candidates pool and subjected to the software embedded off-target analysis. For this, all selected siRNAs were analyzed in 3 rounds by the NCBI blast algorithm against the NCBI human, mouse and rat RefSeq database.

Blast results were downloaded and analyzed in order to extract the identity of the best off-target hit for the antisense strand as well as the positions of occurring mismatches. All siRNA candidates were ranked according to predicted properties. For this, different criteria were applied in order to identify siRNA with the following properties: targeting human, mouse and rat sequences (cross-reactivity given), absence of stretches with more than 3 Gs in a row, absence of human, mouse or rat predicted off-target hits. The siRNAs that contained the applied criteria were selected and synthesized (Tables 1 and 2).

As has been experienced by those working in the antisense field, ribonucleic acids are often quickly degraded by a range of nucleases present in virtually all biological environments, e.g. endonucleases, exonucleases etc. This vulnerability may be circumvented by chemically modifying these oligonucleotides such that nucleases may no longer attack. Consequently, siRNAs were synthesized with 2'-O-Methyl substitutions (Table 2) and tested for in vitro inhibitory activity on endogenous HD gene expression (HD mRNA levels).

TABLE 1

Sequences and activities of dsRNAs tested for HD gene expression inhibiting activity

| Duplex name | sequence of total 19mer target site | SEQ ID NO: | Sense strand sequence (5'-3') | SEQ ID NO: | Antisense strand sequence (5'-3') | SEQ ID NO: | Remaining HD gene mRNA [% of control] |
|---|---|---|---|---|---|---|---|
| AD-10894 | gaaucgagaucggauguca | 1 | gaaucgagaucggaugucaTT | 2 | ugacauccgaucucgauucTT | 3 | 28 ± 3 |
| AD-10895 | aaauccugcuuuagucgag | 4 | aaauccugcuuuagucgagTT | 5 | cucgacuaaagcaggauuuTT | 6 | 45 ± 4 |
| AD-10896 | agucaguccggguagaacu | 7 | agucaguccggguagaacuTT | 8 | aguucuacccggacugacuTT | 9 | 38 ± 2 |
| AD-10897 | gguuuaugaacugacguua | 10 | gguuuaugaacugacguuaTT | 11 | uaacgucaguucauaaaccTT | 12 | 11 ± 2 |
| AD-10898 | guuacggguuaauuacugu | 13 | guuacggguuaauuacuguTT | 14 | acaguaauuaacccguaacTT | 15 | 28 ± 1 |
| AD-10899 | ugcuuuagucgagaaccaa | 16 | ugcuuuagucgagaaccaaTT | 17 | uugguucucgacuaaagcaTT | 18 | 33 ± 3 |
| AD-10900 | ucuguaccguugaguccca | 19 | ucuguaccguugagucccaTT | 20 | ugggacucaacgguacagaTT | 21 | 35 ± 3 |
| AD-10901 | aaauuguguuagacgguac | 22 | aaauuguguuagacgguacTT | 23 | guaccgucuaacacaauuuTT | 24 | 48 ± 6 |
| AD-10902 | uggccggaaacuugcuugc | 25 | uggccggaaacuugcuugcTT | 26 | gcaagcaaguuuccggccaTT | 27 | 46 ± 5 |
| AD-10903 | guucaguuacggguuaauu | 28 | guucaguuacggguuaauuTT | 29 | aauuaacccguaacugaacTT | 30 | 32 ± 3 |
| AD-10904 | gcgggcucguuccaugauc | 31 | gcgggcucguuccaugaucTT | 32 | gaucauggaacgagcccgcTT | 33 | 31 ± 1 |
| AD-10905 | gacuccgagcacuuaacgu | 34 | gacuccgagcacuuaacguTT | 35 | acgucaagugcucggagucTT | 36 | 28 ± 3 |
| AD-10906 | cgcauggucgacauccuug | 37 | cgcauggucgacauccuugTT | 38 | caaggaugucgaccaugcgTT | 39 | 37 ± 2 |
| AD-10907 | aagacgagauccucgcuca | 40 | aagacgagauccucgcucaTT | 41 | ugagcgaggaucucgucuuTT | 42 | 35 ± 1 |
| AD-10908 | aagucaguccggguagaac | 43 | aagucaguccggguagaacTT | 44 | guucuacccggacugacuuTT | 45 | 42 ± 4 |
| AD-10909 | aaggccuucauagcgaacc | 46 | aaggccuucauagcgaaccTT | 47 | gguucgcuaugaaggccuuTT | 48 | 65 ± 4 |

TABLE 1-continued

Sequences and activities of dsRNAs tested for HD gene expression inhibiting activity

| Duplex name | sequence of total 19mer target site | SEQ ID NO: | Sense strand sequence (5'-3') | SEQ ID NO: | Antisense strand sequence (5'-3') | SEQ ID NO: | Remaining HD gene mRNA [% of control] |
|---|---|---|---|---|---|---|---|
| AD-10910 | aggccuucauagcgaaccu | 49 | aggccuucauagcgaaccuTT | 50 | agguucgcuaugaaggccuTT | 51 | 23 ± 1 |
| AD-10911 | acuccgagcacuuaacgug | 52 | acuccgagcacuuaacgugTT | 53 | cacguuaagugcucggaguTT | 54 | 42 ± 4 |
| AD-10912 | uaacggccuucauagcgaa | 55 | uaaaggccuucauagcgaaTT | 56 | uucgcuaugaaggccuuuaTT | 57 | 20 ± 1 |
| AD-10913 | ucugaaucgagaucggaug | 58 | ucugaaucgagaucggaugTT | 59 | cauccgaucucgauucagaTT | 60 | 46 ± 4 |
| AD-10914 | ugaaauuguguuagacggu | 61 | ugaaauuguguuagacgguTT | 62 | accgucuaacacaauuucaTT | 63 | 35 ± 1 |
| AD-10915 | uggcucgcauggucgacau | 64 | uggcucgccuggucgacauTT | 65 | augucgaccaugcgagccaTT | 66 | 42 ± 5 |
| AD-10916 | aaagucaguccggguagaa | 67 | aaagucaguccggguagaaTT | 68 | uucuacccggacugacuuuTT | 69 | 42 ± 4 |
| AD-10917 | gagugcccgugucgguucu | 70 | gagugcccgugucgguucuTT | 71 | agaaccgacacgggcacucTT | 72 | 77 ± 8 |
| AD-10918 | ggagcucgggacggauagu | 73 | ggagcucgggacggauaguTT | 74 | acuauccguccccgagcuccTT | 75 | 94 ± 9 |
| AD-10919 | agaaaacaagccuugccgc | 76 | agaaaacaagccuugccgcTT | 77 | gcggcaaggcuuguuuucuTT | 78 | 43 ± 4 |
| AD-10920 | auaaucacauucguuuguu | 79 | auaaucacauucguuuguuTT | 80 | aacaaacgaaugugauuauTT | 81 | 35 ± 4 |
| AD-10921 | ucugggcaucgcuauggaa | 82 | ucugggcaucgcuauggaaTT | 83 | uuccauagcgaugcccagaTT | 84 | 26 ± 6 |
| AD-10922 | ggccuucauagcgaaccug | 85 | ggccuucauagcgaaccugTT | 86 | cagguucgcuaugaaggccTT | 87 | 32 ± 12 |
| AD-10923 | cuaaaugugcucuuaggcu | 88 | cuaaaugugcucuuaggcuTT | 89 | agccuaagagcacauuuagTT | 90 | 24 ± 8 |
| AD-10924 | guuuaugaacugacguuac | 91 | guuuaugaacugacguuacTT | 92 | guaacgucaguucauaaacTT | 93 | 18 ± 8 |
| AD-10925 | uuuaugaacugacguuaca | 94 | uuuaugaacugacguuacaTT | 95 | uguaacgucaguucauaaaTT | 96 | 25 ± 3 |
| AD-10926 | augaacugacguuacauca | 97 | augaacugacguuacaucaTT | 98 | ugauguaacgucaguucauTT | 99 | 20 ± 3 |
| AD-10927 | ccacaauguugugaccgga | 100 | ccacaauguugugaccggaTT | 101 | uccggucacaacauuguggTT | 102 | 20 ± 3 |
| AD-10928 | cugguggccgaagccguag | 103 | cugguggccgaagccguagTT | 104 | cuacggcuucggccaccagTT | 105 | 38 ± 1 |
| AD-10929 | aauuguguuagacgguacc | 106 | aauuguguuagacgguaccTT | 107 | gguaccgucuaacacaauuTT | 108 | 39 ± 6 |
| AD-10930 | uuguguuagacgguaccga | 109 | uuguguuagacgguaccgaTT | 110 | ucgguaccgcucuaacacaaTT | 111 | 30 ± 4 |
| AD-10931 | aaaacaagccuugccgcau | 112 | aaaacaagccuugccgcauTT | 113 | augcggcaaggcuuguuuuTT | 114 | 32 ± 3 |
| AD-10932 | aagagcuguaccguuggga | 115 | aagagcuguaccguugggaTT | 116 | ucccaacgguacagcucuuTT | 117 | 43 ± 5 |
| AD-10933 | auaccucagguccuguuac | 118 | auaccucagguccuguuacTT | 119 | guaacaggaccugagguauTT | 120 | 36 ± 4 |
| AD-10934 | uccugcuuuagucgagaac | 121 | uccugcuuuagucgagaacTT | 122 | guucucgacuaaagcaggaTT | 123 | 35 ± 7 |
| AD-10935 | cauaaucacauucguuugu | 124 | cauaaucacauucguuuguTT | 125 | acaaacgaaugugauuaugTT | 126 | 28 ± 2 |
| AD-10936 | aagcgacugucucgacaga | 127 | aagcgacugucucgacagaTT | 128 | ucugucgagacagucgcuuTT | 129 | 29 ± 3 |
| AD-10937 | ccgagcacuuaacguggcu | 130 | ccgagcacuuaacguggcuTT | 131 | agccacguuaagugcucggTT | 132 | 38 ± 5 |
| AD-10938 | cuggcucgcauggucgaca | 133 | cuggcucgcauggucgacaTT | 134 | ugucgaccaugcgagccagTT | 135 | 35 ± 2 |
| AD-10939 | uugucgccggguagaaaag | 136 | uugucgccggguagaaaagTT | 137 | cauuucuacccggcgacaaTT | 138 | 47 ± 8 |
| AD-10940 | ugcaagacucacuuagucc | 139 | ugcaagacucacuuaguccTT | 140 | ggacuaagugagucuugcaTT | 141 | 56 ± 9 |
| AD-10941 | gaaacaguguguccggaca | 142 | gcaacaguguguccggacaTT | 143 | uguccggacucacuguuucTT | 144 | 36 ± 4 |
| AD-10942 | aaaucccaguguuggacca | 145 | aaaucccaguguuggaccaTT | 146 | ugguccaacacugggauuuTT | 147 | 37 ± 4 |
| AD-10943 | gcuagcuccaugcuuaagc | 148 | gcuagcuccaugcuuaagcTT | 149 | gcuuaagcauggagcuagcTT | 150 | 47 ± 4 |
| AD-10944 | uccaugcuuaagccuaggg | 151 | uccaugcuuaagccuagggTT | 152 | cccuaggcuuaagcauggaTT | 153 | 102 ± 12 |
| AD-10945 | ccaugcuuaagccuaggga | 154 | ccaugcuuaagccuagggaTT | 155 | ucccuaggcuuaagcauggTT | 156 | 34 ± 5 |
| AD-10946 | ucaacagcuacacacgugu | 157 | ucaacagcuacacacguguTT | 158 | acacguguguagcuguugaTT | 159 | 40 ± 5 |

TABLE 1-continued

Sequences and activities of dsRNAs tested for HD gene expression inhibiting activity

| Duplex name | sequence of total 19mer target site | SEQ ID NO: | Sense strand sequence (5'-3') | SEQ ID NO: | Antisense strand sequence (5'-3') | SEQ ID NO: | Remaining HD gene mRNA [% of control] |
|---|---|---|---|---|---|---|---|
| AD-10947 | augugugccacugcguuuu | 160 | augugugccacugcguuuuTT | 161 | aaaacgcaguggcacacauTT | 162 | 31 ± 3 |
| AD-10948 | ugugugccacugcguuuua | 163 | ugugugccacugcguuuuaTT | 164 | uaaaacgcaguggcacacaTT | 165 | 33 ± 1 |
| AD-10949 | ucaguccggguagaacuuc | 166 | ucaguccggguagaccuucTT | 167 | gaaguucuacccggacugaTT | 168 | 58 ± 5 |
| AD-10950 | aguccggguagaacuucag | 169 | aguccggguagaacuucagTT | 170 | cugaaguucuacccggacuTT | 171 | 34 ± 3 |
| AD-10951 | gauuguugcuauggagcgg | 172 | gauuguugcuauggagcggTT | 173 | ccgcuccauagcaacaaucTT | 174 | 46 ± 7 |
| AD-10952 | acuuguuuacgaaaugucc | 175 | acuuguuuacgaaauguccTT | 176 | ggacauuucguaaacaaguTT | 177 | 46 ± 2 |
| AD-10953 | cuuguuuacgaaaugucca | 178 | cuuguuuacgaaauguccaTT | 179 | uggacauuucguaaacaagTT | 180 | 30 ± 1 |
| AD-10954 | gcuuccgcacaugccgcgg | 181 | gcuuccgcacaugccgcggTT | 182 | ccgcggcaugugcggaagcTT | 183 | 45 ± 5 |
| AD-10955 | uaauuuuaacguaacucuu | 184 | uaauuuuaacguaacucuuTT | 185 | aagaguuacguuaaaauuaTT | 186 | 104 ± 6 |
| AD-10956 | cuuucuaugcccguguaaa | 187 | cuuucuaugcccguguaaaTT | 188 | uuuacacgggcauagaaagTT | 189 | 59 ± 3 |
| AD-10957 | aaagggaaggacugacgag | 190 | aaagggaaggacugacgagTT | 191 | cucgucagucccuucccuuuTT | 192 | 84 ± 4 |
| AD-10958 | gcuggcucgcauggucgac | 193 | gcuggcucgcauggucgacTT | 194 | gucgaccaugcgagccagcTT | 195 | 44 ± 4 |
| AD-10959 | ugacguuacaucauacaca | 196 | ugacguuacaucauacacaTT | 197 | uguauigauguaacgucaTT | 198 | 19 ± 3 |
| AD-10960 | acgguaccgacaaccagua | 199 | acgguaccgacaaccaguaTT | 200 | uacugguugucgguaccguTT | 201 | 25 ± 3 |
| AD-10961 | gguaccgacaaccaguauu | 202 | gguaccgacaaccaguauuTT | 203 | aauacugguugucgguaccTT | 204 | 19 ± 3 |
| AD-10962 | acgagugcucaauaauguu | 205 | acgagugcucaauaauguuTT | 206 | aacauuauugagcacucguTT | 207 | 19 ± 3 |
| AD-10963 | caucggagaguuucugucc | 208 | caucggagaguuucuguccTT | 209 | ggacagaaacucuccgaugTT | 210 | 38 ± 5 |
| AD-10964 | gcgaaccugaagucaagcu | 211 | gcgaaccugaagucaagcuTT | 212 | agcuugacuucagguucgcTT | 213 | 35 ± 4 |
| AD-10965 | cugaaucgagaucggaugu | 214 | cugaaucgagaucggauguTT | 215 | acauccgaucucgauucagTT | 216 | 31 ± 2 |
| AD-10966 | cgguaccgacaaccaguau | 217 | cgguaccgacaaccaguauTT | 218 | auacugguugucgguaccgTT | 219 | 26 ± 2 |
| AD-10967 | acugaaccggguugaucaag | 220 | acugaaccggguugaucaagTT | 221 | cuugaucacccgguucaguTT | 222 | 43 ± 3 |
| AD-10968 | ccuugccgcaucaaaggug | 223 | ccuugccgcaucaaaggugTT | 224 | caccuuugaugcggcaaggTT | 225 | 64 ± 9 |
| AD-10969 | cuuggcggauugcauucc | 226 | cuu+ggcggauugcauuccTT | 227 | ggaaugcaauccgccaaagTT | 228 | 45 ± 3 |
| AD-10970 | cuguaccguugagucccaa | 229 | cuguaccguugagucccaaTT | 230 | uugggacucaacgguacagTT | 231 | 33 ± 1 |
| AD-10971 | uguaccguugagucccaag | 232 | uguaccguugagucccaagTT | 233 | cuugggacucaacgguacaTT | 234 | 36 ± 4 |
| AD-10972 | agucgagaaccaaugaugg | 235 | agucgagaaccaaugauggTT | 236 | ccaucauugguucucgacuTT | 237 | 34 ± 5 |
| AD-10973 | ccgacuaccgcuggugggc | 238 | ccgacuaccgcuggugggcTT | 239 | gcccaccagcgguagucggTT | 240 | 47 ± 7 |
| AD-10974 | auaucaccggcugcugacu | 241 | auaucaccggcugcugacuTT | 242 | agucagcagccggugauauTT | 243 | 73 ± 6 |
| AD-10975 | ugcauaucgcugggcucaa | 244 | ugcauaucgcugggcucaaTT | 245 | uugagcccagcgauaugcaTT | 246 | 88 ± 1 |
| AD-10976 | uuguuuacgacgugaucua | 247 | uuguuuacgacgugaucuaTT | 248 | uagaucacgucguaaacaaTT | 249 | 66 ± 5 |
| AD-10977 | guguuagacgguaccgaca | 250 | guguuagacgguaccgacaTT | 251 | ugucgguaccgucuaacacTT | 252 | 21 ± 2 |
| AD-10978 | cuugaacuacaucgaucau | 253 | cuugaacuacaucgaucauTT | 254 | augaucgauguaguucaagTT | 255 | 37 ± 6 |
| AD-10979 | ggccgaaacuugcuuugca | 256 | ggccgaaacuugcuuugcaTT | 257 | ugcaagcaaguuuccggccTT | 258 | 32 ± 3 |
| AD-10980 | cugucucgacagauagcug | 259 | cugucucgacagauagcugTT | 260 | cagcuaucugucgagacagTT | 261 | 26 ± 8 |
| AD-10981 | gcaucgcuauggaacuuuu | 262 | gcaucgcuauggaacuuuuTT | 263 | aaaaguuccauagcgaugcTT | 264 | 11 ± 2 |
| AD-10982 | acugacguuacaucauaca | 265 | acugacguuacaucauacaTT | 266 | uguaugauguaacgucaguTT | 267 | 13 ± 4 |
| AD-10983 | cugacguuacaucauacac | 268 | cugacguuacaucauacacTT | 269 | guguaugauguaacgucagTT | 270 | 31 ± 5 |

TABLE 1-continued

Sequences and activities of dsRNAs tested for HD gene expression inhibiting activity

| Duplex name | sequence of total 19mer target site | SEQ ID NO: | Sense strand sequence (5'-3') | SEQ ID NO: | Antisense strand sequence (5'-3') | SEQ ID NO: | Remaining HD gene mRNA [% of control] |
|---|---|---|---|---|---|---|---|
| AD-10984 | ugaaucgagaucggauguc | 271 | ugaaucgagaucggaugucTT | 272 | gacauccgaucucgauucaTT | 273 | 62 ± 13 |
| AD-10985 | uagacgguaccgacaacca | 274 | ucgacgguaccgacaaccaTT | 275 | ugguugucgguaccgucuaTT | 276 | 30 ± 4 |
| AD-10986 | uugccgcaucaaaggugac | 277 | uugccgcaucaaaggugacTT | 278 | gucaccuuugaugcggcaaTT | 279 | 68 ± 6 |
| AD-10987 | aacuacaucgaucauggag | 280 | aacuacaucgaucauggagTT | 281 | cuccaugaucgauguaguuTT | 282 | 61 ± 5 |
| AD-10988 | uuuggcggauugcauuccu | 283 | uuuggcggauugcauuccuTT | 284 | aggaaugcaauccgccaaaTT | 285 | 48 ± 5 |
| AD-10989 | gcuuuagucgagaaccaau | 286 | gcuuuagucgagaaccaauTT | 287 | auugguucucgacuaaagcTT | 288 | 29 ± 3 |
| AD-10990 | uuuagucgagaaccaauga | 289 | uuuagucgagaaccaaugaTT | 290 | ucauugguucucgacuaaaTT | 291 | 29 ± 1 |
| AD-10991 | uagucgagaaccaaugaug | 292 | uagucgagaaccaaugaugTT | 293 | caucauugguucucgacuaTT | 294 | 36 ± 3 |
| AD-10992 | aagugucuacccaguugaa | 295 | aagugucuacccaguugaaTT | 296 | uucaacggguagacacuuTT | 297 | 31 ± 3 |
| AD-10993 | ucaguuacggguuaauuac | 298 | ucaguuacgggguuaauuacTT | 299 | guaauuaacccguaacugaTT | 300 | 44 ± 8 |
| AD-10994 | uuacgggguuaauuacuguc | 301 | uuacgggguuaauuacugucTT | 302 | gacaguaauuaacccguaaTT | 303 | 88 ± 17 |
| AD-10995 | uacgggguuaauuacugucu | 304 | uacgggguuaauuacugucuTT | 305 | agacaguaauuaacccguaTT | 306 | 65 ± 5 |
| AD-10996 | gucucgacagauagcgac | 307 | gucucgacagauagcugacTT | 308 | gucagcuaucugucgagacTT | 309 | 32 ± 3 |
| AD-10997 | ucucgacagauagcugaca | 310 | ucucgacagauagcugacaTT | 311 | ugucagcuaucugucgagaTT | 312 | 34 ± 2 |
| AD-10998 | ugcgggcucguuccaugau | 313 | ugcgggcucguuccaugauTT | 314 | aucauggaacgagcccgcaTT | 315 | 34 ± 4 |
| AD-10999 | uucagucucguugugaaaa | 316 | uucagucucguugugaaaaTT | 317 | uuuucacaacgagacugaaTT | 318 | 37 ± 2 |
| AD-11000 | ugucgccgggguagaaaugc | 319 | ugucgccgggguagaaaugcTT | 320 | gcauuucuacccggcgacaTT | 321 | 91 ± 2 |
| AD-11001 | ucggaguucaaccuaagcc | 322 | ucggaguucaaccuaagccTT | 323 | ggcuuagguugaacuccgaTT | 324 | 70 ± 6 |
| AD-11002 | caugcuuaagccuagggau | 325 | caugcuuaagccuagggauTT | 326 | aucccuaggcuuaagcaugTT | 327 | 37 ± 6 |
| AD-11003 | ccgcugagucuggaucucc | 328 | ccgcugagucuggaucuccTT | 329 | ggagauccagacucagcggTT | 330 | 70 ± 12 |
| AD-11004 | ugucaacagcuacacacgu | 331 | ugucaacagcuacacacguTT | 332 | acguguguagcuguugacaTT | 333 | 43 ± 4 |
| AD-11005 | guggccggcaacccagcug | 334 | guggccggcaacccagcugTT | 335 | cagcuggguugccggccacTT | 336 | 40 ± 3 |
| AD-11006 | gaaagggaucgcccacugc | 337 | gaaagggaucgcccacugcTT | 338 | gcagugggcgaucccuuucTT | 339 | 42 ± 2 |
| AD-11007 | aaagggaucgcccacugcg | 340 | aaagggaucgcccacugcgTT | 341 | cgcagugggcgaucccuuuTT | 342 | 43 ± 2 |
| AD-11008 | cggguagaacuucagaccc | 343 | cggguagaacuucagacccTT | 344 | gggucugaaguucuacccgTT | 345 | 33 ± 3 |
| AD-11009 | gcucgaccgcagggccuuc | 346 | gcucgaccgcagggccuucTT | 347 | gaaggccugcggucgagcTT | 348 | 49 ± 4 |
| AD-11010 | agcccauaucaccggcugc | 349 | agcccauaucaccggcugcTT | 350 | gcagccggugauaugggcuTT | 351 | 46 ± 1 |
| AD-11011 | uucuaugcccguguaaagu | 352 | uucuaugcccguguaaaguTT | 353 | acuuuacacgggcauaaaaTT | 354 | 100 ± 5 |
| AD-11012 | cccuuuuagucaggagagu | 355 | cccuuuuagucaggagaguTT | 356 | acucuccugacuaaaagggTT | 357 | 94 ± 8 |
| AD-11013 | gguuggcgacugucaugug | 358 | gguuggcgacugucauguguTT | 359 | cacaugacagucgccaaccTT | 360 | 156 ± 10 |
| AD-11014 | acugucucgacagauagcu | 361 | acugucucgacagauagcuTT | 362 | agcuaucugucgagacaguTT | 363 | 39 ± 5 |
| AD-11015 | uugucugacaauauguguaa | 364 | uugucugacaauaugugaaTT | 365 | uucacauauugucagacaaTT | 366 | 21 ± 1 |
| AD-11016 | cugggcaucgcuauggaac | 367 | cugggcaucgcuauggaacTT | 368 | guuccauagcgaugcccagTT | 369 | 25 ± 3 |
| AD-11017 | cucggaguuugcgugcugc | 370 | cucggaguuugcgugcugcTT | 371 | gcagcacgcaaacuccgagTT | 372 | 29 ± 3 |
| AD-11018 | uguuaaaggccuucauagc | 373 | uguuaaaggccuucauagcTT | 374 | gcuaugaaggccuuuaacaTT | 375 | 42 ± 3 |
| AD-11019 | uuaaaggccuucauagcga | 376 | uuaaaggccuucauagcgaTT | 377 | ucgcuaugaaggccuuuaaTT | 378 | 32 ± 4 |
| AD-11020 | gccuucauagcgaaccuga | 379 | gccuucauagcgaaccugaTT | 380 | ucagguucgcuaugaaggcTT | 381 | 26 ± 10 |

TABLE 1-continued

Sequences and activities of dsRNAs tested for HD gene expression inhibiting activity

| Duplex name | sequence of total 19mer target site | SEQ ID NO: | Sense strand sequence (5'-3') | SEQ ID NO: | Antisense strand sequence (5'-3') | SEQ ID NO: | Remaining HD gene mRNA [% of control] |
|---|---|---|---|---|---|---|---|
| AD-11021 | aaggcagcuucggagugac | 382 | aaggcagcuucggagugacTT | 383 | gucacuccgaagcugccuuTT | 384 | 27 ± 2 |
| AD-11022 | agguuuaugaacugacguu | 385 | agguuuaugaacugacguuTT | 386 | aacgucaguucauaaaccuTT | 387 | 10 ± 2 |
| AD-11023 | aacugacguuacaucauac | 388 | aacugacguuacaucauacTT | 389 | guaugauguaacgucaguuTT | 390 | 39 ± 3 |
| AD-11024 | cacaauguugugaccggag | 391 | cacaauguugugaccggagTT | 392 | cuccggucacaacauugugTT | 393 | 23 ± 4 |
| AD-11025 | caauguugugaccggagcc | 394 | caauguugugaccggagccTT | 395 | ggcuccggucacaacauugTT | 396 | 25 ± 4 |
| AD-11026 | agcagcucuucagaacgcc | 397 | agcagcucuucagaacgccTT | 398 | ggcguucugaagagcugcuTT | 399 | 74 ± 11 |
| AD-11027 | guggccgaagccguagugg | 400 | guggccgaagccguaguggTT | 401 | ccacuacggcuucggccacTT | 402 | 32 ± 4 |
| AD-11028 | cguagugggaguauugugg | 403 | cguagugggaguauuguggTT | 404 | ccacaauacucccacuacgTT | 405 | 26 ± 4 |
| AD-11029 | ggaguauuguggaacuuau | 406 | ggaguauuguggaacuuauTT | 407 | auaaguuccacaauacuccTT | 408 | 20 ± 2 |
| AD-11030 | aguauuguggaacuuauag | 409 | aguauuguggaacuuauagTT | 410 | cuauaaguuccacaauacuTT | 411 | 35 ± 3 |
| AD-11031 | gagaucggaugucagcagc | 412 | gagaucggaugucagcagcTT | 413 | gcugcugacauccgaucucTT | 414 | 53 ± 18 |
| AD-11032 | cagcgccgucccaucugac | 415 | cagcgccgucccaucugacTT | 416 | gucagaugggacggcgcugTT | 417 | 49 ± 4 |
| AD-11033 | ccaccgaagggccugauuc | 418 | ccaccgaagggccugauucTT | 419 | gaaucaggcccuucgguggTT | 420 | 28 ± 6 |
| AD-11034 | auuguguuagacgguaccg | 421 | auuguguuagacgguaccgTT | 422 | cgguaccgcuaacacaauTT | 423 | 111 ± 12 |
| AD-11035 | ccgacaaccaguauuuggg | 424 | ccgacaaccaguauuugggTT | 425 | cccaaauacugguugucggTT | 426 | 25 ± 5 |
| AD-11036 | aaacaagccuugccgcauc | 427 | aaacaagccuugccgcaucTT | 428 | gaugcggcaaggcuuguuuTT | 429 | 35 ± 4 |
| AD-11037 | gccuugccgcaucaaaggu | 430 | gccuugccgcaucaaagguTT | 431 | accuuugaugcggcaaggcTT | 432 | 36 ± 9 |
| AD-11038 | aucuugaacuacaucgauc | 433 | aucuugaacuacaucgaucTT | 434 | gaucgauguaguucaagauTT | 435 | 40 ± 5 |
| AD-11039 | aucgaucauggagacccac | 436 | aucgaucauggagacccacTT | 437 | gugggucuccaugaucgauTT | 438 | 69 ± 5 |
| AD-11040 | uggagacccacagguucga | 439 | uggagacccacagguucgaTT | 440 | ucgaaccugugggucuccaTT | 441 | 39 ± 9 |
| AD-11041 | ggagacccacagguucgag | 442 | ggagacccacagguucgagTT | 443 | cucgaaccugugggucuccTT | 444 | 65 ± 14 |
| AD-11042 | ccgcuuccacgugggagau | 445 | ccgcuuccacgugggagauTT | 446 | aucucccacgugggaagcggTT | 447 | 63 ± 2 |
| AD-11043 | ucuuuggcggauugcauuc | 448 | ucuuuggcggauugcauucTT | 449 | gaaugcaauccgccaaagaTT | 450 | 60 ± 5 |
| AD-11044 | uuggcggauugcauuccuu | 451 | uuggcggauugcauuccuuTT | 452 | aaggaaugcaauccgccaaTT | 453 | 30 ± 2 |
| AD-11045 | agcagcuacagugaguuag | 454 | agcagcuacagugaguuagTT | 455 | cuaacucacuguagcugcuTT | 456 | 64 ± 2 |
| AD-11046 | cgagugcucaauaauguug | 457 | cgagugcucaauaauguugTT | 458 | caacauuauugagcacucgTT | 459 | 18 ± 5 |
| AD-11047 | aauuaggcuugucccaaag | 460 | aauuaggcuugucccaaagTT | 461 | cuuugggacaagccuaauuTT | 462 | 54 ± 14 |
| AD-11048 | uggaguuuagguuggcacu | 463 | uggaguuuagguuggcacuTT | 464 | agugccaaccuaaacuccaTT | 465 | 44 ± 5 |
| AD-11049 | cuugguucccauuggaucu | 466 | cuugguucccauuggaucuTT | 467 | agauccaaugggaaccaagTT | 468 | 32 ± 4 |
| AD-11050 | uuuuggccggaaacuugcu | 469 | uuuuggccggaaacuugcuTT | 470 | agcaaguuuccggccaaaaTT | 471 | 53 ± 12 |
| AD-11051 | ugccuucucuaacaaaccc | 472 | ugccuucucuaacaaacccTT | 473 | ggguuuguuagagaaggcaTT | 474 | 57 ± 5 |
| AD-11052 | uaagucccauccgacgaaa | 475 | uaagucccauccgacgaaaTT | 476 | uuucgucggaugggacuuaTT | 477 | 43 ± 4 |
| AD-11053 | ugauaccucagguccuguu | 478 | ugauaccucagguccuguuTT | 479 | aacaggaccugagguaucaTT | 480 | 26 ± 2 |
| AD-11054 | gauaccucagguccuguua | 481 | gauaccucagguccuguuaTT | 482 | uaacaggaccugagguaucTT | 483 | 30 ± 5 |
| AD-11055 | uguuacaacaaguaaaucc | 484 | uguuacaacaaguacauccTT | 485 | ggauuuacuuguuguaacaTT | 486 | 81 ± 4 |
| AD-11056 | cuaggauaccugaaauccu | 487 | cuaggauaccugaaauccuTT | 488 | aggauuucagguauccuagTT | 489 | 35 ± 13 |
| AD-11057 | cuuuagucgagaaccaaug | 490 | cuuuagucgagaaccaaugTT | 491 | cauugguucucgacuaaagTT | 492 | 33 ± 6 |

TABLE 1-continued

Sequences and activities of dsRNAs tested for HD gene expression inhibiting activity

| Duplex name | sequence of total 19mer target site | SEQ ID NO: | Sense strand sequence (5'-3') | SEQ ID NO: | Antisense strand sequence (5'-3') | SEQ ID NO: | Remaining HD gene mRNA [% of control] |
|---|---|---|---|---|---|---|---|
| AD-11058 | acuguuuguguucaacaau | 493 | acuguuuguguucaacaauTT | 494 | auuguugaacacaaacaguTT | 495 | 39 ± 4 |
| AD-11059 | caauuguugaagacucucu | 496 | caauuguugaagacucucuTT | 497 | agagagucuucaacaauugTT | 498 | 39 ± 3 |
| AD-11060 | caagucacaaggccgagca | 499 | caagucacaaggccgagcaTT | 500 | ugcucggccuugugacuugTT | 501 | 40 ± 1 |
| AD-11061 | aagucacaaggccgagcac | 502 | aagucacaaggccgagcacTT | 503 | gugcucggccuugugacuuTT | 504 | 38 ± 5 |
| AD-11062 | ggcuuguaccacuacugcu | 505 | ggcuuguaccacuacugcuTT | 506 | agcaguagugguacaagccTT | 507 | 27 ± 3 |
| AD-11063 | acgacaccucgggaugguu | 508 | acgacaccucgggaugguuTT | 509 | aaccaucccgaggugucguTT | 510 | 38 ± 4 |
| AD-11064 | caccucgggauggutugau | 511 | caccucgggaugguuugauTT | 512 | aucaaaccaucccgaggugTT | 513 | 52 ± 11 |
| AD-11065 | cucgggaugguuugauguc | 514 | cucgggaugguuugaugucTT | 515 | gacaucaaaccaucccgagTT | 516 | 49 ± 13 |
| AD-11066 | agugucacaaagaaccgug | 517 | agugucacaaagaaccgugTT | 518 | cacgguucuuugugacacuTT | 519 | 43 ± 13 |
| AD-11067 | gugucacaaagaaccgugc | 520 | gugucacaaagaaccgugcTT | 521 | gcacgguucuuugugacacTT | 522 | 30 ± 6 |
| AD-11068 | aaccgugcagauaagaaug | 523 | aaccgugcagauaagaaugTT | 524 | cauucuuaucugcacgguuTT | 525 | 36 ± 7 |
| AD-11069 | accgugcagauaagaaugc | 526 | accgugcagauaagaaugcTT | 527 | gcauucuuaucugcacgguTT | 528 | 39 ± 3 |
| AD-11070 | ccgugcagauaagaaugcu | 529 | ccgugcagauaagaaugcuTT | 530 | agcauucuuaucugcacggTT | 531 | 39 ± 3 |
| AD-11071 | gcagauaagaaugcuauuc | 532 | gcagauaagaaugcuauucTT | 533 | gaauagcauucuuaucugcTT | 534 | 37 ± 4 |
| AD-11072 | acauucguuuguuugaacc | 535 | acauucguuuguuugaaccTT | 536 | gguucaaacaaacgaauguTT | 537 | 62 ± 3 |
| AD-11073 | ugaaccucuuguuauaaaa | 538 | ugaaccucuuguuauaaaaTT | 539 | uuuuauaacaagagguucaTT | 540 | 21 ± 4 |
| AD-11074 | uuuagauuugcuggcgcag | 541 | uuuagauuugcuggcgcagTT | 542 | cugcgccagcaaaucuaaaTT | 543 | 80 ± 5 |
| AD-11075 | ugguucaguuacggguuaa | 544 | ugguucaguuacggguuaaTT | 545 | uuaacccguaacugaaccaTT | 546 | 32 ± 13 |
| AD-11076 | gggccaguucagggaauca | 547 | gggccaguucagggaaucaTT | 548 | ugauucccugaacuggcccTT | 549 | 30 ± 7 |
| AD-11077 | uggaagcgacugucucgac | 550 | uggaagcgacugucucgacTT | 551 | gucgagacagucgcuuccaTT | 552 | 41 ± 5 |
| AD-11078 | ggaagcgacugucucgaca | 553 | ggaagcgacugucucgacaTT | 554 | ugucgagacagucgcuuccTT | 555 | 30 ± 8 |
| AD-11079 | gaagcgacugucucgacag | 556 | gaagcgacugucucgacagTT | 557 | cugucgagacagucgcuucTT | 558 | 35 ± 8 |
| AD-11080 | gcgacugucucgacagaua | 559 | gcgacugucucgacagauaTT | 560 | uaucugucgagacagucgcTT | 561 | 35 ± 6 |
| AD-11081 | ugucucgacagauagcuga | 562 | ugucucgacagauagcugaTT | 563 | ucagcuaucugucgagacaTT | 564 | 33 ± 4 |
| AD-11082 | cucgacagauagcugacau | 565 | cucgacagauagcugacauTT | 566 | augucagcuaucugucgagTT | 567 | 39 ± 7 |
| AD-11083 | agguggaaaugagugagca | 568 | agguggaaaugagugagcaTT | 569 | ugcucacucauuuccaccuTT | 570 | 27 ± 4 |
| AD-11084 | agugagcagcaacauacuu | 571 | agugagcagcaacauacuuTT | 572 | aaguauguugcugcucacuTT | 573 | 23 ± 3 |
| AD-11085 | guuccgcagugauggcugu | 574 | guuccgcagugauggcuguTT | 575 | acagccaucacugcggaacTT | 576 | 37 ± 4 |
| AD-11086 | caaccacaccgacuaccgc | 577 | caaccacaccgacuaccgcTT | 578 | gcgguagucggugugguugTT | 579 | 36 ± 5 |
| AD-11087 | aaccacaccgacuaccgcu | 580 | anccacaccgacuaccgcuTT | 581 | agcgguagucggugugguuTT | 582 | 48 ± 10 |
| AD-11088 | accacaccgacuaccgcug | 583 | accacaccgacuaccgcugTT | 584 | cagcgguagucggugugguTT | 585 | 42 ± 3 |
| AD-11089 | cccgaaaagacacagucug | 586 | cccgaaaagacacagucugTT | 587 | cagacugugucuuuucgggTT | 588 | 37 ± 2 |
| AD-11090 | uccagcacaaaguuacuua | 589 | uccagcacaaaguuacuuaTT | 590 | uaaguaacuuugugcuggaTT | 591 | 35 ± 4 |
| AD-11091 | uuggaaugugcaauagaga | 592 | uuggaaugugcaauagagaTT | 593 | ucucuauugcacauuccaaTT | 594 | 29 ± 6 |
| AD-11092 | agaucugaucagccuuucc | 595 | agaucugaucagccuuuccTT | 596 | ggaaaggcugaucagaucuTT | 597 | 43 ± 3 |
| AD-11093 | caggcaauucagucucguu | 598 | caggcaauucagucucguuTT | 599 | aacgagacugaauugccugTT | 600 | 31 ± 3 |
| AD-11094 | ggcaauucagucucguugu | 601 | ggcaauucagucucguuguTT | 602 | acaacgagacugaauugccTT | 603 | 27 ± 3 |

TABLE 1-continued

Sequences and activities of dsRNAs tested for HD gene expression inhibiting activity

| Duplex name | sequence of total 19mer target site | SEQ ID NO: | Sense strand sequence (5'-3') | SEQ ID NO: | Antisense strand sequence (5'-3') | SEQ ID NO: | Remaining HD gene mRNA [% of control] |
|---|---|---|---|---|---|---|---|
| AD-11095 | gcaauucagucucguugug | 604 | gcaauucagucucguugugTT | 605 | cacaacgagacugaauugcTT | 606 | 23 ± 3 |
| AD-11096 | aauucagucucguugugaa | 607 | aauucagucucguugugaaTT | 608 | uucacaacgagacugaauuTT | 609 | 27 ± 3 |
| AD-11097 | ucagucucguugugaaaac | 610 | ucagucucguugugaaaacTT | 611 | guuuucacaacgagacugaTT | 612 | 42 ± 8 |
| AD-11098 | aaaccuuucaacuccaacc | 613 | aaaccuuucaacuccaaccTT | 614 | gguuggaguugaaagguuuTT | 615 | 60 ± 7 |
| AD-11099 | cuuuccgugugcuggcucg | 616 | cuuuccgugugcuggcucgTT | 617 | cgagccagcacacggaaagTT | 618 | 46 ± 4 |
| AD-11100 | ccgugugcuggcucgcaug | 619 | ccgugugcuggcucgcaugTT | 620 | caugcgagccagcacacggTT | 621 | 33 ± 3 |
| AD-11101 | ucgacauccuugcuugucg | 622 | ucgacauccuugcuugucgTT | 623 | cgacaagcaaggaugucgaTT | 624 | 47 ± 4 |
| AD-11102 | ugcuugucgccggguagaa | 625 | ugcuugucgccggguagaaTT | 626 | uucuacccggcgacaagcaTT | 627 | 43 ± 8 |
| AD-11103 | gcuugucgccggguagaaa | 628 | gcuugucgccggguagaaaTT | 629 | uuucuacccggcgacaagcTT | 630 | 35 ± 7 |
| AD-11104 | cuugucgccggguagaaau | 631 | cuugucgccggguagaaauTT | 632 | auuucuacccggcgacaagTT | 633 | 37 ± 9 |
| AD-11105 | ggcccaguugccaauggaa | 634 | ggcccaguugccaauggaaTT | 635 | uuccauuggcaacugggccTT | 636 | 39 ± 5 |
| AD-11106 | cagguuucgucucuccacc | 637 | cagguuucgucucuccaccTT | 638 | gguggagagacgaaaccugTT | 639 | 38 ± 8 |
| AD-11107 | ggcacgugucacuggaaac | 640 | ggcacgugucacuggaaacTT | 641 | guuuccagugacacgugccTT | 642 | 39 ± 3 |
| AD-11108 | cuggaaacagugaguccgg | 643 | cuggaaacagugaguccggTT | 644 | ccggacucacuguuuccagTT | 645 | 51 ± 3 |
| AD-11109 | caaaucccaguguuggacc | 646 | caaaucccaguguuggaccTT | 647 | gguccaacacugggauuugTT | 648 | 53 ± 4 |
| AD-11110 | acucggaguucaaccuaag | 649 | acucggaguucaaccuaagTT | 650 | cuuagguugaacuccgaguTT | 651 | 43 ± 3 |
| AD-11111 | cucggaguucaaccuaagc | 652 | cucggaguucaaccuaagcTT | 653 | gcuuagguugaacuccgagTT | 654 | 41 ± 6 |
| AD-11112 | agccuagggaugagugaaa | 655 | agccuagggaugagugaaaTT | 656 | uuucacucaucccuaggcuTT | 657 | 34 ± 5 |
| AD-11113 | gucaacagcuacacacgug | 658 | gucaacagcuacacacgugTT | 659 | cacguguagcuguugacTT | 660 | 42 ± 4 |
| AD-11114 | gauggucacccaaaccggg | 661 | gauggucacccaaaccgggTT | 662 | cccgguuugggugaccaucTT | 663 | 49 ± 3 |
| AD-11115 | ugacagaacugcgaagggu | 664 | ugacagnacugcgaaggguTT | 665 | acccuucgcaguucugucaTT | 666 | 53 ± 8 |
| AD-11116 | gaagacgagauccucgcuc | 667 | gaagacgagauccucgcucTT | 668 | gagcgaggaucucgucuucTT | 669 | 43 ± 7 |
| AD-11117 | acgagauccucgcucagua | 670 | acgagauccucgcucaguaTT | 671 | uacugagcgaggaucucguTT | 672 | 40 ± 9 |
| AD-11118 | aaccugaaagggaucgccc | 673 | aaccugaaagggaucgcccTT | 674 | gggcgaucccuuucagguuTT | 675 | 81 ± 7 |
| AD-11119 | gaucgcccacugcgugaac | 676 | gaucgcccacugcgugaacTT | 677 | guucacgcagugggcgaucTT | 678 | 50 ± 7 |
| AD-11120 | cacugcgugaacauucaca | 679 | cacugcgugaacauucacaTT | 680 | ugugaauguucacgcagugTT | 681 | 40 ± 13 |
| AD-11121 | agaacuauccucuggacgu | 682 | agaacuauccucuggacguTT | 683 | acguccagaggauaguucuTT | 684 | 41 ± 8 |
| AD-11122 | gucaguccggguagaacuu | 685 | gucaguccggguagaacuuTT | 686 | aaguucuacccggacugaTT | 687 | 37 ± 10 |
| AD-11123 | ugaacaaagucaucggaga | 688 | ugaacaaagucaucggagaTT | 689 | ucuccgaugacuuuguucaTT | 690 | 39 ± 6 |
| AD-11124 | aagucaucggagaguuucu | 691 | aagucaucggagaguuucuTT | 692 | agaaacucuccgaugacuuTT | 693 | 40 ± 2 |
| AD-11125 | gucaucggagaguuucugu | 694 | gucaucggagaguuucuguTT | 695 | acagaaacucuccgaugacTT | 696 | 37 ± 4 |
| AD-11126 | ggccaccguguguauaag | 697 | ggccaccguguguauaagTT | 698 | cuuauacaccacgguggccTT | 699 | 48 ± 2 |
| AD-11127 | accgguguguauaaggugu | 700 | accgguguguauaagguguTT | 701 | acaccuuauacaccacgguTT | 702 | 36 ± 2 |
| AD-11128 | cugacuuguuuacgaaaug | 703 | cugacuuguuuacgaaaugTT | 704 | cauuucgaaacaagucaTT | 705 | 33 ± 7 |
| AD-11129 | uguuuacgaaauguccaca | 706 | uguuuacgaaauguccacaTT | 707 | uguggacauuucguaaacaTT | 708 | 46 ± 8 |
| AD-11130 | ccaccgagccagcuugguc | 709 | ccaccgagccagcuuggucTT | 710 | gaccaagcuggcucgguguTT | 711 | 51 ± 12 |
| AD-11131 | caccgagccagcuuggucc | 712 | caccgagccagcuugguccTT | 713 | ggaccaagcuggcucgguguTT | 714 | 53 ± 15 |

TABLE 1-continued

Sequences and activities of dsRNAs tested for HD gene expression inhibiting activity

| Duplex name | sequence of total 19mer target site | SEQ ID NO: | Sense strand sequence (5'-3') | SEQ ID NO: | Antisense strand sequence (5'-3') | SEQ ID NO: | Remaining HD gene mRNA [% of control] |
|---|---|---|---|---|---|---|---|
| AD-11132 | caggcaacgugcgugucuc | 715 | caggcaacgugcgugucucTT | 716 | gagacacgcacguugccugTT | 717 | 46 ± 6 |
| AD-11133 | aacgugcgugucucugcca | 718 | aacgugcgugucucugccaTT | 719 | uggcagagacacgcacguuTT | 720 | 59 ± 6 |
| AD-11134 | uuaauuuuaacguaacucu | 721 | uuaauuuuaacguaacucuTT | 722 | agaguuacguuaaaauuaaTT | 723 | 64 ± 16 |
| AD-11135 | uuaacguaacucuuucuau | 724 | uuaacguaacucuuucuauTT | 725 | auagaaagaguuacguuaaTT | 726 | 57 ± 6 |
| AD-11136 | uaacguaacucuuucuaug | 727 | uaacguaacucuuucuaugTT | 728 | cauagaaagaguuacguuaTT | 729 | 72 ± 9 |
| AD-11137 | aacguaacucuuucuaugc | 730 | aacguaacucuuucuaugcTT | 731 | gcauagaaagaguuacguuTT | 732 | 68 ± 8 |
| AD-11138 | guaacucuuucuaugcccg | 733 | guaacucuuucuaugcccgTT | 734 | cgggcauagaaagaguuacTT | 735 | 69 ± 10 |
| AD-11139 | uaugcccguguaaaguaug | 736 | uaugcccguguaaaguaugTT | 737 | cauacuuuacacgggcauaTT | 738 | 102 ± 4 |
| AD-11140 | ugcccguguaaaguaugug | 739 | ugcccguguaaaguaugugTT | 740 | cacauacuuuacacgggcaTT | 741 | 104 ± 9 |
| AD-11141 | ugagcacccgcugacauuu | 742 | ugagcacccgcugacauuuTT | 743 | aaaugucagcgggugcucaTT | 744 | 110 ± 25 |
| AD-11142 | cacccgcugacauuuccgu | 745 | cacccgcugacauuuccguTT | 746 | acggaaaugucagcgggugTT | 747 | 50 ± 4 |
| AD-11143 | uuuuagucaggagagugca | 748 | uuuuagucaggagagugcaTT | 749 | ugcacucuccugacuaaaaTT | 750 | 93 ± 17 |
| AD-11144 | agccaagucauuaaaaugg | 751 | agccaagucauuaaaauggTT | 752 | ccauuuuaaugacuuggcuTT | 753 | 62 ± 4 |
| AD-11145 | guuggcgacugucauggg | 754 | guuggcgacugucaugggTT | 755 | ccacaugacagucgccaacTT | 756 | 57 ± 4 |
| AD-11146 | gcccuuaagggaagcuacu | 757 | gcccuuaagggaagcuacuTT | 758 | aguagcuucccuuagggcTT | 759 | 74 ± 5 |
| AD-11147 | gcauaucgcugggcucaac | 760 | gcauaucgcugggcucaacTT | 761 | guugagcccagcgauaugcTT | 762 | 61 ± 10 |
| AD-11148 | aauaugagcucauuaguaa | 763 | aaucugagcucauuaguaaTT | 764 | uuacuaaugagcucauauuTT | 765 | 61 ± 8 |
| AD-11149 | gugcccgugucgguucuuc | 766 | gugcccgugucgguucuucTT | 767 | gaagaaccgacacgggcacTT | 768 | 66 ± 5 |
| AD-11150 | aaugaaaccagggguagaau | 769 | aaugaaaccagggguagaauTT | 770 | auucuacccugguuucauuTT | 771 | 101 ± 7 |
| AD-11151 | cacccagaauguagcaucu | 772 | cacccagaauguagcaucuTT | 773 | agaugcuacauucggggugTT | 774 | 98 ± 8 |
| AD-11152 | gagcucgggacggauagua | 775 | gagcucgggacggauaguaTT | 776 | uacuauccgucccgagcucTT | 777 | 77 ± 2 |
| AD-11153 | ugacaacugaaggcaaccu | 778 | ugacaacugaaggcaaccuTT | 779 | agguugccuucaguugucaTT | 780 | 86 ± 3 |
| AD-11154 | caacguggaccugccuacg | 781 | caacguggaccugccuacgTT | 782 | cguaggcaggccacguugTT | 783 | 86 ± 4 |
| AD-11155 | gacugacgagagauguaua | 784 | gacugacgagagauguauaTT | 785 | uauacaucucucgucagucTT | 786 | 72 ± 2 |
| AD-11156 | acgagagauguauauuuaa | 787 | acgagagauguauauuuaaTT | 788 | uuaaauauacaucucucguTT | 769 | 63 ± 3 |

TABLE 2

Sequences and activities of dsRNAs with stabilizing modifications tested for HD gene expression inhibiting activity

| Duplex name | Sense strand sequence (5'-3') | SEQ ID NO: | Antisense strand sequence (5'-3') | SEQ ID NO: | Remaining HD gene mRNA (% of controls) |
|---|---|---|---|---|---|
| AL-DP-5996 | cmumumumagumcmgagaacmcmaaumgTT | 790 | cmauugguucucgacumaaagTT | 791 | 24 ± 7 |
| AL-DP-5997 | gumcmacmaaagaacmcmgumgcmagTT | 792 | cugcmacgguucuuugugacTT | 793 | 21 ± 5 |
| AL-DP-5998 | umcmggagumcmaacmcmumaagcmcmTT | 794 | ggcuumagguugaacuccgaTT | 795 | 36 ± 9 |
| AL-DP-5999 | gaaaumcmcmumgcmumumumagumcmgaTT | 796 | ucgacumaaagcmaggauuucTT | 797 | 20 ± 4 |
| AL-DP-6000 | umcmcmumgcmumumumagumcmgagaacmTT | 798 | guucucgacumaaagcmaggaTT | 799 | 22 ± 3 |
| AL-DP-6001 | umumagumcmgagaacmcmaaumgaumTT | 800 | aucmauugguucucgacumaaTT | 801 | 23 ± 7 |

TABLE 2-continued

Sequences and activities of dsRNAs with stabilizing modifications tested for HD gene expression inhibiting activity

| Duplex name | Sense strand sequence (5'-3') | SEQ ID NO: | Antisense strand sequence (5'-3') | SEQ ID NO: | Remaining HD gene mRNA (% of controls) |
|---|---|---|---|---|---|
| AL-DP-6002 | umagumcmgagaacmcmaaumgaumgTT | 802 | cmaucmauuggumucucgacumaTT | 803 | 20 ± 7 |
| AL-DP-6003 | cmumgcmumumumagumcmgagaacmcmaTT | 804 | ugguucucgacumaaaagcmagTT | 805 | 26 ± 4 |
| AL-DP-6004 | cmgcmumgcmacmcmgacmcmaaagaaTT | 806 | uucuuggucggugcmagcgTT | 807 | 42 ± 7 |
| AL-DP-6005 | umgcmumumumagumcmgagaacmcmaaTT | 808 | uugguucucgacumaaaagcmaTT | 809 | 21 ± 8 |
| AL-DP-6006 | gaacmumacmaumcmgaumcmaumggaTT | 810 | uccmaugaucgaugumaguucTT | 811 | 21 ± 6 |
| AL-DP-6007 | umgaacmumacmaumcmgaumcmaumggTT | 812 | ccmaugaucgaugumaguucmaTT | 813 | 21 ± 3 |
| AL-DP-6008 | cmaaagaacmcmgumgcmagaumaaaTT | 814 | uumaucugcmacgguucuuugTT | 815 | 21 ± 8 |
| AL-DP-6009 | cmcmcmacmumgcmgumgaacmaumumcmaTT | 816 | ugaauguucmacgcmagugggTT | 817 | 22 ± 4 |
| AL-DP-6010 | umumumagumcmgagaacmcmaaumgaTT | 818 | ucmauuggumucucgacumaaaTT | 819 | 31 ± 5 |
| AL-DP-6011 | umggaaumgumumcmcmggagaaumcmTT | 820 | gauucccggaacmauuccmaTT | 821 | 26 ± 4 |
| AL-DP-6012 | cmggagumumcmaacmcmumaagcmcmumTT | 822 | aggcuumagguugaacuccgTT | 823 | 28 ± 6 |
| AL-DP-6013 | umggcmaumumumgaumcmcmaumgagcmTT | 824 | gcucmauggaucmaaaugccmaTT | 825 | 34 ± 11 |
| AL-DP-6014 | umcmumggaaumgumumcmcmggagaaTT | 826 | uucuccggaacmauuccmagaTT | 827 | 23 ± 7 |
| AL-DP-6015 | ggcmumgcmaaaumumumacmagagcmTT | 828 | gcucugumaaauuugcmagccTT | 829 | 29 ± 5 |
| AL-DP-6016 | gcmgumgaacmaumumcmacmagcmcmaTT | 830 | uggcugugaauguucmacgcTT | 831 | 17 ± 5 |
| AL-DP-6017 | umcmcmaggumumumaumgaacmumgacmTT | 832 | gucmaguucmaumaaaaccuggaTT | 833 | 19 ± 5 |
| AL-DP-6018 | aggcmaaagumgcmumcmumumaggaTT | 834 | uccumaagagcmacuuugccuTT | 835 | 22 ± 6 |
| AL-DP-6019 | aacmumacmaumcmgaumcmaumggagTT | 836 | cuccmaugaucgaugumaguuTT | 837 | 59 ± 10 |
| AL-DP-6020 | cmaumumggaaumumcmcmumaaaaumcmTT | 838 | gauuumaggaauuccmaaugTT | 839 | 19 ± 11 |
| AL-DP-6021 | aumcmcmumgcmumumumagumcmgagaaTT | 840 | uucucgacumaaaagcmaggauTT | 841 | 35 ± 9 |
| AL-DP-6022 | acmumacmaumcmgaumcmaumggagaTT | 842 | ucuccmaugaucgaugumaguTT | 843 | 35 ± 18 |
| AL-DP-6023 | aaumcmcmumgcmumumumagumcmgagaTT | 844 | ucucgacumaaaagcmaggauuTT | 845 | 26 ± 16 |
| AL-DP-6024 | umgumcmcmaggumumumaumgaacmumgTT | 846 | cmaguucmaumaaaaccuggacmaTT | 847 | 16 ± 5 |
| AL-DP-6025 | cmumcmggagumumcmaacmcmumaagcmTT | 848 | gcuumagguugaacuccgagTT | 849 | 24 ± 6 |
| AL-DP-6026 | umgaaaumcmcmumgcmumumumagumcmgTT | 850 | cgacumaaaagcmaggauuucmaTT | 851 | 21 ± 6 |
| AL-DP-6027 | cmagcmumumgumcmcmaggumumumaumgTT | 852 | cmaumaaaaccuggacmaagcugTT | 853 | 22 ± 6 |
| AL-DP-6028 | cmgumgaacmaumumcmacmagcmcmagTT | 854 | cuggcugugaauguucmacgTT | 855 | 33 ± 11 |
| AL-DP-6029 | cmumggcmumcmgcmaumggumcmgacmaTT | 856 | ugucgaccmaugcgagccmagTT | 857 | 45 ± 15 |
| AL-DP-6030 | agcmumumgumcmcmaggumumumaumgaTT | 858 | ucmaumaaaaccuggacmaagcuTT | 859 | 75 ± 15 |
| AL-DP-6031 | ggcmaaagumgcmumcmumumaggagTT | 860 | cuccumaagagcmacuuugccTT | 861 | 28 ± 10 |
| AL-DP-6032 | gaumcmaumumggaaumumcmcmumaaaTT | 862 | uuumaggaauuccmaaugaucTT | 863 | 25 ± 10 |
| AL-DP-6033 | cmacmumgcmgumgaacmaumumcmacmaTT | 864 | ugugaauguucmacgcmagugTT | 865 | 24 ± 3 |
| AL-DP-6034 | gumcmgagaacmcmaaumgaumggcmTT | 866 | gccmaucmauuggumucucgacTT | 867 | 20 ± 1 |
| AL-DP-6035 | cmumumgumcmcmaggumumumaumgaacmTT | 868 | guucmaumaaaaccuggacmaagTT | 869 | 28 ± 9 |
| AL-DP-6036 | umgumgaumggcmaumcmaumggcmcmaTT | 870 | uggccmaugaugcmaucmacmaTT | 871 | 50 ± 14 |
| AL-DP-6037 | cmacmaaagaacmcmgumgcmagaumTT | 872 | aucugcmacgguucuuugugTT | 873 | 20 ± 5 | dsRNA Synthesis

Source of Reagents

Where the source of a reagent is not specifically given herein, such reagent may be obtained from any supplier of reagents for molecular biology at a quality/purity standard for application in molecular biology.

siRNA Synthesis

Single-stranded RNAs were produced by solid phase synthesis on a scale of 1 μmole using an Expedite 8909 synthesizer (Applied Biosystems, Applera Deutschland GmbH, Darmstadt, Germany) and controlled pore glass (CPG, 500 Å, Proligo Biochemie GmbH, Hamburg, Germany) as solid support. RNA and RNA containing 2'-O-methyl nucleotides were generated by solid phase synthesis employing the corresponding phosphoramidites and 2'-O-methyl phosphoramidites, respectively (Proligo Biochemie GmbH, Hamburg, Germany). These building blocks were incorporated at selected sites within the sequence of the oligoribonucleotide chain using standard nucleoside phosphoramidite chemistry such as described in Current protocols in nucleic acid chemistry, Beaucage, S. L. et al. (Edrs.), John Wiley & Sons, Inc., New York, N.Y., USA. Phosphorothioate linkages were introduced by replacement of the iodine oxidizer solution with a solution of the Beaucage reagent (Chruachem Ltd, Glasgow, UK) in acetonitrile (1%). Further ancillary reagents were obtained from Mallinckrodt Baker (Griesheim, Germany).

Deprotection and purification of the crude oligoribonucleotides by anion exchange HPLC were carried out according to established procedures. Yields and concentrations were determined by UV absorption of a solution of the respective RNA at a wavelength of 260 nm using a spectral photometer (DU 640B, Beckman Coulter GmbH, Unterschleißheim, Germany). Double stranded RNA was generated by mixing an equimolar solution of complementary strands in annealing buffer (20 mM sodium phosphate, pH 6.8; 100 mM sodium chloride), heated in a water bath at 85-90° C. for 3 minutes and cooled to room temperature over a period of 3-4 hours. The annealed RNA solution was stored at −20° C. until use.

For the synthesis of 3'-cholesterol-conjugated siRNAs (herein referred to as -Chol or -sChol, depending on whether the link to the cholesteryl group is effected via a phosphodiester or a phosorothioate diester group), an appropriately modified solid support was used for RNA synthesis. The modified solid support was prepared as follows:

Diethyl-2-azabutane-1,4-dicarboxylate AA

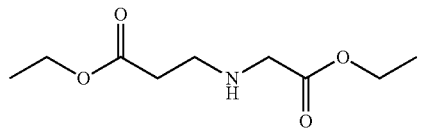

A 4.7 M aqueous solution of sodium hydroxide (50 mL) was added into a stirred, ice-cooled solution of ethyl glycinate hydrochloride (32.19 g, 0.23 mole) in water (50 mL). Then, ethyl acrylate (23.1 g, 0.23 mole) was added and the mixture was stirred at room temperature until completion of the reaction was ascertained by TLC. After 19 h the solution was partitioned with dichloromethane (3×100 mL). The organic layer was dried with anhydrous sodium sulfate, filtered and evaporated. The residue was distilled to afford AA (28.8 g, 61%).

3-{Ethoxycarbonylmethyl-[6-(9H-fluoren-9-yl-methoxycarbonyl-amino)-hexanoyl]-amino}-propionic acid ethyl ester AB

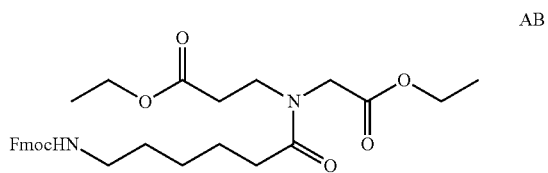

Fmoc-6-amino-hexanoic acid (9.12 g, 25.83 mmol) was dissolved in dichloromethane (50 mL) and cooled with ice. Diisopropylcarbodiimde (3.25 g, 3.99 mL, 25.83 mmol) was added to the solution at 0° C. It was then followed by the addition of Diethyl-azabutane-1,4-dicarboxylate (5 g, 24.6 mmol) and dimethylamino pyridine (0.305 g, 2.5 mmol). The solution was brought to room temperature and stirred further for 6 h. Completion of the reaction was ascertained by TLC. The reaction mixture was concentrated under vacuum and ethyl acetate was added to precipitate diisopropyl urea. The suspension was filtered. The filtrate was washed with 5% aqueous hydrochloric acid, 5% sodium bicarbonate and water. The combined organic layer was dried over sodium sulfate and concentrated to give the crude product which was purified by column chromatography (50% EtOAC/Hexanes) to yield 11.87 g (88%) of AB.

3-[(6-Amino-hexanoyl)-ethoxycarbonylmethyl-amino]-propionic acid ethyl ester AC

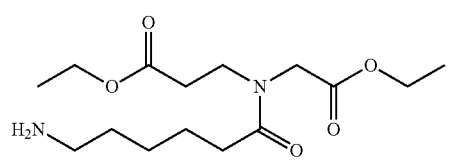

3-{Ethoxycarbonylmethyl-[6-(9H-fluoren-9-ylmethoxycarbonylamino)-hexanoyl]-amino}-propionic acid ethyl ester AB (11.5 g, 21.3 mmol) was dissolved in 20% piperidine in dimethylformamide at 0° C. The solution was continued stirring for 1 h. The reaction mixture was concentrated under vacuum, water was added to the residue, and the product was extracted with ethyl acetate. The crude product was purified by conversion into its hydrochloride salt.

3-({6-[17-(1,5-Dimethyl-hexyl)-10,13-dimethyl-2,3,
4,7,8,9,10,11,12,13,14,15,16,17-tetradecahydro-1H-
cyclopenta[a]phenanthren-3-yloxycarbonylamino]-
hexanoyl}ethoxycarbonylmethyl-amino)-propionic
acid ethyl ester AD Potassium t-butoxide (1.1 g, 9.8 mmol) was slurried in 30 mL of dry toluene. The mixture was cooled to 0° C. on ice and 5 g (6.6 mmol) of diester AD was added slowly with stirring within 20 mins. The temperature was kept below 5° C. during the addition. The stirring was continued for 30 mins at 0° C.

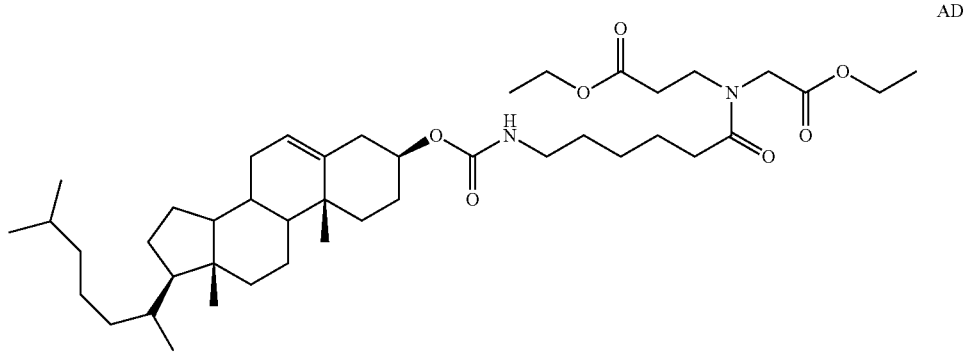

AD

The hydrochloride salt of 3-[(6-Amino-hexanoyl)-ethoxycarbonylmethyl-amino]-propionic acid ethyl ester AC (4.7 g, 14.8 mmol) was taken up in dichloromethane. The suspension was cooled to 0° C. on ice. To the suspension diisopropylethylamine (3.87 g, 5.2 mL, 30 mmol) was added. To the resulting solution cholesteryl chloroformate (6.675 g, 14.8 mmol) was added. The reaction mixture was stirred overnight. The reaction mixture was diluted with dichloromethane and washed with 10% hydrochloric acid. The product was purified by flash chromatography (10.3 g, 92%).

1-{6-[17-(1,5-Dimethyl-hexyl)-10,13-dimethyl-2,3,
4,7,8,9,10,11,12,13,14,15,16,17-tetradecahydro-1H-
cyclopenta[a]phenanthren-3-yloxycarbonylamino]-
hexanoyl}-4-oxo-pyrrolidine-3-carboxylic acid ethyl
ester AE and 1 mL of glacial acetic acid was added, immediately followed by 4 g of $NaH_2PO_4.H_2O$ in 40 mL of water The resultant mixture was extracted twice with 100 mL of dichloromethane each and the combined organic extracts were washed twice with 10 mL of phosphate buffer each, dried, and evaporated to dryness. The residue was dissolved in 60 mL of toluene, cooled to 0° C. and extracted with three 50 mL portions of cold pH 9.5 carbonate buffer. The aqueous extracts were adjusted to pH 3 with phosphoric acid, and extracted with five 40 mL portions of chloroform which were combined, dried and evaporated to dryness. The residue was purified by column chromatography using 25% ethylacetate/hexane to afford 1.9 g of b-ketoester (39%).

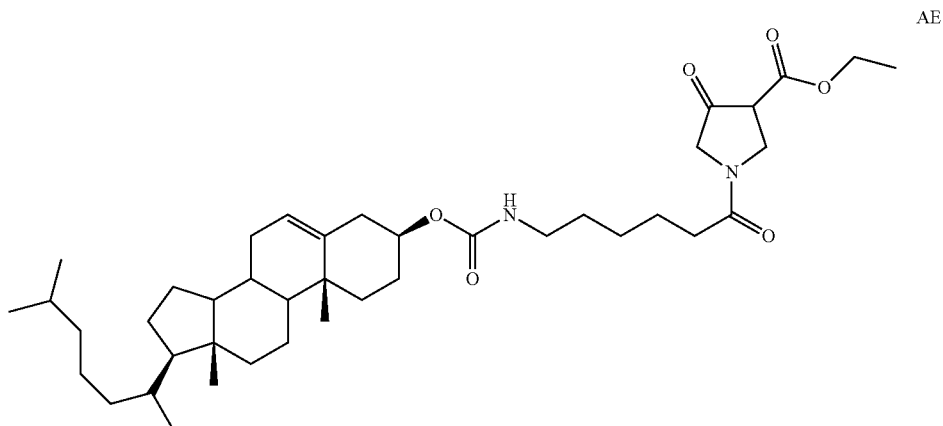

AE

[6-(3-Hydroxy-4-hydroxymethyl-pyrrolidin-1-yl)-6-oxo-hexyl]-carbamic acid 17-(1,5-dimethyl-hexyl)-10,13-dimethyl-2,3,4,7,8,9,10,11,12,13,14,15,16,17-tetradecahydro-1H-cyclopenta[a]phenanthren-3-yl ester AF

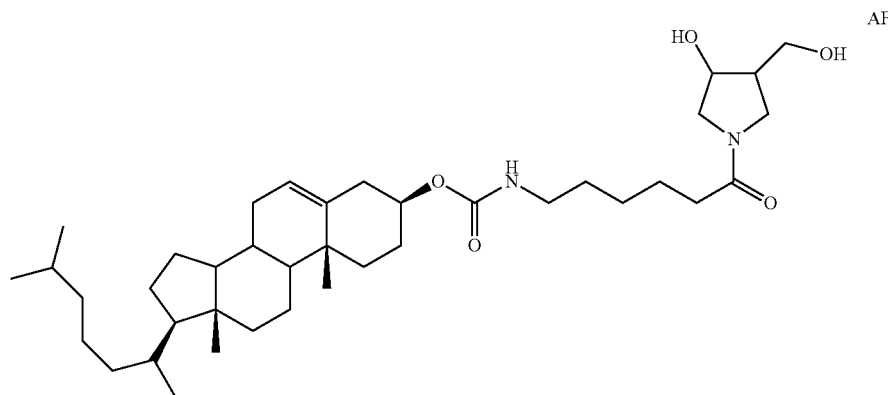

Methanol (2 mL) was added dropwise over a period of 1 h to a refluxing mixture of b-ketoester AE (1.5 g, 2.2 mmol) and sodium borohydride (0.226 g, 6 mmol) in tetrahydrofuran (10 mL). Stirring was continued at reflux temperature for 1 h. After cooling to room temperature, 1 N HCl (12.5 mL) was added, the mixture was extracted with ethylacetate (3×40 mL). The combined ethylacetate layer was dried over anhydrous sodium sulfate and concentrated under vacuum to yield the product which was purified by column chromatography (10% MeOH/CHCl$_3$) (89%).

(6-{3-[Bis-(4-methoxy-phenyl)-phenyl-methoxymethyl]-4-hydroxy-pyrrolidin-1-yl}-6-oxo-hexyl)-carbamic acid 17-(1,5-dimethyl-hexyl)-10,13-dimethyl-2,3,4,7,8,9,10,11,12,13,14,15,16,17-tetradecahydro-1H-cyclopenta[a]phenanthren-3-yl ester AG

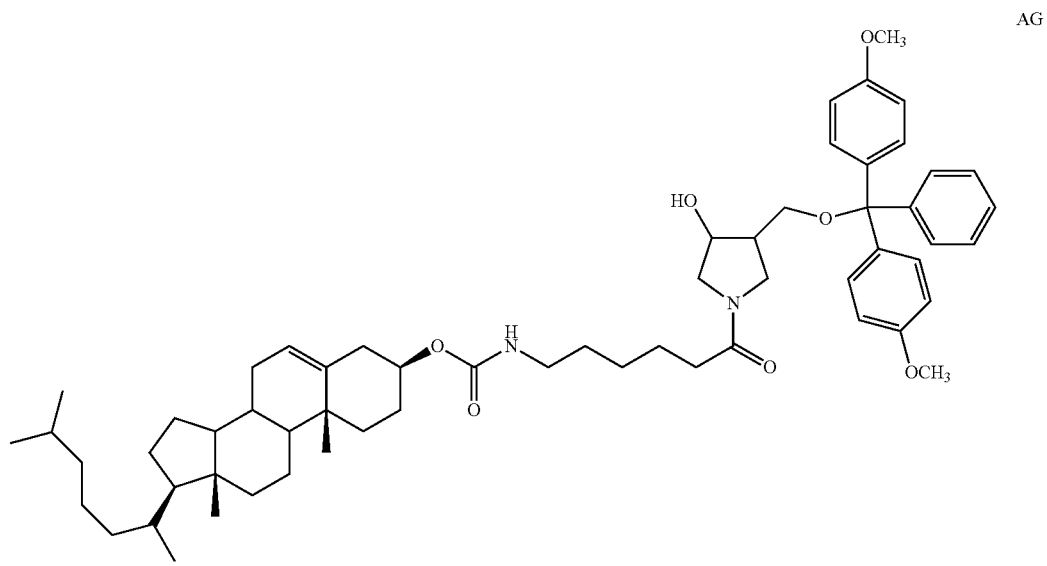

Diol AF (1.25 gm 1.994 mmol) was dried by evaporating with pyridine (2×5 mL) in vacuo. Anhydrous pyridine (10 mL) and 4,4'-dimethoxytritylchloride (0.724 g, 2.13 mmol) were added with stirring. The reaction was carried out at room temperature overnight. The reaction was quenched by the addition of methanol. The reaction mixture was concentrated under vacuum and to the residue dichloromethane (50 mL) was added. The organic layer was washed with 1M aqueous sodium bicarbonate. The organic layer was dried over anhydrous sodium sulfate, filtered and concentrated. The residual pyridine was removed by evaporating with toluene. The crude product was purified by column chromatography (2% MeOH/Chloroform, Rf=0.5 in 5% MeOH/CHCl$_3$) (1.75 g, 95%).

Succinic acid mono-(4[bis-(4-methoxy-phenyl)-phenyl-methoxymethyl]-1-{6-[17-(1,5-dimethyl-hexyl)-10,13-dimethyl 2,3,4,7,8,9,10,11,12,13,14,15,16,17-tetradecahydro-1H cyclopenta[a]phenanthren-3-yloxycarbonylamino]-hexanoyl}-pyrrolidin-3-yl) ester AH Succinate AH (0.254 g, 0.242 mmol) was dissolved in a mixture of dichloromethane/acetonitrile (3:2, 3 mL). To that solution DMAP (0.0296 g, 0.242 mmol) in acetonitrile (1.25 mL), 2,2'-Dithio-bis(5-nitropyridine) (0.075 g, 0.242 mmol) in acetonitrile/dichloroethane (3:1, 1.25 mL) were added successively. To the resulting solution triphenylphosphine (0.064 g, 0.242 mmol) in acetonitrile (0.6 ml) was added. The reaction mixture turned bright orange in color. The solution was agitated briefly using a wrist-action shaker (5 mins). Long chain alkyl amine-CPG (LCAA-CPG) (1.5 g, 61 mM) was added. The suspension was agitated for 2 h. The CPG was filtered through a sintered funnel and washed with acetonitrile, dichloromethane and ether successively. Unreacted amino groups were masked using acetic anhydride/pyridine. The achieved loading of the CPG was measured by taking UV measurement (37 mM/g).

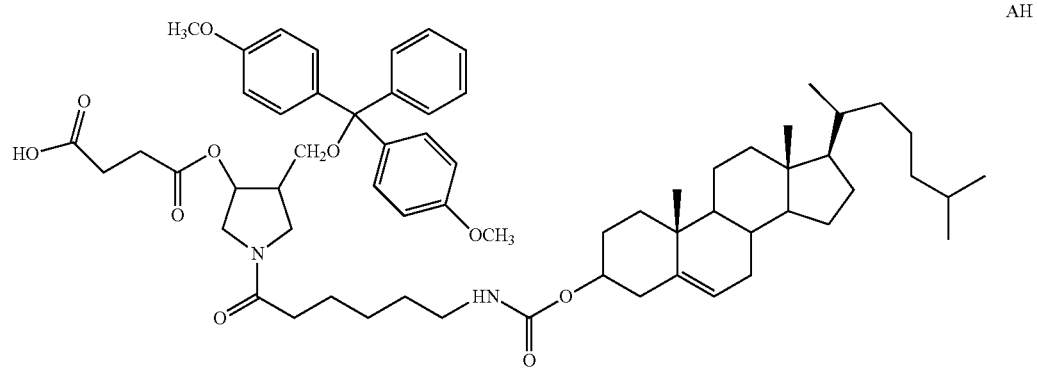

AH

Compound AG (1.0 g, 1.05 mmol) was mixed with succinic anhydride (0.150 g, 1.5 mmol) and DMAP (0.073 g, 0.6 mmol) and dried in a vacuum at 40° C. overnight. The mixture was dissolved in anhydrous dichloroethane (3 mL), triethylamine (0.318 g, 0.440 mL, 3.15 mmol) was added and the solution was stirred at room temperature under argon atmosphere for 16 h. It was then diluted with dichloromethane (40 mL) and washed with ice cold aqueous citric acid (5 wt %, 30 mL) and water (2×20 mL). The organic phase was dried over anhydrous sodium sulfate and concentrated to dryness. The residue was used as such for the next step.
Cholesterol Derivatised CPG AI The synthesis of siRNAs bearing a 5'-12-dodecanoic acid bisdecylamide group (herein referred to as "5'-C32-") or a 5'-cholesteryl derivative group (herein referred to as "5'-Chol-") was performed as described in WO 2004/065601, except that, for the cholesteryl derivative, the oxidation step was performed using the Beaucage reagent in order to introduce a phosphorothioate linkage at the 5'-end of the nucleic acid oligomer.

Nucleic acid sequences are represented below using standard nomenclature, and specifically the abbreviations of Table 3.

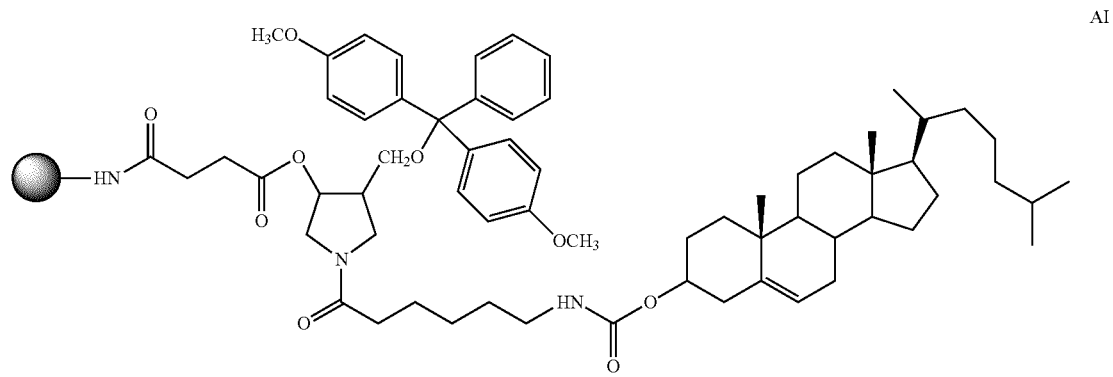

AI

TABLE 3

Abbreviations of nucleotide monomers used in nucleic acid sequence representation. It will be understood that these monomers, when present in an oligonucleotide, are mutually linked by 5'-3'-phosphodiester bonds.

| Abbreviation[a] | Nucleotide(s) |
|---|---|
| A, a | 2'-deoxy-adenosine-5'-phosphate, adenosine-5'-phosphate |
| C, c | 2'-deoxy-cytidine-5'-phosphate, cytidine-5'-phosphate |
| G, g | 2'-deoxy-guanosine-5'-phosphate, guanosine-5'-phosphate |
| T, t | 2'-deoxy-thymidine-5'-phosphate, thymidine-5'-phosphate |
| U, u | 2'-deoxy-uridine-5'-phosphate, uridine-5'-phosphate |
| N, n | any 2'-deoxy-nucleotide/nucleotide (G, A, C, or T, g, a, c or u) |
| am | 2'-O-methyladenosine-5'-phosphate |
| cm | 2'-O-methylcytidine-5'-phosphate |
| gm | 2'-O-methylguanosine-5'-phosphate |
| tm | 2'-O-methyl-thymidine-5'-phosphate |
| um | 2'-O-methyluridine-5'-phosphate |
| Af | 2'-fluoro-2'-deoxy-adenosine-5'-phosphate |
| Cf | 2'-fluoro-2'-deoxy-cytidine-5'-phosphate |
| Gf | 2'-fluoro-2'-deoxy-guanosine-5'-phosphate |
| Tf | 2'-fluoro-2'-deoxy-thymidine-5'-phosphate |
| Uf | 2'-fluoro-2'-deoxy-uridine-5'-phosphate |
| A, C, G, T, U, a, c, g, t, u | underlined: nucleoside-5'-phosphorothioate |
| am, cm, gm, tm, um | underlined: 2-O-methyl-nucleoside-5'-phosphorothioate |

[a]capital letters represent 2'-deoxyribonucleotides (DNA), lower case letters represent ribonucleotides (RNA)

Screen of HD dsRNAs Against Endogenous Human HD mRNA Expression in HeLa Cells HeLa cells were obtained from American Type Culture Collection (Rockville, Md.) and cultured in Ham's F12 (Biochrom AG, Berlin, Germany) supplemented to contain 10% fetal calf serum (FCS) (Biochrom AG, Berlin, Germany), Penicillin 100 U/ml, Streptomycin 100 µg/ml (Biochrom AG, Berlin, Germany) at 37° C. in an atmosphere with 5% $CO_2$ in a humidified incubator (Heraeus HERAcell, Kendro Laboratory Products, Langenselbold, Germany).

For transfection with siRNA, HeLa cells were seeded at a density of $2.0 \times 10^4$ cells/well in 96-well plates and transfected directly. Transfection of siRNA (30 nM for single dose screen) was carried out with oligofectamine (Invitrogen GmbH, Karlsruhe, Germany) as described by the manufacturer. For dose-response curves, siRNA concentrations ranged from 30 nM to 14 pM in 3-fold dilutions.

24 hours after transfection, HeLa cells were lysed and Huntingtin mRNA levels were quantified with the Quantigene Explore Kit (Genosprectra, Dumbarton Circle Fremont, USA) according to the protocol. Huntingtin mRNA levels were normalized to GAPDH mRNA. For each siRNA, four individual datapoints were collected. An siRNA duplex unrelated to the HD gene was used as a control ('VEGF ctrl'). The activity of a given HD-specific siRNA duplex was expressed as percent HD mRNA concentration in treated cells relative to huntingtin mRNA concentration in cells treated with the control siRNA duplex.

Table 1 provides the results from four independent experiments of the in vitro HeLa screen where the siRNAs, the sequences of which are given in Table 1, were tested at a single dose of 30 nM. The percentage of HD mRNA remaining in treated cells compared to controls, ±standard deviation, is indicated in the rightmost column of Table 1. FIG. 1 provides a graph of the results from two independent experiments of the in vitro HeLa screen where siRNAs, the sequences of which are given in Table 2, were tested at a single dose of 30 nM. In Table 2, duplex names are given as AL-DP-xxxx whereas the same duplex in FIG. 1 is indicated by 'xxxx' only. For instance, AL-DP-5997 in Table 2 corresponds to '5997' in FIG. 1. Again, the percentage of HD mRNA remaining in treated cells compared to controls, ±standard deviation, is indicated in the rightmost column of Table 2. A number of siRNAs at 30 nM were effective at reducing HD mRNA levels by more than 70% in HeLa cells.

Table 4 provides the IC50, IC80 and maximum inhibition values from two to five independent experiments for 25 selected siRNAs. Several siRNAs (AL-DP-5997, AL-DP-6000, AL-DP-6001, AL-DP-6014, AL-DP-6020 and AL-DP-6032, indicated by *) were particularly potent in this experimental paradigm, and exhibited IC50 values between 10 and 130 pM.

TABLE 4

| Duplex name | $IC_{50}$ mean [nM] ± SD | $IC_{80}$ mean [nM] ± SD | max. inhib. mean[%] ± SD |
|---|---|---|---|
| AL-DP-5996 | 1.6 ± 1.2 | 22 ± 9 | 79 ± 6 |
| AL-DP-5997* | 0.05 ± 0.02 | 2 ± 1 | 86 ± 5 |
| AL-DP-5999 | 0.3 ± 0.3 | 8 ± 4 | 82 ± 4 |
| AL-DP-6000* | 0.1 ± 0.1 | 5 ± 3 | 80 ± 2 |
| AL-DP-6001* | 0.1 ± 0.1 | 3 ± 1 | 83 ± 1 |
| AL-DP-6002 | 0.3 ± 0.2 | 9 ± 4 | 78 ± 3 |
| AL-DP-6003 | 0.3 ± 0.2 | 3 ± 2 | 83 ± 3 |
| AL-DP-6005 | 0.3 ± 0.3 | 9 ± 9 | 77 ± 7 |
| AL-DP-6006 | 0.5 ± 0.1 | 8 ± 5 | 81 ± 2 |
| AL-DP-6007 | 0.2 ± 0.1 | 5 ± 3 | 77 ± 8 |
| AL-DP-6008 | 0.16 | 13.56 | 75 |
| AL-DP-6014* | 0.1 ± 0.1 | 6 ± 3 | 81 ± 6 |
| AL-DP-6016 | 0.2 ± 0.3 | 8 ± 10 | 81 ± 8 |
| AL-DP-6017 | 0.4 ± 0.1 | 5 ± 4 | 82 ± 2 |
| AL-DP-6018 | 0.2 ± 0.04 | 7 ± 1 | 81 ± 3 |
| AL-DP-6020* | 0.009 ± 0.01 | 1 ± 1 | 88 ± 5 |
| AL-DP-6024 | 0.3 ± 0.1 | 6 ± 4 | 88 ± 1 |
| AL-DP-6025 | 0.3 ± 0.3 | 11 ± 8 | 80 ± 1 |
| AL-DP-6026 | 0.2 ± 0.2 | 5 ± 4 | 81 ± 4 |
| AL-DP-6027 | 0.5 ± 0.1 | 8 ± 6 | 81 ± 2 |
| AL-DP-6032* | 0.016 ± 0.01 | 3 ± 5 | 87 ± 7 |
| AL-DP-6033 | 0.3 ± 0.2 | 6 ± 2 | 78 ± 3 |
| AL-DP-6034 | 0.7 ± 0.03 | 10 ± 3 | 77 ± 4 |
| AL-DP-6035 | 0.8 ± 0.9 | 7 ± 5 | 80 ± 11 |
| AL-DP-6037 | 0.2 ± 0.1 | 8 ± 7 | 79 ± 6 |

Screen of Selected HD dsRNAs Against Endogenous HD mRNA Expression in Neuroscreen and U87MG Cells Neuroscreen cells (a PC12 sub-clone) were obtained from Cellomics (Pittsburgh, Pa.) and cultured in RPMI 1640 (Biochrom AG, Berlin, Germany) supplemented to contain 5% fetal calf serum (FCS) (Biochrom AG, Berlin, Germany), 10% DHS (Biochrom AG, Berlin, Germany), Penicillin 100 U/ml, Streptomycin 100 µg/ml (Biochrom AG, Berlin, Germany) and 2 mM L-glutamine (Biochrom AG, Berlin, Germany) at 37° C. in an atmosphere with 5% $CO_2$ in a humidified incubator (Heraeus HERAcell, Kendro Laboratory Products, Langenselbold, Germany).

U87MG cells were obtained from American Type Culture Collection (Rockville, Md.) and cultured in Ham's F12 (Biochrom AG, Berlin, Germany) supplemented to contain 10% fetal calf serum (FCS) (Biochrom AG, Berlin, Germany), Penicillin 100 U/ml, Streptomycin 100 µg/ml (Biochrom AG, Berlin, Germany) at 37° C. in an atmosphere with 5% $CO_2$ in a humidified incubator (Heraeus HERAcell, Kendro Laboratory Products, Langenselbold, Germany).

Transfection of Neuroscreen and U87MG cells with six selected siRNAs (AL-DP-5997, AL-DP-6000, AL-DP-6001, AL-DP-6014, AL-DP-6020 and AL-DP-6032), and quantitation of Huntingtin and GAPDH mRNA levels with the Quantigene Explore Kit were performed in a similar manner to that described for HeLa cells.

IC50 values are provided in Table 5. In both Neuroscreen (rat) and U87MG (human) cells, IC50s were higher than in HeLa cells, in general. Of the six siRNAs tested, AL-DP-6014 was significantly less potent than the other five siRNAs (AL-DP-5997, AL-DP-6000, AL-DP-6001, AL-DP-6020 and AL-DP-6032) against HD mRNA in Neuroscreen cells, whereas AL-DP-6000 was significantly less potent than the other five siRNAs (AL-DP-5997, AL-DP-6001, AL-DP-6014, AL-DP-6020 and AL-DP-6032) against HD mRNA in U87MG cells.

TABLE 5

| Duplex name | Neuroscreen IC50 mean [nM] +/− SD | U87MG IC50 mean [nM] |
|---|---|---|
| AL-DP-5997 | 6 ± 2.8 | 2.7 |
| AL-DP-6000 | 11.7 ± 10 | 98 |
| AL-DP-6001 | 18 | 0.28 |
| AL-DP-6014 | 264 ± 180 | 0.47 |
| AL-DP-6020 | 1.42 ± 0.2 | 0.17 |
| AL-DP-6032 | 4.2 ± 2.2 | 0.49 | dsRNAs Targeting HD Reduce Endogenous HD Protein in HeLa Cells

Hela cells were cultured and transfected as previously described with 100 nM of the indicated siRNAs, including six siRNAs against HD (AL-DP-5997, AL-DP-6000, AL-DP-6001, AL-DP-6014, AL-DP-6020 and AL-DP-6032) and one control unrelated siRNA ('ctrl'). 48 hours post-transfection, the cells were harvested and lysed. Proteins in the lysates were separated on an 8% denaturing PAG. Huntingtin and β-actin were detected by standard western blot protocols using antibodies that bind to the proteins. For Huntingtin detection, the membrane was probed with a mouse anti-huntingtin protein monoclonal antibody (Chemicon, U.K.) followed by a horseradish peroxidase-coupled goat anti-mouse secondary antibody (Santa Cruz Biotechnology, California). β-actin was detected by anti-actin goat polyclonal IgG (Santa Cruz, Calif.) followed by a donkey anti-goat Ig-HRP secondary antibody (Santa Cruz, Calif.).

Figure 2:
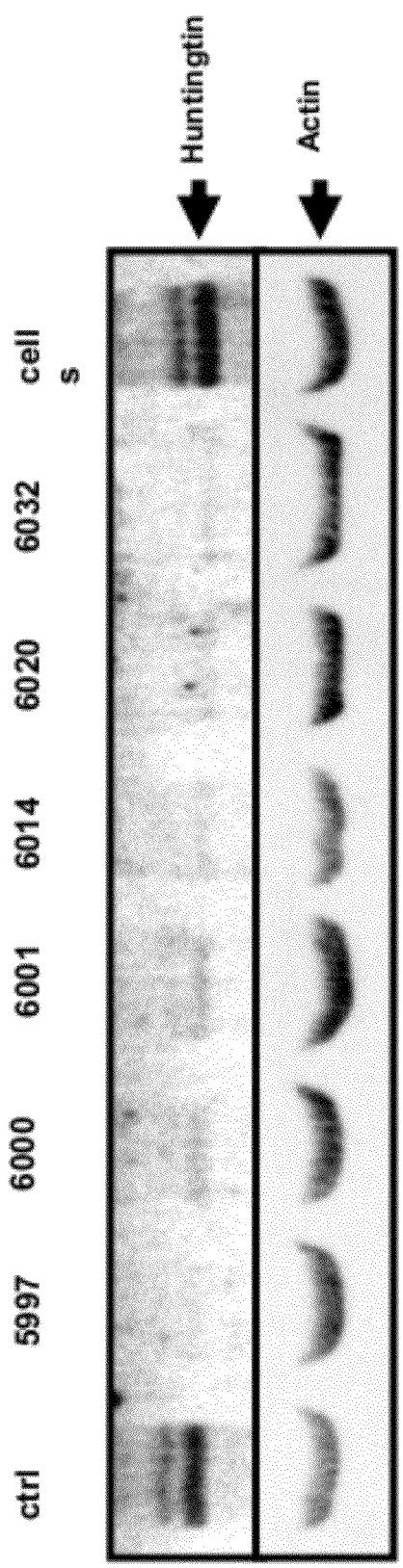
FIG. 2. Activity of selected dsRNAs in reducing endogenous human HD protein formation in HeLa cells.

FIG. 2 provides the results. AL-DP-5997 ('5997'), AL-DP-6000 ('6000'), AL-DP-6001 ('6001'), AL-DP-6014 ('6014'), AL-DP-6020 ('6020') and AL-DP-6032 ('6032'), a decreased the level of Huntingtin protein relative to the control protein β-actin, whereas the control unrelated siRNA ('ctrl') had no effect on the level of either protein. These results demonstrate that dsRNAs targeting HD effectively reduce not only HD mRNA levels, but also HD protein levels.

Stability in Cerebrospinal Fluid (CSF) of Selected dsRNAs Targeting HD

Figure 3:
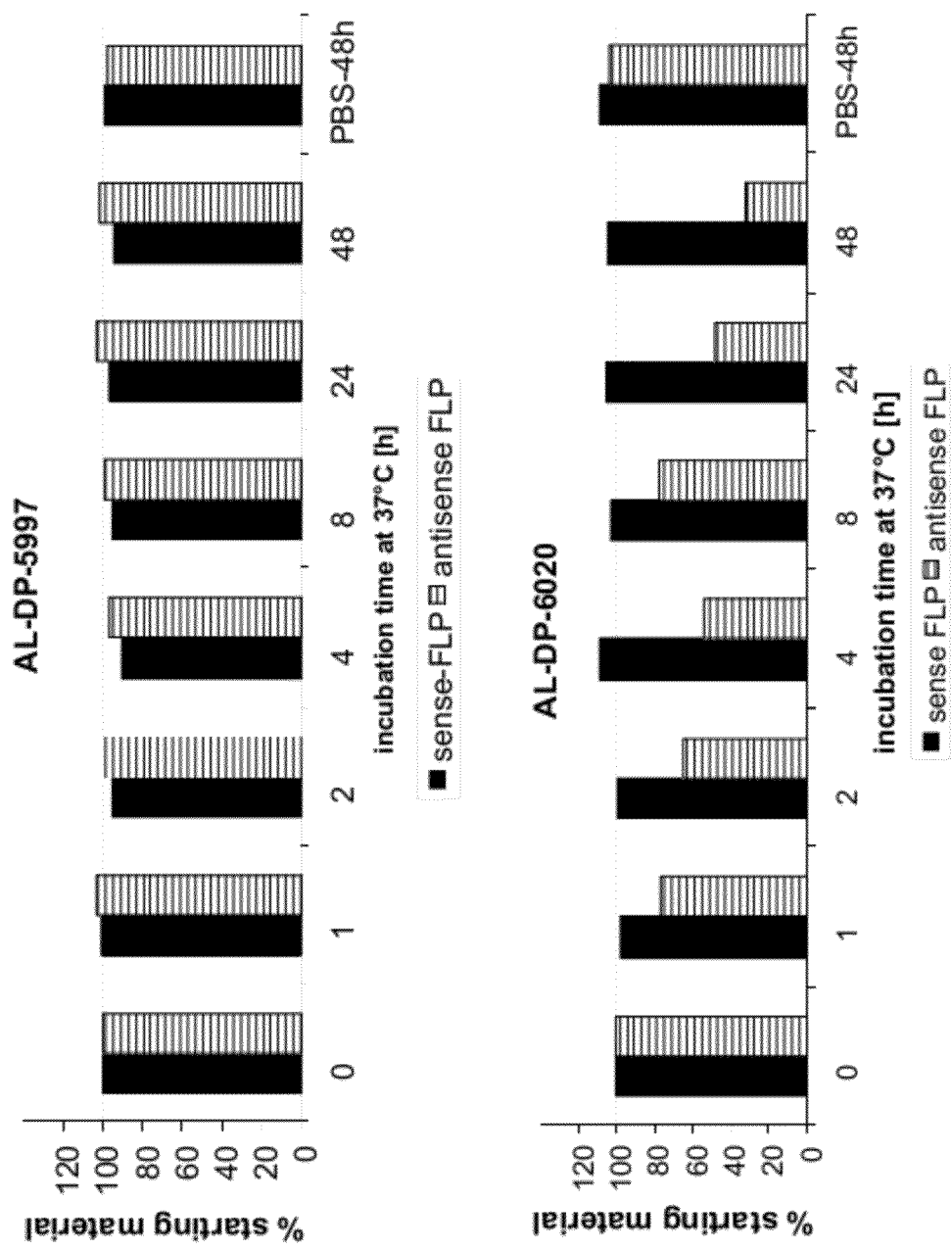
FIG. 3. Stability of selected dsRNAs in cerebrospinal fluid (CSF) at 37° C.

Six selected siRNAs (AL-DP-5997, AL-DP-6000, AL-DP-6001, AL-DP-6014, AL-DP-6020 and AL-DP-6032) were tested for stability at 5 uM over 48 h at 37° C. in calf and swine CSF, as well as in PBS for comparison. The incubations in CSF were stopped at 1, 2, 4, 8, 24 and 48 hours by proteinase digestion, whereas the incubation in PBS was stopped at 0 and 48 hours. Filtered samples were injected onto the IEX-HPLC under denaturing conditions, and percent recovery of each single strand was determined by measuring the area under the corresponding peak, and expressing this area relative to that obtained at 0 hours in PBS. FIG. 3 and Table 6 provide the results. At least 90% of both sense and antisense strands of AL-DP-5997, AL-DP-6000 and AL-DP-6014 were recovered in both calf and swine CSF (Table 6). In contrast, although 92% of the antisense strand of AL-DP-6001 was recovered in calf CSF, only 73% of the antisense strand was recovered in swine CSF. For AL-DP-6020 and AL-DP-6032, at least 19% of the antisense strand was not recoverable in both calf and swine CSF.

TABLE 6

| | % full length material after 48 hours | | | |
|---|---|---|---|---|
| | calf | | swine | |
| AL-DP | sense | antisense | sense | antisense |
| 5997 | 103 | 99 | 95 | 101 |
| 6000 | 114 | 101 | 114 | 97 |
| 6001 | 100 | 92 | 100 | 73 |
| 6014 | 91 | 90 | 90 | 94 |
| 6020 | 113 | 68 | 104 | 32 |
| 6032 | 95 | 21 | 103 | 81 |

The following cleavage sites for AL-DP-6020 and AL-DP-6032 were mapped by comparing the calculated theoretical masses of all probable fragments of both strands with the experimental masses found by MALDI-TOF. For the antisense strand of AL-DP-6020, the fragment 5'-gauuuumag-gaauuccmaau-cyclic-PO4-3' (SEQ ID NO: 874) corresponds to 3'-(n-3) based on the calculated mass of 5973.5 Da, and experimental mass of 5973.0 Da. For the antisense strand of AL-DP-6032, the fragment 5'-uumaggaauuccmaaugaucTT-3' (SEQ ID NO: 875) corresponds to 5'-(n-1) based on the calculated mass of 6355.0 Da, and experimental mass of 6355.6 Da. Given these cleavage sites, 2 new duplexes were designed with additional chemical stabilization that comprises one additional 2'-OMe group (Table 7): AL-DP-7100 (parent is AL-DP-6020) and AL-DP-7101 (parent is AL-DP-6032).

TABLE 7

Sequences and Modifications of Further Stabilized dsRNAs AL-DP-7100 and AL-DP-7101

| Duplex name | Sense strand sequence (5'-3') | SEQ ID NO: | Antisense strand sequence (5'-3') | SEQ ID NO: |
|---|---|---|---|---|
| Al-DP-7100 | cmaumumggaaumumcmcmumaaaaumcmTT | 876 | gauuuumaggaauuccmaaumgTT | 877 |
| Al-DP-7101 | gaumcmaumumggaaumumcmcmumaaaTT | 878 | umuumaggaauuccmaaugaucTT | 879 |

Figure 4:
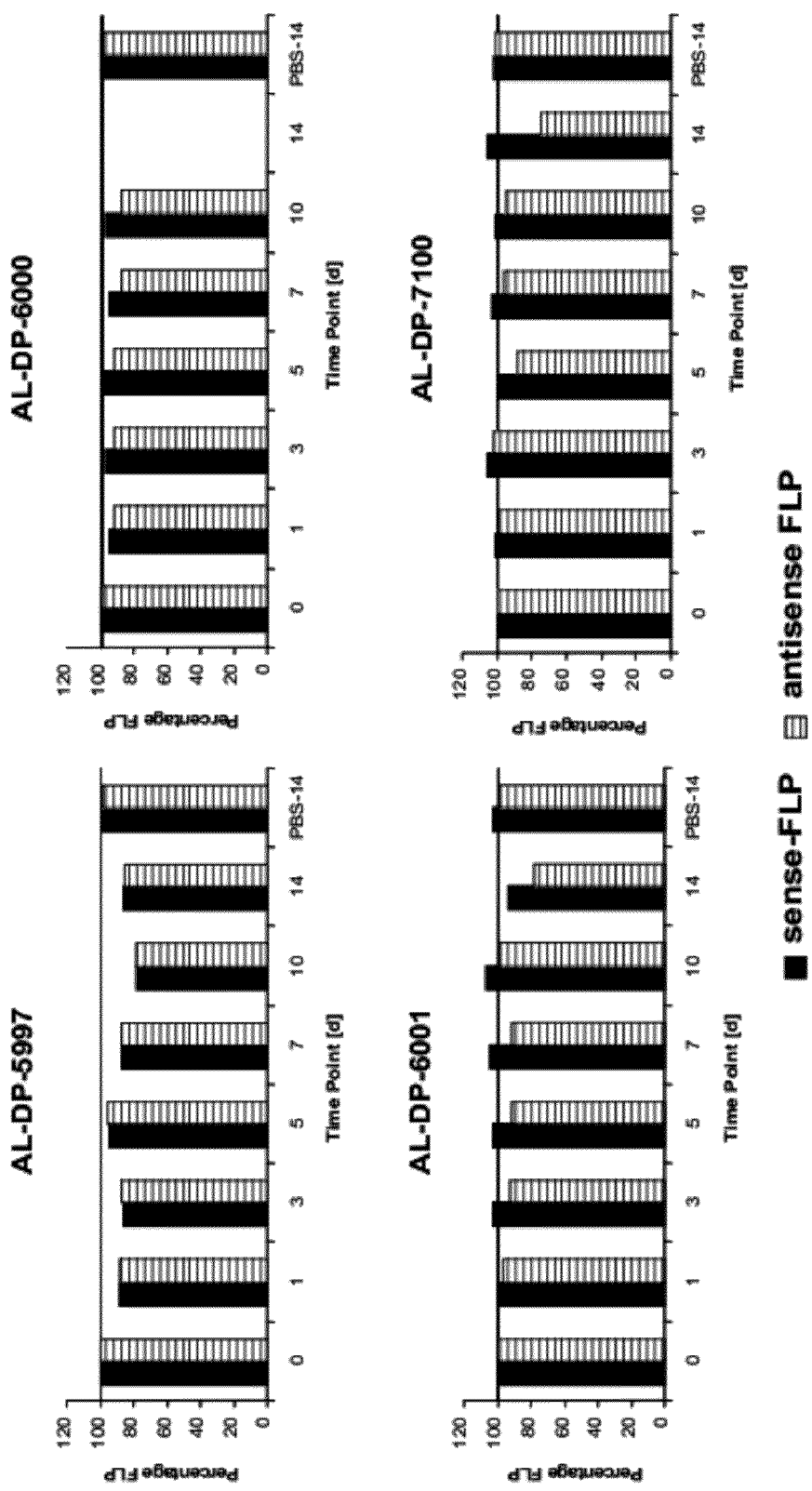
FIG. 4. Long-term stability of dsRNAs AL-DP-5997, AL-DP-6000, AL-DP-6001 and AL-DP-7100 in rat CSF

Four selected dsRNAs (AL-DP-5997, AL-DP-6000, AL-DP-6001 and AL-DP-7100) were tested for long-term stability at 5 uM over 14 days at 37° C. in rat CSF, as well as in PBS for comparison. The incubations in CSF were carried out for 0, 1, 3, 5, 7, 10, or 14 days whereas the incubation in PBS was carried out for 14 days. Samples were processed as described above. FIG. 4 shows the results. For AL-DP-6000, the 14 day CSF stability timepoint is not available, for technical reasons. All four dsRNAs are highly stable for 10 to 14 days at 37° C. in rat CSF, with ≦30% loss of antisense or sense strands.

Potency of Cholesterol-Conjugated dsRNAs Targeting HD Against Endogenous Human HD mRNA Expression in HeLa Cells Previous studies [Soutschek et al., 2004] had demonstrated a beneficial effect of cholesterol conjugation on cellular uptake and/or efficacy of siRNA in vivo. We synthesized dsRNAs AL-DP-6982, AL-DP-6983 and AL-DP-7130 (Table 8) which are cholesterol-conjugated versions of AL-DP-5997, AL-DP-6000 and AL-DP-7100, respectively, in order to evaluate their biological activities in vitro and in vivo. Hela cells were cultured and transfected as previously described, with dsRNAs AL-DP-6982, AL-DP-6983, AL-DP-7130, AL-DP-5997, AL-DP-6000, and AL-DP-7100 at concentrations ranging from 30 nM to 14 pM.

24 hours after transfection, HeLa cells were lysed and Huntingtin and GAPDH mRNA levels were quantified as described above. For each siRNA, four individual datapoints were collected. An siRNA duplex unrelated to the HD gene was used as a control. The activity of a given siRNA duplex targeting HD was expressed as percent HD mRNA concentration in treated cells relative to the HD mRNA concentration in cells treated with the control siRNA duplex. XL-fit was used to calculate $IC_{50}$ values; the mean $IC_{50}$ values were calculated from three independent determinations, and are shown in Table 9.

TABLE 9

Potency of Cholesterol-Conjugated dsRNAs AL-DP-6982, AL-DP-6983 and AL-DP-7130 Compared with Unconjugated dsRNAs AL-DP-5997, AL-DP-6000 and AL-DP-7100 against endogenous human HD mRNA expression in HeLa cells

| Duplex name | IC50 (mean, nM) |
|---|---|
| AL-DP-5997 | 0.04 |
| AL-DP-6982 | 0.73 |
| AL-DP-6000 | 0.24 |
| AL-DP-6983 | 14.0 |
| AL-DP-7100 | 0.03 |
| AL-DP-7130 | 0.38 |

The unconjugated dsRNAs exhibited expected (Table 4) potencies in vitro against HD mRNA. The cholesterol-conjugated dsRNAs retain biological activity in vitro against HD mRNA, although the potencies are somewhat reduced compared to the unconjugated parent molecules.

In Vivo Down-Modulation of Endogenous HD mRNA Levels by CNS Administration of Unconjugated or Cholesterol-Conjugated dsRNAs Targeting HD in Rats and Mice

TABLE 8

Sequences of Cholesterol-Conjugated dsRNAs AL-DP-6982, AL-DP-6983 and AL-DP-7130

| Duplex name | Sense strand sequence (5'-3') | SEQ ID NO: | Antisense strand sequence (5'-3') | SEQ ID NO: |
|---|---|---|---|---|
| AL-DP-6982 | gumcmacmaaagaacmcmgumgcmagTT-sChol | 880 | cugcmacgguucuuugugacTT | 881 |
| AL-DP-6983 | umcmcmumgcmumumumagumcmgagaacmTT-sChol | 882 | guucucgacumaaagcmaggaTT | 883 |
| AL-DP-7130 | cmaumumggaaumumcmcmumaanaumcmTT-sChol | 884 | gauuuumaggaauuccmaaumgTT | 885 |

Note:
's' represents a phosphorothioate bound inbetween T and cholesterol, Chol represents cholesterol-conjugate To assess both the in vivo biological activity and distribution of unconjugated or cholesterol-conjugated dsRNAs targeting HD, dsRNAs AL-DP-1997 and AL-DP-1998 (Table 10), based on AL-DP-5997, were synthesized in which the two 2'-deoxy-thymidine-5'-phosphate nucleotides at the 3'-end of the antisense strand (outside of the dsRNA's nucleotide region that targets the HD mRNA) were replaced with 5-bromo-2'-deoxyuridine.

TABLE 10

Sequences of dsRNAs AL-DP-1997 and AL-DP-1998

| Duplex name | Sense strand sequence (5'-3') | SEQ ID NO: | Antisense strand sequence (5'-3') | SEQ ID NO: |
|---|---|---|---|---|
| AL-DP-1997 | gumcmacmaaagaacmcmgumgcmagT<u>T</u> | 886 | cugcmacgguucuuugugacB<u>B</u> | 887 |
| AL-DP-1998 | gumcmacmaaagaacmcmgumgcmagTT-Chol | 888 | cugcmacgguucuuugugacB<u>B</u> | 889 |

Note:
'B' represents 5-bromo-2'-deoxyuridine, underline designates nucleoside-5'-phosphorothioate, Chol represents cholesterol-conjugate In rats, 1.3 mg AL-DP-1997 or AL-DP-1998, or phosphate-buffered saline (PBS, vehicle control) was administered by continuous intrastriatal infusion over 7 days. Male Sprague-Dawley rats, approximately 250-300 g body weight, received stereotaxic implantation of 30-gauge infusion cannulae (Plastics One, Roanok, Va.) such that unilateral injections were targeted to the center of the striatum (anteroposterior+0.7 mm, mediolateral+3.0 mm, relative to bregma; dorsoventral 5 mm, relative to skull surface). Mini-osmotic pumps (model 1007D) were primed overnight according to the manufacturer's specifications, implanted subcutaneously, and connected via catheters, to deliver (4 rats per treatment group) PBS, 1.1 mM AL-DP-1997 or 1.1 mM AL-DP-1998 at 0.5 uL/hr over 7 days. At the end of the 7 day infusion period, animals were sacrificed, brains were removed, and ipsilateral striata encompassing the infusion site were flash frozen. Tissue samples of about 5-30 mg each were homogenized by sonication (BANDELIN electronic GmbH & Co. KG, Berlin, Germany) in Tissue and Cell Lysis solution (Epicentre, Madison, Wis.) containing 84 µg/ml Proteinase K (Epicentre, Madison, Wis.). Lysates were then stored at −80° C. For carrying out the bDNA assay, frozen lysates were thawed at room temperature, and Huntingtin and GAPDH mRNA were quantified using the Quantigene Explore Kit according to the manufacturer's instructions. For each tissue sample, the ratio of Huntingtin/GAPDH (normalized Huntingtin mRNA level) was calculated as an average of four determinations. These ratios were then averaged to obtain a group (treatment) average. The unconjugated dsRNA, AL-DP-1997, reduced the normalized Huntingtin mRNA level by 33%, relative to the PBS control group, whereas the cholesterol-conjugated dsRNA, AL-DP-1998, reduced the normalized Huntingtin mRNA level by 26%, relative to the PBS control group. Both reductions were statistically significant ($p<0.05$, ANOVA with Tukey post-hoc analysis). These results demonstrate that intrastriatal AL-DP-1997 and AL-DP-1998 are efficacious in vivo in down-modulating HD mRNA levels.

With an identical experimental paradigm, AL-DP-5997 and AL-DP-6000 were also found to be effective in vivo in down-modulating HD mRNA levels after intrastriatal infusion with 1.3 mg over 7 days (0.5 uL/hr at 1.1 mM) in rats. AL-DP-5997 and AL-DP-6000 reduced the normalized Huntingtin mRNA levels in striatal tissue by 34% and 36%, respectively, relative to the PBS control group. In addition, AL-DP-5997 and AL-DP-6000 reduced the normalized Huntingtin mRNA levels in cortical tissue by 22% and 26% respectively. These results demonstrate that these unconjugated siRNAs, after intrastriatal infusion, not only down-modulate HD mRNA levels within the striatum, but also in the cortex, another major brain region where neuronal loss occurs in Huntington's disease and which is located further from the infusion site.

In mice, 75 ug AL-DP-1998, or phosphate-buffered saline (PBS, vehicle control) was administered by a 20 minute intrastriatal infusion. Male Balb/c mice, approximately 20-25 g body weight, received unilateral injections of test article that were targeted to the striatum (anteroposterior+0.5 mm, mediolateral+2.0 mm, relative to bregma; dorsoventral 3.5 mm, relative to skull surface). Test articles (1.1 mM) were injected (4 animals per test article) at 0.25 uL/min. using pre-filled, pump-regulated Hamilton micro-syringes connected to a 33 gauge needle. Approximately 72 hours following the injection, animals were sacrificed, brains were removed, and ipsilateral striata encompassing the infusion site were dissected and flash frozen. As described above for rat tissue samples, mouse tissue samples were lysed, and Huntingtin and GAPDH mRNA levels quantified. For each tissue sample, the ratio of Huntingtin/GAPDH (normalized Huntingtin mRNA level) was calculated as an average of four determinations. These ratios were then averaged to obtain a group (treatment) average. The cholesterol-conjugated dsRNA, AL-DP-1998, reduced the normalized Huntingtin mRNA level by 33%, relative to the PBS control group, which was statistically significant ($p<0.05$, ANOVA with Tukey post-hoc analysis). These results further confirm that AL-DP-1998 is efficacious in vivo in down-modulating HD mRNA levels. In addition, these results demonstrate that a total intrastriatal dose of AL-DP-1998 as low as 75 ug resulted in significant down-modulation of HD mRNA levels.

We claim:

1. A pharmaceutical composition comprising a double stranded ribonucleic acid (dsRNA) comprising a sense strand and an antisense strand and a pharmaceutically acceptable carrier, wherein the antisense strand comprises a nucleotide sequence consisting of SEQ ID NO:793 and a 2'-O-methyl modified nucleotide at location 4 and the sense strand comprises a nucleotide sequence consisting of SEQ ID NO:792 and a 2'-O-methyl modified nucleotide at locations 2, 3, 5, 12, 13, 15, and 17.

2. The dsRNA of claim 1, wherein said dsRNA comprises at least one additional modified nucleotide.

3. The dsRNA of claim 2, wherein said modified nucleotide is chosen from the group of: a 2'-O-methyl modified nucleotide, a nucleotide comprising a 5' phosphorothioate group, and a terminal nucleotide linked to a cholesteryl derivative or dodecanoic acid bisdecylamide group.

4. The dsRNA of claim 2, wherein said modified nucleotide is chosen from the group of: a 5-bromo-2'-deoxyuridine, a 2'-deoxy-2'-fluoro modified nucleotide, a 2'-deoxy-modified nucleotide, a locked nucleotide, an abasic nucleotide, 2'-amino-modified nucleotide, 2'-alkyl-modified nucleotide, morpholino nucleotide, a phosphoramidate, and a non-natural base comprising nucleotide.

5. The pharmaceutical composition of claim 1, wherein said dsRNA comprises a cholesterol moiety.

6. A method for inhibiting expression of Huntingtin (HD) gene in a cell, the method comprising: (a) introducing into the cell the pharmaceutical composition of claim 2, 3, or 4; and (b) maintaining the cell produced in step (a) for a time sufficient to obtain degradation of the mRNA transcript of the HD gene, thereby inhibiting expression of the HD gene in the cell.

7. A method of treating or managing Huntingtin disease comprising administering to a patient in need of such treatment or management a therapeutically effective amount of the pharmaceutical composition of claim 2, 3, or 4.

8. The method of claim 7, wherein the pharmaceutical composition is administered to the brain of the patient.

9. The method of claim 7, wherein the pharmaceutical composition is administered by intrastriatal infusion.

10. The method of claim 8, wherein administering the pharmaceutical composition to the brain causes a decrease in Huntingtin (HD) gene mRNA in the striatum.

11. The method of claim 8, wherein administering the pharmaceutical composition to the brain causes a decrease in Huntingtin (HD) gene mRNA in the cortex.

12. The method of claim 6, wherein the dsRNA of the pharmaceutical composition comprises a cholesterol moiety.

13. The method of claim 6, wherein the pharmaceutical composition is administered in vivo to a mammal.

14. The method of claim 12, wherein the pharmaceutical composition is administered in vivo to a mammal.

15. The method of claim 6, wherein the pharmaceutical composition is administered by intrastiatal infusion.

16. The method of claim 12, wherein the pharmaceutical composition is administered by intrastiatal infusion.

17. The method of claim 7, wherein the dsRNA of the pharmaceutical composition comprises a cholesterol moiety.

18. The method of claim 17, wherein the pharmaceutical composition is administered to the brain of the patient.

19. The method of claim 17, wherein the pharmaceutical composition is administered by intrastriatal infusion.

20. The method of claim 18, wherein administering the pharmaceutical composition to the brain causes a decrease in Huntingtin (HD) gene mRNA in the striatum.

21. The method of claim 18, wherein administering the pharmaceutical composition to the brain causes a decrease in Huntingtin (HD) gene mRNA in the cortex.

22. The pharmaceutical composition of claim 1, wherein the pharmaceutically acceptable carrier consists of an aqueous buffer.

23. The method of claim 6, wherein the pharmaceutically acceptable carrier consists of an aqueous buffer.

24. The method of claim 7, wherein the pharmaceutically acceptable carrier consists of an aqueous buffer.

25. The pharmaceutical composition of claim 1, wherein the antisense strand comprises a phosphorothioate at the internucleotide linkage between nucleotides 20 and 21 and the sense strand comprises a phosphorothioate at the internucleotide linkage between nucleotides 20 and 21.

26. The method of claim 6, wherein the antisense strand comprises a phosphorothioate at the internucleotide linkage between nucleotides 20 and 21 and the sense strand comprises a phosphorothioate at the internucleotide linkage between nucleotides 20 and 21.

27. The method of claim 7, wherein the antisense strand comprises a phosphorothioate at the internucleotide linkage between nucleotides 20 and 21 and the sense strand comprises a phosphorothioate at the internucleotide linkage between nucleotides 20 and 21.

28. A method of inhibiting expression of Huntingtin (HD) gene in a cell in a patient comprising administering to the brain of the patient by intrastriatal infusion a therapeutically effective amount of a pharmaceutical composition comprising a dsRNA and an aqueous buffer, the dsRNA consisting of a sense strand and antisense strand, wherein the antisense strand comprises a nucleotide sequence consisting of SEQ ID NO:793 and a 2'-O-methyl modified nucleotide at location 4 and a phosphorothioate at the internucleotide linkage between nucleotides 20 and 21 and the sense strand comprises a nucleotide sequence consisting of SEQ ID NO:792 and said sense strand comprises a 2'-O-methyl modified nucleotide at locations 2, 3, 5, 12, 13, 15, and 17 and a phosphorothioate at the internucleotide linkage between nucleotides 20 and 21.

29. A method of treating or managing Huntintin disease in a patient comprising administering to the brain of the patient by intrastriatal infusion a therapeutically effective amount of a pharmaceutical composition comprising a dsRNA and an aqueous buffer, the dsRNA consisting of a sense strand and antisense strand, wherein the antisense strand comprises a nucleotide sequence consisting of SEQ ID NO:793 and a 2'-O-methyl modified nucleotide at location 4 and a phosphorothioate at the internucleotide linkage between nucleotides 20 and 21 and the sense strand comprises a nucleotide sequence consisting of SEQ ID NO:792 and a 2'-O-methyl modified nucleotide at locations 2, 3, 5, 12, 13, 15, and 17 and a phosphorothioate at the internucleotide linkage between nucleotides 20 and 21.

* * * * *